US009353379B2

(12) United States Patent
Kasahara et al.

(10) Patent No.: US 9,353,379 B2
(45) Date of Patent: May 31, 2016

(54) METHOD FOR CULTIVATION OF GENETICALLY-MODIFIED PLANT

(75) Inventors: Saori Kasahara, Tokyo (JP); Masafumi Wasai, Tokyo (JP); Koichi Sugita, Tokyo (JP); Teruhisa Shimada, Tokyo (JP)

(73) Assignee: NIPPON PAPER INDUSTRIES CO., LTD., Tokyo (JP)

( * ) Notice: Subject to any disclaimer, the term of this patent is extended or adjusted under 35 U.S.C. 154(b) by 882 days.

(21) Appl. No.: 13/147,436

(22) PCT Filed: Aug. 26, 2009

(86) PCT No.: PCT/JP2009/064876
§ 371 (c)(1), (2), (4) Date: Aug. 2, 2011

(87) PCT Pub. No.: WO2010/087048
PCT Pub. Date: Aug. 5, 2010

(65) Prior Publication Data

US 2012/0054923 A1 Mar. 1, 2012

(30) Foreign Application Priority Data

Feb. 2, 2009 (JP) ................................ 2009-021846

(51) Int. Cl.

| | |
|---|---|
| ***A01H 1/00*** | (2006.01) |
| ***C12N 15/82*** | (2006.01) |
| *A01H 5/00* | (2006.01) |
| *A01H 5/10* | (2006.01) |
| *C12N 15/00* | (2006.01) |

(52) U.S. Cl.
CPC ........ *C12N 15/8261* (2013.01); *C12N 15/8234* (2013.01); *C12N 15/8238* (2013.01); *C12N 15/8251* (2013.01); *C12N 15/8257* (2013.01)

(58) Field of Classification Search
None
See application file for complete search history.

(56) References Cited

U.S. PATENT DOCUMENTS

| | | | | |
|---|---|---|---|---|
| 5,654,190 | A | 8/1997 | Matsunaga et al. | |
| 7,192,774 | B2 * | 3/2007 | Takaiwa et al. | 435/468 |
| 2005/0066387 | A1 * | 3/2005 | Yu et al. | 800/278 |
| 2006/0107346 | A1 * | 5/2006 | Schneeberger et al. | 800/278 |
| 2007/0294782 | A1 * | 12/2007 | Abad et al. | 800/278 |

FOREIGN PATENT DOCUMENTS

| | | |
|---|---|---|
| JP | 7 308137 | 11/1995 |
| WO | 2006 095749 | 9/2006 |

OTHER PUBLICATIONS

Pirmoradian et al. Biosystems Engineering, Jan. 2006, vol. 93, No. 1, pp. 25-34.*

Inoue, K., et al., "Calcium Nodo no Kotonaru Joken ni Oite, Suikoekichu no Ammonium-tai Chisso Narabini Shosantai Chisso ga Sakumotsu no Ne no Seiiku ni Oyobosu Eikyo," Japanese Journal of the Science and Plant Nutrition, vol. 57, No. 5, pp. 493-502, (Oct. 5, 1986).

Kawakatsu, T., et al., "Characterization of a new rice glutelin gene GluD-1 expressed in the starchy endosperm," Journal of Experimental Botany, vol. 59, No. 15, pp. 4233-4245, (Nov. 2, 2008).

Proceedings of the 26$^{th}$ Annual Meeting of the Japanese Society for Plant Cell and Molecular Biology, Total 10 Pages, (Sep. 1, 2008).

Presentation Documents of the 72$^{nd}$ Annual Meeting of the Botanical Society of Japan, Total 14 Pages, (Sep. 25, 2008).

Abstracts of the 31$^{st}$ Annual Meeting of the Molecular Biology Society of Japan, and the 81$^{st}$ Annual Meeting of the Japanese Biochemical Society, Total 8 Pages, (Nov. 20, 2008).

International Search Report Issued Nov. 2, 2009 in PCT/JP09/64876 Filed Aug. 26, 2009.

Kouichi Inoue, "Calcium Nodo no Kotonaru Joken ni Oite, Suikoekichu no Ammounium-tai Chisso Narabini Shosantai Chisso ga Sakumotsu no Ne no Seiiku ni Oyobosu Eikyo," Japanese Journal of the Science and Plant Nutrition, vol. 57, No. 5, Oct. 5, 1986, 2 Pages (English Translation only).

Proceedings of the 26th Annual Meeting of the Japanese Society for Plant Cell and Molecular Biology, Sep. 1, 2008, 4 pages (English Translation only).

Presentation Documents of the 72nd Annual Meeting of the Botanical Society of Japan, Sep. 25, 2008, 7 pages (English Translation only).

Abstracts of the 31st Annual Meeting of the Molecular Biology Society of Japan, and the 81st Annual Meeting of the Japanese Biochemical Society, Nov. 20, 2008, 6 pages (English Translation only).

* cited by examiner

*Primary Examiner* — Phuong Bui

(74) *Attorney, Agent, or Firm* — Oblon, McClelland, Maier & Neustadt, L.L.P.

(57) ABSTRACT

The present invention provides a method for cultivation of a genetically-modified plant that can highly produce a desired protein. More specifically, the present invention provides a method for cultivation of a genetically-modified plant comprising: cultivating the genetically-modified plant in a medium, wherein the genetically-modified plant is transformed by introducing an expression vector comprising a promoter regulating expression of RNA and a seed storage protein isolated from a plant that highly expresses RNA and the seed storage protein under a high nitrogen condition; and a polynucleotide encoding an objective protein, and wherein the medium is adjusted so that nitrate nitrogen is 70 mg/L to 750 mg/L and/or ammonium nitrogen is 70 mg/L to 750 mg/L for a definite period in a period from 30 days before an expected flowering date to a date on or before flowering of the genetically-modified plant.

5 Claims, 2 Drawing Sheets

SEEDING (THE 0TH DAY)

PANICLE INITIATION STAGE (THE 50TH DAY)

HEADING, BLOOM STAGE (THE 75TH DAY)

| NUTRITION GROWTH PHASE | | GENERATIVE GROWTH PHASE | GRAIN FILLING PHASE |
|---|---|---|---|
| WATER 15 DAYS | CULTIVATION SOLUTION A 45 DAYS | CULTIVATION SOLUTION B 45 DAYS | |

METHOD FOR CULTIVATION OF GENETICALLY-MODIFIED PLANT

TECHNICAL FIELD

The present invention relates to a method for cultivation of a genetically-modified plant, and particularly relates to a method for cultivation of a genetically-modified plant transformed so that a desired objective protein is highly expressed, and a method for production of a seed including the desired objective protein.

BACKGROUND ART

Genetic modification technology has been practically applied as a breed improvement method of plants, and genetically-modified farm crops such as soybeans, maize, rapeseeds, cottons and potatoes to which functions such as herbicide resistance and harmful insect resistance had been added were developed and have been already in practical use. Further in recent years, research and development in which a useful foreign gene is introduced into a chromosome of a plant to produce a genetically-modified plant have been carried forward as a procedure to produce a functional protein or peptide for pharmaceuticals or test agents. Functional components produced by using the genetically-modified plant include not only a protein and a peptide that are a product of the introduced gene but also a product by a reaction of an introduced enzyme protein. There are many advantages in production of the functional components in a plant. The advantages include reduction of cost compared with an animal transgenic system, easy adjustment of the production scale depending on a market scale, and no possibility of contamination with a pathogen derived from an animal such as virus and prion.

As for a technology of producing efficiently functional components in a plant, for example, a method of utilizing a promoter specific for tissue in which a functional component is accumulated for genetic modification in order to control a stage, a site, and an amount of expression of a functional component has been disclosed (e.g., see Patent Document 1).

Patent Document 1: JP 2007-306941 A

DISCLOSURE OF INVENTION

Problem to be Solved by the Invention

However, when technology of highly accumulating a functional component in a plant body is developed, the technology of the above Patent Document 1 merely utilizes a promoter that highly expresses the functional component for genetic modification, and there is still room to improve in term of productivity of functional components.

In the light of the above circumstance, it is an object of the present invention to provide a method capable of producing a desired functional component with a higher yield by using a genetically-modified plant transformed so that the desired functional component is expressed. Any protein or peptide desired to be highly expressed in the genetically-modified plant is referred to as an "objective protein" herein in some cases.

Means for Solving Problem

As a result of an extensive study, the present inventors succeeded in detecting RNA and a seed storage protein that increase their expressed amounts under a predetermined high nitrogen-cultivation condition. Further, the present inventors succeeded in isolating a promoter that regulates expression of RNA and the seed storage protein obtained by this detection method and making a genetically-modified plant in which this promoter and a polynucleotide encoding an objective protein downstream thereof had been introduced, as well as succeeded in producing the objective protein with a high yield by cultivating such a genetically-modified plant under a predetermined high nitrogen cultivation condition. The present invention provides a method for cultivation of a following genetically-modified plant and a method for production of a seed. A term "cultivation of a plant" may be replaced by "production of a plant" herein.

[1] A method for cultivation of a genetically-modified plant comprising: cultivating the genetically-modified plant in a medium, wherein the genetically-modified plant is transformed by introducing an expression vector comprising, a promoter that regulates expression of RNA expressed in a seed that satisfies Formula (1):

$$V/W>1.0 \quad (1)$$

wherein V is an amount of RNA contained in the seed of a predetermined plant when the plant is cultivated in a medium adjusted so that nitrate nitrogen is 70 mg/L to 750 mg/L and/or ammonium nitrogen is 70 mg/L to 750 mg/L for a definite period in a period from 30 days before an expected flowering date to a date on or before flowering, and W is an amount of RNA contained in a seed of the plant when the plant is cultivated in a medium adjusted so that nitrogen is 0 mg/L to 50 mg/L for a definite period in a period from 30 days before the expected flowering date to the date on or before flowering; and a polynucleotide located downstream of the promoter and encoding an objective protein, and wherein the medium is adjusted so that nitrate nitrogen is 70 mg/L to 750 mg/L and/or ammonium nitrogen is 70 mg/L to 750 mg/L for a definite period in a period from 30 days before an expected flowering date to a date on or before flowering of the genetically-modified plant.

[2] A method for cultivation of a genetically-modified plant comprising: cultivating the genetically-modified plant in a medium, wherein the genetically-modified plant is transformed by introducing an expression vector comprising, a promoter that regulates expression of a seed storage protein that satisfies Formula (2):

$$X/Y>1.0 \quad (2),$$

wherein X is an amount of the seed storage protein contained in a seed of a predetermined plant when the plant is cultivated in a medium adjusted so that a nitrate nitrogen content is 70 mg/L to 750 mg/L and/or ammonium nitrogen is 70 mg/L to 750 mg/L for a definite period in a period from 30 days before an expected flowering date to a date on or before flowering, and Y is an amount of the seed storage protein contained in a seed of the plant when the plant is cultivated in a medium adjusted so that nitrogen is 0 mg/L to 50 mg/L for a definite period in a period from 30 days before the expected flowering date to the date on or before flowering; and a polynucleotide located downstream of the promoter and encoding an objective protein, and wherein the medium is adjusted so that nitrate nitrogen is 70 mg/L to 750 mg/L and/or ammonium nitrogen is 70 mg/L to 750 mg/L for a definite period in a period from 30 days before an expected flowering date to a date on or before flowering of the genetically-modified plant.

[3] The method for cultivation of a genetically-modified plant according to the above [1] and [2], wherein the predetermined plant and the genetically-modified plant are the same species.

[4] The method for cultivation of a genetically-modified plant according to the above [3], wherein the predetermined plant is a poaceous plant and the genetically-modified plant is a poaceous plant.

[5] The method for cultivation of a genetically-modified plant according to the above [4], wherein the promoter is a promoter that regulates the expression of the seed storage protein selected from the group consisting of glutelin, globulin and prolamin.

[6] The method for cultivation of a genetically-modified plant according to any one of the above [1] to [5], wherein the cultivation of said genetically-modified plant is performed by water cultivation.

[7] A method for production of a seed comprising cultivating the genetically-modified plant according to any one of the above [1] to [6] and collecting the seed.

[8] The method for production of a seed according to the above [7], wherein the plant is a rice plant and the seed is a rice seed.

Effect of the Invention

According to the present invention, an objective protein can be produced with a high yield.

BEST MODES FOR CARRYING OUT THE INVENTION

Figures 1, 2:
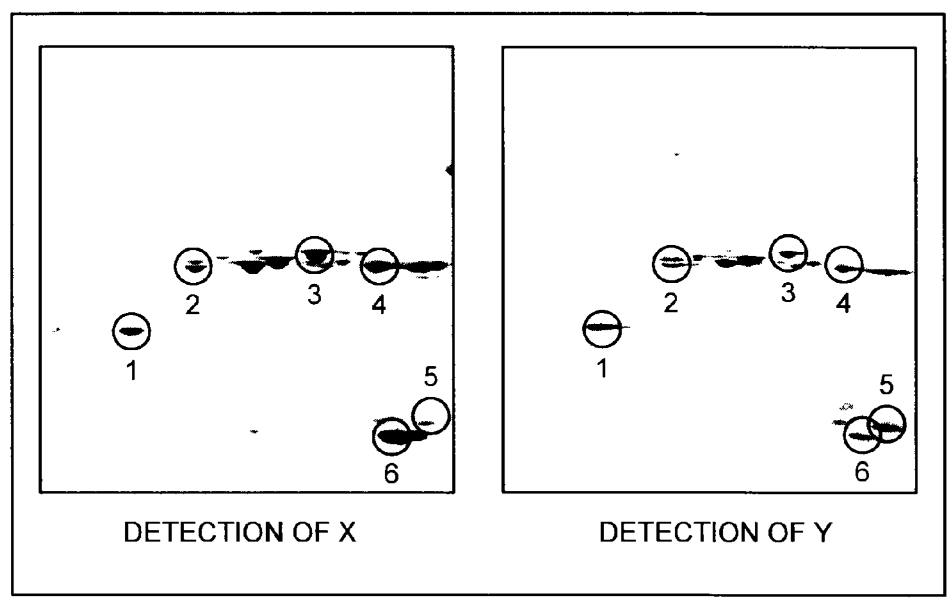
FIG. 1 depicts a view of an outline of schedule including cultivation management.
FIG. 2 depicts a view of an image analysis result of two dimensional gel electrophoresis of the protein.

In a method for cultivation of a genetically-modified plant of the present invention, the genetically-modified plant comprising a predetermined feature is cultivated under a predetermined condition. Embodiments of the present invention are described in detail as follows:

1. Method for making the genetically-modified plant;

2. Method for cultivation of the genetically-modified plant and method for production of its seed.

1. Method for Making a Genetically-Modified Plant

The method for making a genetically-modified plant used in the present invention can be divided into following two steps as the outline, Step A and Step B. Step A is the step of detecting RNA and a seed storage protein that are highly expressed under a high nitrogen cultivation condition in a predetermined plant. Step B is the step of making a genetically-modified plant by isolating a promoter that regulates expression of RNA and the seed storage protein that are highly expressed under a high-nitrogen cultivation condition, and preparing an expression vector comprising a polynucleotide encoding an objective protein, and then introducing the expression vector into a host plant cell.

Step A: Detection of RNA

In the detection of RNA in Step A, a plant is cultivated under at least two different nitrogen conditions, and RNA that is highly expressed in a certain plant species under a predetermined high nitrogen-cultivation condition is detected by using a difference of RNA contents as the indicator.

In an embodiment of method of detecting RNA in Step A, RNA that satisfies the following Formula (1) is detected.

$$V/W>1.0 \quad (1)$$

In Formula (1), V is an amount of RNA contained in a seed of a predetermined plant when the plant is cultivated in a medium adjusted so that nitrate nitrogen is 70 mg/L to 750 mg/L and/or ammonium nitrogen is 70 mg/L to 750 mg/L for a definite period in a period from 30 days before an expected flowering date to a date on or before flowering. W is an amount of RNA contained in a seed of the plant when the plant is cultivated in a medium adjusted so that nitrogen is 0 mg/L to 50 mg/L for a definite period in a period from 30 days before the expected flowering date to the date on or before flowering.

RNA satisfying the above Formula (1) is the RNA that is highly expressed under a high nitrogen-cultivation condition. An expression regulatory region such as a promoter that facilitates expression of RNA under a high nitrogen-cultivation condition may be collected from the information of the detected RNA.

<Step A: Detection of Seed Storage Protein>

In the detection of a seed storage protein in Step A, a plant is cultivated under at least two different nitrogen conditions, and a seed storage protein that is highly expressed in certain plant species under a predetermined high nitrogen-cultivation condition is detected by using a difference of accumulated amounts of the seed storage protein as the indicator.

In an embodiment of method of detecting the seed storage protein in Step A, the seed storage protein that satisfies the following Formula (2) is detected.

$$X/Y>1.0 \quad (2)$$

In Formula (2), X is an amount of the seed storage protein contained in a seed of a predetermined plant when the plant is cultivated in a medium adjusted so that a nitrate nitrogen content is 70 mg/L to 750 mg/L and/or ammonium nitrogen is 70 mg/L to 750 mg/L for a definite period in a period from 30 days before an expected flowering date to a date on or before flowering. Y is an amount of the seed storage protein contained in a seed of the plant when the plant is cultivated in a medium adjusted so that nitrogen is 0 mg/L to 50 mg/L for a definite period in a period from 30 days before the expected flowering date to the date on or before flowering.

A seed storage protein satisfying the above Formula (2) is the seed storage protein that is highly expressed under a high nitrogen-cultivation condition. An expression regulatory region such as a promoter that facilitates expression of the seed storage protein under a high nitrogen cultivation-condition may be collected from the information of the detected seed storage protein.

<Plant as Subject to be Tested>

The "predetermined plant" in Step A means a plant as a subject to be tested. A plant as the subject to be tested in Step A is a plant to search a promoter that facilitates expression of RNA and a seed storage protein, and may be appropriately selected in consideration of conditions such as the type of the genetically-modified plant to be made later. The plant involved in the detection of RNA and the seed storage protein is not particularly limited as long as a seed is formed. Examples may typically include: dicotyledonous plants such as tobacco, rapeseed, and soybean; and monocotyledonous plants such as grain crops including rice, maize, barley and wheat, and asparagus. Among them, the rice is a suitable plant because ability of accumulating a protein in the seed is high and storage stability of the seed is good.

<Cultivation Condition>

The plant as the subject to be tested is cultivated under at least two different nitrogen conditions. As a preferable embodiment, cultivation is performed under First cultivation condition and Second cultivation condition. First cultivation condition is a condition in which a concentration of supplied nitrogen is high. On the other hand, Second cultivation condition is a condition in which a concentration of nitrogen is relatively lower than in First cultivation condition. Specifically, the following conditions may be included.

First cultivation condition: a plant is cultivated in a medium adjusted so that nitrate nitrogen is 50 mg/L to 750 mg/L and/or ammonium nitrogen is 50 mg/L to 750 mg/L, for a definite period in a period from 30 days before an expected flowering date to a date on or before flowering.

Second cultivation condition: a plant is cultivated in a medium adjusted so that nitrogen is 0 mg/L to 50 mg/L, for a definite period in a period from 30 days before an expected flowering date to a date on or before flowering.

The nitrogen condition in a medium opens from a time point of 30 days before an expected flowering date. The expected flowering date varies depending on a plant, and a time point of the expected flowering date in cultivated crops has been studied in every plant. For example, in case of rice plants, 30 days before the expected flowering date corresponds to a panicle formation stage.

The nitrogen condition in a medium is adjusted for a definite period in a period from between 30 days before an expected flowering date and a flowering date. It is important to expose a plant to a high nitrogen condition at least once during the period and give a definite physiological stimulation to the plant. That is, the "definite period" referred to here may be a period enough to give the definite physiological stimulation to the plant. The period of the high nitrogen condition may be appropriately adjusted depending on conditions such as a growing state and a type of a plant. Although conditions such as the growing state and the type of a plant may cause differences, it is preferable to cultivate a plant under a high nitrogen condition preferably for about one week, more preferably for about two weeks. It is also preferable to place a plant under a high nitrogen condition for a definite period immediately after passing 30 days before an expected flowering date and/or just before a flowering date. In case of rice plants, the plant may be placed under a high nitrogen-cultivation condition throughout the period from 30 days before an expected flowering date to a flowering date.

In cultivation of the plant, the nitrogen concentration of a medium is easily changed due to factors such as absorption of nutrients by the plant and an ability of a medium to retain fertilizers. In the above First and Second cultivation conditions, it is not always necessary to keep the nitrogen concentration constant in the medium, and fertilizer application may be conducted so that the nitrogen concentration falls in the above concentration range. Timing and a frequency of the fertilizer application and a concentration of the fertilizer may be appropriately adjusted as long as the nitrogen concentration in a medium is controlled as described above.

Measurement of the nitrogen concentration in a medium may be carried out, depending on the type of the medium, according to general soil analysis or fertilizer analysis methods such as the fertilizer analysis method determined by the Ministry of Agriculture, Forestry and Fisheries, and using a nitrate ion meter and an ammonia nitrogen meter.

Nitrate nitrogen refers to a nitrogen component present in a form of oxidized nitrogen such as nitrate ion. Usually, nitrate nitrogen is present in the form of a nitrate salt obtained by binding a metal to nitrate ion in the form of $NO_3^-$.

Ammonium nitrogen refers to a nitrogen component present in a form of an ammonium salt among the nitrogen components.

Adjustment of a nitrogen source in a medium is conducted so that a nitrate nitrogen content in the medium is 70 mg/L to 750 mg/L and/or an ammonium nitrogen content in the medium is 70 mg/L to 750 mg/L. That is, both nitrate nitrogen and ammonium nitrogen may be used as the nitrogen sources and their concentrations may be adjusted, respectively, or either one may be used as the nitrogen source and its concentration may be adjusted. Preferably, the both are used as the nitrogen sources. A ratio of contents of the nitrate nitrogen to the ammonium nitrogen is, for example, 750:0 to 0:750, preferably 100:1 to 1:100 more preferably 30:1 to 1:30, more preferably 10:1 to 1:10, and still more preferably about 3:1 to 1:3.

A content of the nitrate nitrogen in First cultivation condition is 70 mg/L to 750 mg/L, preferably 100 mg/L to 700 mg/L and more preferably 150 mg/L to 700 mg/L. When the content of nitrate nitrogen is adjusted to 70 mg/L or less, the content of a seed storage protein reduces and it tends to be difficult to obtain an adequate indicator for comparing with that of the Second cultivation condition. On the other hand, when the content of nitrate nitrogen is adjusted to 750 mg/L or more, root rot easily occurs and causes poor growth.

A content of the ammonium nitrogen in First cultivation condition is 70 mg/L to 750 mg/L, preferably 100 mg/L to 700 mg/L and more preferably 150 mg/L to 700 mg/L. When the content of ammonium nitrogen is adjusted to 70 mg/L or less, the content of a seed storage protein reduces and it tends to be difficult to obtain an adequate indicator for comparing with that of Second cultivation condition. On the other hand, when the content of ammonium nitrogen is adjusted to 750 mg/L or more, the root rot easily occurs and causes the poor growth.

Except applying the predetermined different conditions of nitrogen as described above, fertilizer application suitable for a plant may be conducted depending on the type of a plant for cultivation. Other components contained in the medium may include phosphorous, potassium, manganese, boron, iron, calcium, copper, zinc and magnesium.

The cultivation of a plant may include a water cultivation and a soil cultivation. The soil cultivation has an advantage that considerable fluctuation of fertilizer components can be prevented because the fertilizer components are absorbed in the soil; on the flip side, the fertilizer components that can be utilized by the plant is decreased. On the other hand, the water cultivation has a feature that all of the fertilizer components in a medium can be utilized by a plant. In a selection way for plants of the present invention, a fertilizer application needs to be conducted so that a nitrogen content is adjusted under the predetermined condition, the water cultivation is more preferable in terms of easy adjustment of the fertilizer components.

<Measurement of RNA Contained in Seed and Determination of RNA>

An amount of RNA contained in a seed obtained from each plant cultivated under First and Second cultivation condition is measured. The amount of RNA contained in the seed obtained from the plant cultivated under First cultivation condition is designated as V. The amount of RNA contained in the seed obtained from the plant cultivated under Second cultivation condition is designated as W.

The above RNA amounts V and W can be obtained by utilizing various publicly known RNA detection methods. As one embodiment, for example, RNA amount may be measured by utilizing a microarray as follows. First, RNA is extracted from a seed, and fluorescence-labeled cDNA is synthesized and then hybridized with DNA fragments on the microarray. A microarray image is imported using a scanner, and then fluorescence intensity in each spot was calculated using analysis software. The RNA amount can be obtained from the calculated spot intensity. As the seed from which RNA is extracted, a seed from 15 days to 25 days after flowering is preferable because RNA is actively synthesized.

RNA subjected to the measurement may be RNA contained in a seed. RNA for obtaining a V/W value may include, for example in case of rice plants, AK101497 (SEQ ID NO:5), AK120826, AJ002893 (SEQ ID NO:6), 0s05g0329200 (SEQ ID NO:7), AK107271 (glutelin A-3) (SEQ ID NO:8), AK102194 (SEQ ID NO:9), AK120697 (SEQ ID NO:10), AK067141 (SEQ ID NO:11), AK065009 (SEQ ID NO:12), AF017360 (SEQ ID NO:13), AK071205 (SEQ ID NO:14), AK059164 (SEQ ID NO:15), AK107238 (SEQ ID NO:16), AB016505 (SEQ ID NO:17), AK099086 (SEQ ID NO:18), AY166458 (SEQ ID NO:19), AY987390 (glutelin B-2) (SEQ ID NO:20), AK107314 (SEQ ID NO:21), X15833 (SEQ ID NO:22), AY196923 (glutelin B-5) (SEQ ID NO:30), AK061894 (SEQ ID NO:23), AK107343 (glutelin 8-1) (SEQ ID NO:24), AK063995 (SEQ ID NO:25), J100041C23, AK108210 (SEQ ID NO:26), J090009107 (SEQ ID NO:27), AK065456 (SEQ ID NO:28), AK107314, AK107633 (SEQ ID NO:29), U43530 (SEQ ID NO:31), AK064310 (SEQ ID NO:32), AK064485 (SEQ ID NO:33), AK101309 (SEQ ID NO:34), AK107983 (SEQ ID NO:35), AK099918 (SEQ ID NO:36), AK100306 (SEQ ID NO:37), X83434 (SEQ ID NO:38), AK070414 (SEQ ID NO:39), AK103220 (SEQ ID NO:40), AK121856 (SEQ ID NO:41), AK062758 (SEQ ID NO:42), AK103306 (SEQ ID NO:43), AK061207 (SEQ ID NO:44), AK068266 (SEQ ID NO:45), Os06g0598500 (SEQ ID NO:46), AK119900 (SEQ ID NO:47), L19598 (SEQ ID NO:48), AK070851 (SEQ ID NO:49), Os01g0840300 (SEQ ID NO:50), AK059805 (SEQ 5 ID NO:51), AK106244 (SEQ ID NO:52), AK108127 (SEQ ID NO:53), AK108230, AK061237 (SEQ ID NO:54), AK062517 (SEQ ID NO:55), AK065259 (SEQ ID NO:56), AK065604 (SEQ ID NO:57), AK106964 (SEQ ID NO:58), AK060983 (SEQ ID NO:59), J075074G08, AK099719 (SEQ ID NO:60) (GenBank Accession No.), glutelin, globulin, and prolamin.

Based on the RNA amounts V and W, RNA that satisfies the following Formula (1):

$$V/W>1.0 \quad (1)$$

is selected. Satisfying Formula (1) has a high probability that such selected RNA is RNA of which expression is increased under a predetermined high nitrogen cultivation condition. The promoter of DNA encoding such RNA has a high probability that the promoter facilitates the expression of a protein under the high nitrogen cultivation condition. The V/W value is preferably 1.25 or more, more preferably 1.5 or more and still more preferably 2.0 or more. On the other hand, when the V/W value is 1 or less, the effect of highly producing an objective protein can not be expected even if the amount of nitrogen in a medium is increased.

<Measurement of Content of Seed Storage Protein and Determination of Seed Storage Protein>

A content of a seed storage protein stored in the seed obtained from each plant cultivated under First and Second cultivation condition is measured. The content of the seed storage protein stored in the seed obtained from the plant cultivated under First cultivation condition is designated as X. The content of the seed storage protein stored in the seed obtained from the plant cultivated under Second cultivation condition is designated as Y.

The above contents X and Y of the seed storage proteins may be obtained by utilizing various publicly known protein detection methods. As one embodiment, for example, a content of the protein may be measured by utilizing an electrophoresis method as follows. First, each seed storage protein is separated into a single spot on a gel by a two dimensional gel electrophoresis method. Subsequently, information on the gel is exchanged to an image file using the scanner, and then the fluorescence intensity of each spot is calculated using analysis software. A content of the protein can be obtained from the calculated spot intensity. As the seed from which a protein is extracted, a seed after 30 days, preferably 45 days after flowering is desirable because the seed storage protein is sufficiently accumulated.

The protein subjected to the measurement may be any seed storage protein. The seed storage protein for obtaining an X/Y value may include, for example in case of rice plants, glutelin, globulin and prolamin proteins, and more specifically may include glutelin B-1, glutelin B-2, glutelin B-5, glutelin A-3, globulin and 13 kDa prolamin.

Based on the contents of the seed storage protein X and Y, a seed storage protein that satisfies the following Formula (2):

$$X/Y>1.0 \quad (2)$$

is selected. Satisfying Formula (2) has a high probability that the selected seed storage protein is a seed storage protein of which the expression is increased under a predetermined high nitrogen cultivation condition. The promoter of such a seed storage protein has a high probability that the promoter facilitates the expression of a protein under a high nitrogen cultivation condition. The X/Y value is preferably 1.5 or more, and more preferably 2.0 or more. On the other hand, when the X/Y value is 1 or less, the effect of highly producing an objective protein can not be expected even if the amount of nitrogen in a medium is increased.

As described above, RNA and a seed storage protein, the expression of which are increased under a predetermined high nitrogen cultivation condition, can be selected. A promoter of the selected RNA and seed storage protein facilitates expression of the protein under a high nitrogen cultivation condition. Such a promoter can be a material for a genetically-modified plant in which an objective protein is highly expressed under a predetermined high nitrogen cultivation condition by introducing the promoter into the genetically-modified plant described below.

<Step B: Preparation of Transformant>

In Step B, first, a promoter regulating expression of RNA and a seed storage protein that are highly expressed under a high nitrogen cultivation condition is isolated. Such a promoter may be isolated from the plant that is the subject to be tested in the above Step A and in which RNA and the seed storage protein that are highly expressed under the high nitrogen cultivation condition have been detected. The promoter may be isolated from an expression regulatory region located upstream of the nucleic acid encoding RNA and a seed storage protein.

Various RNA(s) and seed storage proteins and various nucleic acid sequences encoding them are known, shown in the known databases and the like. Also, a location and sequence of the promoter that regulates expression of RNA and a seed storage protein are publicly known in some cases. In the present invention, a promoter may be identified by utilizing publicly known sequences, or a nucleic acid sequence encoding the RNA and the seed storage protein selected in Step A is searched and the nucleic acid sequence upstream thereof may be used as the promoter. The promoter may be identified by using the sequence commonly observed in the promoters such as TATA box, CCAAT box or a GC-rich sequence located upstream of a transcription region as a clue, or the promoter may be identified by ligating the nucleic acid encoding a known protein to a nucleic acid sequence presumed to be the promoter and measuring expression of the known protein.

<Construction of Expression Vector>

An expression vector for expressing an objective protein is constructed. The expression vector comprises at least a promoter identified as above and a nucleic acid encoding the objective protein. In addition, the others such as a terminator, a publicly known expression promoting sequence, and a marker sequence may be inserted in the expression vector.

The promoter identified as above is prepared so as to be incorporated in a vector. The promoter may be isolated from a cell of a selected plant, or may be synthesized by identifying its sequence. The vector suitable for the introduction into a plant cell is preferable. A publicly known vector or a commercially available vector may be utilized.

An objective protein may be any protein or peptide scheduled to be highly expressed in a seed. One preferable embodiment may include a so-called functional protein. The functional protein means a protein useful for human beings, e.g., antimicrobial components and enzymes. A nucleic acid encoding the objective protein may be obtained by a technique such as cloning of cDNA or genomic DNA. Also, if its DNA sequence has been previously demonstrated, the nucleic acid may be obtained by chemically synthesizing the sequence. Further, even when the DNA sequence is not demonstrated, if an amino acid sequence has been demonstrated, the DNA sequence deduced from the amino acid sequence may be synthesized chemically.

The expression vector may be made by arranging the nucleic acid encoding an objective protein downstream of the promoter and inserting this in a vector. A way to cleave or ligate a nucleic acid fragment at a predetermined position may be performed by utilizing publicly known restriction enzymes.

Figure 3:
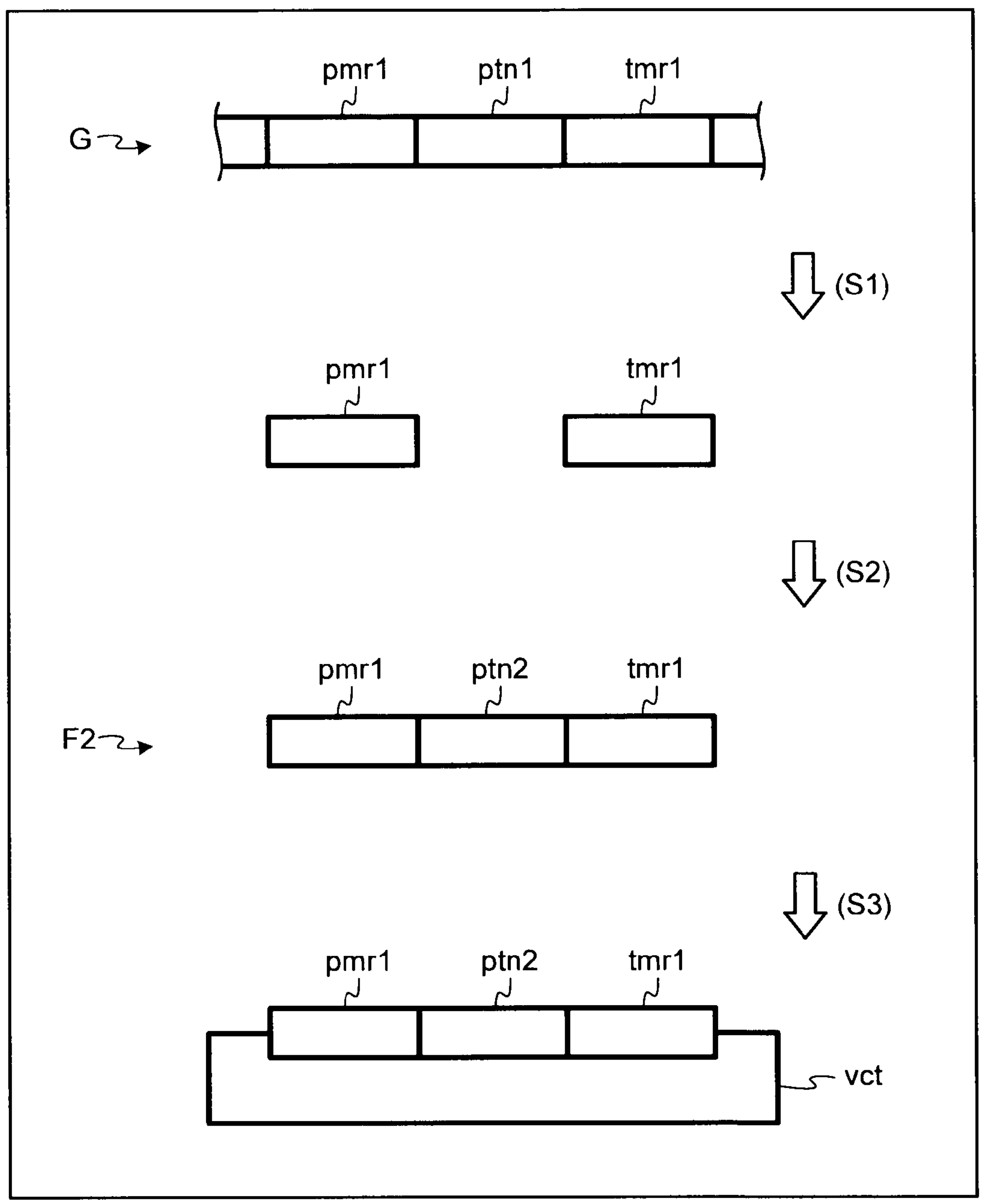
FIG. 3 depicts a schematic view of a process of construction for an expression vector.

One embodiment for construction of a vector is described with reference to FIG. 3.

First, as the step (S1), a promoter (pmr1) contained in a chromosome G contained in the cell of the plant selected in Step A is isolated. The promoter (pmr1) together with a terminator (tmr1) constitutes a region that regulates the expression of a protein (ptn1). The promoter (pmr1) and the terminator (tmr1) are amplified from this chromosome by the technique such as PCR. PCR primers may be appropriately designed based on the sequences before and after the promoter (pmr1) and the terminator (tmr1), which sandwich each of the promoter (pmr1) and the terminator (tmr1).

Subsequently, as the step (S2), a nucleic acid fragment (F2) in which the nucleic acid (ptn2) encoding an objective protein is sandwiched between the amplified and obtained promoter (pmr1) and terminator (tmr1) is constructed.

Further, as the step (S3), the nucleic acid fragment (F2) obtained in the step (S2) is incorporated in a plasmid vector (vct). Thus, the expression vector may be constructed.

<Plant as Host>

As a host to which the vector prepared as above is introduced, a cell of a plant that produces an objective protein as the genetically-modified plant is used. The type of the plant as the host is not particularly limited as long as the above promoter is recognized and the objective protein can be expressed. A suitable plant as the host may be appropriately selected in terms of production of an objective protein in consideration of conditions such as easiness of cultivation management, an environment of a cultivation place, a growing period, easiness of harvest, as well as nature, a size and a yield of the seed. An adverse effect on a gene expression system is easily avoided by assigning a host the same kind of plant as the plant from which the promoter facilitating expression of RNA and the seed storage protein, obtained in the above, is derived. Thus, one preferable embodiment may include a form in which the same plant species from which the promoter is derived is used as the host.

Examples of a plant as the host, that is, the plant scheduled to be cultivated as the genetically-modified plant may include: dicotyledonous plants such as tobacco, rapeseed and soybean; and monocotyledonous such as grain crops including rice plant, maize, barley and wheat, and asparagus. Among them, the rice plant is a suitable plant because an ability to accumulate a protein in a seed is high and storage stability of the seed is good.

<Introduction of Constructed Expression Vector into Plant Cell>

Subsequently, a transformed cell of a plant is made by using the constructed expression vector. A plant cell to be transformed as the host is preferably the plant that can be directly reproduced and can be cultivated in a large amount as the genetically-modified plant, in terms of simplification of steps.

As a method for introducing the constructed expression vector into the plant cell, for example, physical/chemical methods such as a microinjection method, an electroporation method, a polyethylene glycol method, a fusion method and a high speed ballistic penetration method may be used as the method for directly introducing into the plant or animal cell (I. Potrykus, Annu. Rev. Plant Physiol. Plant Mol. Biol., 42: 205, 1991). An indirect introduction method by introducing into the plant cell through virus or bacterium that infects a plant may also be used (I. Potrykus, Annu. Rev. Plant Physiol. Plant Mol. Biol., 42: 205, 1991). Viruses usable for this may include cauliflower mosaic virus, Gemini virus, tobacco mosaic virus and brome mosaic virus, and bacteria usable for this may include *Agrobacterium tumefaciens* and *Agrobacterium rhizogenes.*

<Redifferentiation of Transformant>

Subsequently, a genetically-modified tissue or a genetically-modified individual is cultured from the plant cell in which a foreign gene has been introduced by the above method. The cell having the introduced gene can be grown and redifferentiated by a standard method to culture the genetically-modified tissue or the genetically-modified individual, with appropriately performing a selection using expression of a specific character by the objective gene or a selection marker gene or disappearance of a specific character by deletion of the gene as the indicator. The seed is collected from the redifferentiated and obtained plant, and the genetically-modified body can be reproduced by utilizing the obtained seed.

Although being not altogether clear, a reason why productivity of the objective protein is enhanced by the present invention is estimated as follows. It may be considered that the genes involved in amino acid synthesis can be activated by supplying excessive nitrogen as a raw material of the amino acid synthesis during the generative growth phase before flowering. It may be considered that the genes involved in protein synthesis are activated by the effects of the amino acids accumulated in the plant body and the activated genes involved in amino acid synthesis during a grain-filling phase of the seed after the flowering phase. Further, it is considered that the objective protein is more efficiently produced by utilizing the promoter region of a more highly activated gene involved in protein synthesis compared with the other genes involved in protein synthesis.

2. Method for Cultivation of Genetically-Modified Plant and Method for Production of Seed In a method for cultivation of genetically-modified plant of the present invention, the genetically-modified plant that can be prepared by above "1. Method for making genetically-modified plant" is cultivated under a predetermined condition. Specific embodiments are described later, and it is not always necessary to repeat above Step A: detection of RNA and seed storage protein and Step B: preparation of transformant, after once obtaining a genetically-modified plant transformed so that an objective protein is highly expressed under a high nitrogen cultivation condition by above "1. Method for making genetically-modified plant". That is, after once obtaining the genetically-modified plant transformed so that an objective protein is highly expressed under a high nitrogen cultivation condition, the genetically-modified plant may be maintained according to an ordinary breeding method of the plant species, and the plant may be cultivated repeatedly.

<Step C: Cultivation of Genetically-Modified Plant>

The genetically-modified plant made by above "1. Method for making genetically-modified plant" is cultivated in a medium adjusted so that nitrate nitrogen is 70 mg/L to 750 mg/L and/or ammonium nitrogen is 70 mg/L to 750 mg/L for a definite period in a period from 30 days before an expected flowering date to the flowering date.

Step C is the step of cultivating the genetically-modified plant under a predetermined high nitrogen cultivation condition. Above "1. Method for making genetically-modified plant" except only the part of "the second cultivation condition" (i.e., the case of low nitrogen condition) may be applied in the same manner to the embodiment of the cultivation condition in Step C. In other words, as an embodiment of the cultivation condition in Step C, the nitrogen condition as the "first cultivation condition" in above "1. Method for making genetically-modified plant" is applied in the same manner, and the other conditions for the cultivation: a form of a starting time of the predetermined nitrogen condition and its definite period, a form for controlling the nitrogen concentration in a medium, a form for measuring the nitrogen concentration in a medium, a form for adjusting the nitrogen source in a medium, a form for managing fertilizer application, and a form of the water cultivation or the soil cultivation may be applied in the same manner as in the embodiments described in the <cultivation condition> in above "1. Method for making genetically-modified plant". The specific cultivation conditions other than the nitrogen condition may be appropriately adjusted depending on the type of a plant for the genetically-modified plant.

<Method for Production of Seed>

The genetically-modified plant cultivated in the present invention may be utilized directly or by ingesting the introduced objective protein in a separated and purified form.

When the genetically-modified plant is a seed plant, the method for cultivation of the genetically-modified plant of the present invention is also the method for production of the seed. The seed plant may include poaceous plants, more preferably the rice plant because storage stability of the seed protein is high.

In case of producing the seed, when the seed is formed and reaches a predetermined maturity, the seed is collected. The collection referred to here is synonymous with harvest referred to fields of agriculture and gardening. Therefore, the collection includes not only separating a seed itself but also collecting a plant body including the seed from a cultivation place.

In the seed produced by the method for producing a seed plant of the present invention, an objective protein is highly expressed. The objective protein may be purified from the seed, or the seed itself may be directly utilized. When the objective protein is a functional protein that is ingestible by human, the seed may be simply ingested directly or by cooking it.

The promoter that facilitates high expression under a high nitrogen condition is found and the seed (or the cultivar) that produces a genetically-modified body in which the promoter has been incorporated is stored, thereby in the future, it is not necessary to repeat the detection of RNA and a seed storage protein and the production of the genetically-modified plant based on it every time. For example, once a promoter that regulates expression of RNA and the seed storage protein that can be highly expressed under a high nitrogen cultivation condition is identified for a certain plant, it is not necessary to perform the detection of RNA and a seed storage protein in the above Step A every time, and the genetically-modified plant may be made based on the finding.

For example, in case of isolating a promoter from rice plants, the isolated promoters may include, preferably promoters of AK101497, AK120826, AJ002893, Os05g0329200, AK107271 (glutelin A-3), AK102194, AK120697, AK067141, AK065009, AF017360, AK071205, AK059164, AK107238, AB016505, AK099086, AY166458, AY987390 (glutelin B-2), AK107314, X15833, AY196923 (glutelin B-5), AK061894, AK107343 (glutelin B-1), AK063995, J100041C23, J090009107, AK065456, AK107314, AK107633, U43530, AK064310, AK064485, AK101309, AK107983, AK099918, AK100306, X83434, AK070414, AK103220, AK121856, AK062758, AK103306, AK061207, AK068266, Os06g0598500, AK119900, L19598, AK070851, Os01g0840300, AK059805, AK106244, AK108127, AK108230, AK061237, AK062517, AK065259, AK065604, AK106964, AK060983, J075074G08, AK099719 (GenBank Accession No.), glutelin, globulin and prolamin. More preferably, the promoter may include the promoter of glutelin B-1, glutelin B-2, glutelin B-5, glutelin A-3, globulin or 13 kDa prolamin. Still more preferably, the promoter of glutelin B-1 or glutelin B-5 may be included. These promoters can facilitate expression of a structural gene present downstream thereof under a high nitrogen cultivation condition. When these promoters are used, the rice plant is suitable as a plant assigned as the host to be transformed. That is, the other embodiment of a method for cultivation of a genetically-modified plant of the present invention may include an embodiment in which a genetically-modified plant transformed is cultivated in a medium, wherein a genetically-modified plant is transformed by introducing an expression vector comprising the promoter that regulates expression of DNA encoding RNA contained in the seed satisfying V/W>1.0 and the promoter that regulates expression of the seed storage protein selected from glutelin, globulin and prolamin and the polynucleotide encoding an objective protein planed to be highly expressed, and wherein, the medium is adjusted so that nitrate nitrogen is 70 mg/L to 750 mg/L and/or ammonium nitrogen is 70 mg/L to 750 mg/L, for a definite period in a period from 30 days before an expected flowering date to the flowering.

Further, once the genetically-modified plant as mentioned above is made, the strain of the genetically-modified plant may be maintained according to the ordinary breeding method for the plant species, and this may be cultivated according to the above step C.

EXAMPLES

The present invention is described in more detail with reference to the following Examples, but the present invention is not limited thereto. In the following Examples, experimental manipulations in more detail for molecular biological techniques were performed according to Molecular Cloning (Sambrook et. al., 1989) or instructions from the manufacturers, except the cases described particularly.

Example 1

1. Cultivation of Plant

Rice was cultivated under First cultivation condition and Second cultivation condition as shown below. An outline of a schedule of the cultivation is shown in FIG. 1. Compositions of a cultivation solution A and a cultivation solution B used are shown in Table 1.

TABLE 1

TABLE FOR CULTIVATION SOLUTION COMPONENTS

| COMPONENT | CULTIVATION SOLUTION A | CULTIVATION SOLUTION B |
|---|---|---|
| | CONTENT [mg/L] | |
| $KNO_3$ | 38.9 | 621.8 |
| $NH_4NO_3$ | 21.8 | 349.5 |
| $(NH_4)_2 \cdot SO_4$ | 8.3 | 132.7 |
| $Mg(NO_3)_2 \cdot 6H_2O$ | 35.7 | 571.4 |
| $Ca(NO_3)_2 \cdot 4H_2O$ | 47.0 | 752.6 |
| NITRATE NITROGEN [mg/L] | 33 | 600 |
| AMMONIUM NITROGEN [mg/L] | 17 | 200 |

<First Cultivation Condition for Measuring RNA Content V and Seed Storage Protein Content X>

Seeds of Nihonbare, which was one cultivar of the rice plant, were sterilized with hypochlorous acid and ethanol, subsequently spread uniformly in a petri dish in which sterilized water had been added, and cultured at 28° C. for 5 days after shielding light.

A urethane mat impregnated with water was paved in a raising seedling box in a room with artificial sunlight, and the budding seeds were seeded thereon, and cultured under a light condition: ambient temperature 28° C., humidity 50% and 11 hours, and a dark condition: ambient temperature 23° C., humidity 50% and 13 hours, for 15 days.

A cultivation bed of a submerging solution system (supplied from M Hydroponic Research Co., Ltd.) was filled with 100 L of the cultivation solution A (see Table 1), the obtained seedlings were planted one by one, and totally 77 seedlings were planted and cultured under the light condition: ambient temperature 28° C., humidity 50% and 11 hours, and the dark condition: ambient temperature 23° C., humidity 50% and 13 hours, for 45 days.

Additional fertilization was given so that the cultivation solution became the composition of the cultivation solution B, and the plants were cultured under the light condition: ambient temperature 28° C., humidity 50% and 11 hours, and the dark condition: ambient temperature 23° C., humidity 50% and 13 hours, for 45 days, and then the seeds were obtained.

Since the water cultivation was performed as above, a nitrogen concentration in the medium was controlled by controlling the nitrogen concentration in water in the cultivation bed. A nitrate nitrogen concentration was measured using nitrate ion composite electrodes (supplied from DKK-TOA Corporation). An ammonium nitrogen concentration was measured using ammonia composite electrodes (supplied from DKK-TOA Corporation).

<Second Cultivation Condition for Measuring RNA Content W and Seed Storage Protein Content Y>

Seeds of Nihonbare were sterilized with hypochlorous acid and ethanol, subsequently spread uniformly in a petri dish in which sterilized water had been added, and cultured at 28° C. for 5 days after shielding the light.

A urethane mat impregnated with water was paved in the raising seedling box in the room with artificial sunlight, the budding seeds were seeded thereon, and cultured under the light condition: ambient temperature 28° C., humidity 50% and 11 hours, and the dark condition: ambient temperature 23° C., humidity 50% and 13 hours, for 15 days.

A cultivation pot was filled with 5 L of soil containing 50 mg/L of nitrogen, one obtained seedling was planted, and cultured under the light condition: ambient temperature 28° C., humidity 50% and 11 hours, and the dark condition: ambient temperature 23° C., humidity 50% and 13 hours, for 45 days.

The additional fertilization was given so that nitrogen in the soil was 50 mg/L, and the plant was cultured under the light condition: ambient temperature 28° C., humidity 50% and 11 hours, and the dark condition: ambient temperature 23° C., humidity 50% and 13 hours, for 45 days, and then the seeds were obtained.

2. Analysis of RNA

<Preparation of Samples for Microarray>

The seeds obtained by cultivating under the above condition and on the 20th day after flowering were frozen in liquid nitrogen, pulverized in a mortar, treated with Fruit-mate for RNA Purification (purchased from Takara Bio Inc.), and subsequently extracted with RNAiso Plus (purchased from Takara Bio Inc.). Subsequently, the sample was treated with Recombinant DNase I (RNase-free) (purchased from Takara Bio Inc.), and purified using Oligotex™-dT30<Super>mRNA Purification Kit (From Total RNA) (purchased from Takara Bio Inc.), thus obtaining an RNA solution.

Total RNA was adjusted to 800 ng/one sample, and dispensed into each tube so that cyanine 3-CTP dye for labeling was 400 ng and cyanine 5-CTP dye for labeling was 400 ng. Cyanine-labeled cRNA was formed using Low RNA Fluorescent Linear Amplification Kit PLUS for two colors (purchased from Agilent Technologies Inc.), and purified using RNeasy mini kit (purchased from Qiagen).

<Hybridization>

Eight hundred and twenty five ng of cDNA labeled with cyanine 3-CTP dye and 825 ng of cDNA labeled with cyanine 5-CTP dye were dispensed in each tube, treated with Gene Expression Hybridization Kit (purchased from Agilent Technologies Inc.), and filled in rice oligo DNA microarray 4×44K RAP-DB (purchased from Agilent Technologies Inc.) to hybridize them.

<Image Analysis>

An image was scanned using the DNA microarray scanner (supplied by Agilent Technologies Inc.) to digitalize each spot. Further, RNA satisfying V/W>1.0 was detected using the image analysis software of GeneSpring GX (supplied by Agilent Technologies Inc.). Values for spot intensity are shown in Table 2.

TABLE 2

| SPOT INTENSITY | | | | | | | |
|---|---|---|---|---|---|---|---|
| GENBANK ACCESSION No. | V/W | V | W | GENBANK ACCESSION No. | V/W | V | W |
| AK101497 (5) | 1.127 | 91451 | 81143 | AK107343 (24) | 1.427 | 50738 | 35568 |
| AJ002893 (6) | 1.753 | 81314 | 46396 | U43530 (31) | 1.264 | 50377 | 39859 |
| AJ002893 (6) | 1.699 | 77978 | 45898 | AK061894 (23) | 1.212 | 50086 | 41334 |
| Os05g0329200 (7) | 1.177 | 75370 | 64061 | AK064310 (32) | 2.573 | 14139 | 5495 |
| AK107271 (8) | 1.557 | 75252 | 48343 | AK064485 (33) | 2.886 | 10076 | 3491 |
| AK102194 (9) | 1.751 | 74943 | 42797 | AK101309 (34) | 3.056 | 9545 | 3124 |
| AK120697 (10) | 1.215 | 71656 | 58957 | AK107983 (35) | 2.116 | 9180 | 4338 |
| AK067141 (11) | 1.005 | 70527 | 70180 | AK064310 (32) | 2.206 | 8272 | 3750 |
| AK102194 (9) | 1.748 | 69923 | 40007 | AK099918 (36) | 5.833 | 7159 | 1227 |
| AK065009 (12) | 1.116 | 68916 | 61749 | AK100306 (37) | 3.804 | 7106 | 1868 |
| AF017360 (13) | 1.118 | 68870 | 61584 | AK099918 (36) | 6.539 | 6960 | 1064 |
| AK107271 (8) | 1.736 | 68402 | 39408 | X83434 (38) | 2.155 | 5838 | 2709 |
| AK120697 (10) | 1.193 | 66986 | 56154 | AK099918 (36) | 6.427 | 5222 | 812.4 |
| AK102194 (9) | 1.715 | 66926 | 39028 | AK070414 (39) | 2.089 | 5169 | 2474 |
| AK065009 (12) | 1.092 | 65756 | 60201 | AK103220 (40) | 3.165 | 4961 | 1568 |
| AK071205 (14) | 1.014 | 65560 | 64659 | AK121856 (41) | 2.627 | 4631 | 1763 |
| AK059164 (15) | 1.135 | 65268 | 57482 | AK121856 (41) | 2.59 | 4432 | 1711 |
| AK107238 (16) | 1.413 | 64078 | 45359 | AK070414 (39) | 2.044 | 4322 | 2114 |
| AF017360 (13) | 1.006 | 64006 | 63630 | AK062758 (42) | 3.851 | 4153 | 1078 |
| AB016505 (17) | 1.238 | 64000 | 51698 | AK103306 (43) | 2.089 | 3874 | 1855 |
| AK099086 (18) | 1.014 | 62402 | 61556 | AK061207 (44) | 2.257 | 3780 | 1675 |
| AK071205 (14) | 1.088 | 61875 | 56864 | AK068266 (45) | 2.285 | 3746 | 1640 |
| AY166458 (19) | 1.269 | 61323 | 48330 | Os06g059500 (46) | 2.276 | 3662 | 1609 |
| AY987390 (20) | 1.222 | 60449 | 49479 | AK119900 (47) | 2.119 | 3565 | 1683 |
| AK107314 (21) | 1.034 | 59883 | 57936 | L19598 (48) | 2.881 | 3442 | 1195 |
| X15833 (22) | 1.477 | 59854 | 40533 | AK070414 (39) | 2.22 | 3230 | 1455 |
| AK061894 (23) | 1.175 | 59530 | 50670 | AK121856 (41) | 2.66 | 3043 | 1144 |
| AK071205 (14) | 1.046 | 59412 | 56780 | AK070851 (49) | 3.648 | 2948 | 808 |
| AK107343 (24) | 1.469 | 59250 | 40327 | Os01g0840300 (50) | 2.534 | 2705 | 1067 |
| AK107314 (21) | 1.074 | 58790 | 54715 | AK059805 (51) | 2.185 | 2704 | 1237 |
| AK063995 (25) | 1.066 | 58227 | 54628 | AK106244 (52) | 2.16 | 2628 | 1217 |
| AK071205 (14) | 1.059 | 57140 | 53974 | AK108127 (53) | 2.516 | 2569 | 1021 |
| AK102194 (9) | 1.744 | 56990 | 32685 | AK070851 (49) | 3.621 | 2524 | 697.3 |
| J100041C23 | 1.507 | 56290 | 37364 | AK059805 (51) | 2.169 | 2511 | 1157 |
| AK108210 (26) | 1.128 | 55144 | 48904 | AK108230 | 9.596 | 2398 | 249.9 |
| AK102194 (9) | 1.747 | 54892 | 31425 | L19598 (48) | 2.718 | 2389 | 879.2 |
| J090009107 (27) | 1.151 | 54746 | 47583 | AK061237 (54) | 3.027 | 2384 | 787.5 |
| AK067141 (11) | 1.029 | 53508 | 52003 | AK062517 (55) | 5.115 | 2240 | 437.9 |
| AK107314 (21) | 1.025 | 53428 | 52134 | AK059805 (51) | 2.162 | 2228 | 1031 |
| AK065456 (28) | 1.075 | 53355 | 49652 | AK065259 (56) | 2.361 | 2207 | 934.7 |
| AK067141 (11) | 1.024 | 53298 | 52053 | AK065604 (57) | 2.036 | 2123 | 1043 |
| AK107314 (21) | 1.04 | 52587 | 50542 | L19598 (48) | 2.792 | 2107 | 754.7 |
| AK061894 (23) | 1.241 | 52460 | 42255 | AK106964 (58) | 2.882 | 2093 | 726.3 |
| AK061894 (23) | 1.232 | 52324 | 42461 | AK060983 (59) | 2.228 | 2049 | 919.8 |
| AK102194 (9) | 1.908 | 51474 | 26985 | J075074G08 | 2.106 | 2036 | 966.6 |
| AK107633 (29) | 1.006 | 51256 | 50971 | AK099719 (60) | 2.257 | 2034 | 901.2 |
| AY196923 (30) | 1.59 | 16127 | 10160 | | | | |

3. Analysis of Protein

<Preparation of Sample for Two Dimensional Gel>

The seeds obtained by cultivating under the above First and Second cultivation conditions and on the 45th day after flowering were pulverized by a multi beads shocker (Yasui Kikai Corporation) after removing blastodiscs, and then homogenized in an extraction solution containing 8 M urea, 4% (w/v) SDS, 20% (w/v) glycerol and 50 mM phosphate buffer, thus obtaining a protein solution. The obtained protein solution was purified using ReadyPre 2-D Cleanup Kit (purchased from BIO-RAD LABORATORIES, Inc., hereinafter abbreviated as BIO-RAD Inc.), and ReadyStrip 7-10 Buffer (purchased from BIO-RAD Inc.) was added thereto. A total protein concentration was determined using RC DC Protein Assay (purchased from BIO-RAD Inc.).

<Two Dimensional Gel Electrophoresis>

Isoelectric focusing electrophoresis for separation of proteins on the first dimension was performed using PROTEIN IEF cell (purchased from BIO-RAD Inc.) and 7 cm ReadyStrip IPG Strip 3-7NL (purchased from BIO-RAD Inc.). Electrophoresis for the separation of the proteins on the second dimension was performed by equilibrating IPG Strip with equilibration buffer I and equilibration buffer II (purchased from BIO-RAD Inc.) and using PROTEIN cell (purchased from BIO-RAD Inc.) and 10-20% resolving Ready Gel Precast Gel (purchased from BIO-RAD Inc.). The samples were electrophoresed with molecular weight markers and isoelectric point calibration markers in order to calculate the molecular weights and the isoelectric points of protein spots upon image analysis. The gel immediately after performing the two dimensional SDS-PAGE was immersed in a fixation solution containing 40% ethanol and 10% acetic acid for 2 hours, and treated with Flamingo Gelstain (purchased from BIO-RAD Inc.).

<Image Analysis of Two Dimensional Gel>

The treated gel was digitalized using Pharos FX Molecular Imager (purchased from BIO-RAD Inc.). Spot positions of 6 types of the seed storage proteins were identified and the spot intensity was measured using Quantity One and PDQuest (purchased from BIO-RAD Inc.). Six types of the seed storage proteins were globulin, glutelin, glutelin B-5, glutelin B-1, 10 kDa prolamin and 13 kDa prolamin. An image analysis view of the two dimensional gel and the values of the spot intensity are shown in FIG. 2 and Table 3, respectively.

TABLE 3

SPOT INTENSITY

| | | SPOT No. | | | | | |
|---|---|---|---|---|---|---|---|
| | | 1 | 2 | 3 | 4 | 5 | 6 |
| PROMOTER | | GLOBULIN | GLUTELIN | GLUTELIN B-5 | GLUTELIN B-1 | 10 KDa PROLAMIN | 13 KDa PROLAMIN |
| SPOT | X | 8338 | 4530 | 7902 | 9159 | 1521 | 16784 |
| INTENSITY | Y | 7624 | 2369 | 3292 | 4220 | 1730 | 4587 |
| X/Y | | 1.09 | 1.91 | 2.40 | 2.17 | 0.88 | 3.66 |

4. Preparation of Genetically-Modified Plant

<Preparation of Expression Vector>

As a result of above "2. Analysis of RNA" and "3. Analysis of protein", a nucleic acid sequence encoding glutelin B-1 having V/W=1.47 and X/Y=2.17 (GluB-1 gene: Accession No. X54314, AK107343), and a promoter sequence thereof (GluB-1 Promoter region: Accession No. AY427569) were obtained from NCBI Home Page, Nucleotide Database. Nucleic acid sequences neighboring to the nucleic acid sequence encoding glutelin B-1 were searched by Rice Annotation Project Database, and a nucleic acid sequence of 1.0 kb downstream of the nucleic acid encoding glutelin B-1 was obtained as a terminator sequence.

PCR primers were designed based on the obtained nucleic acid sequence information. A fragment (fragment A) comprising the promoter sequence of glutelin B-1, in which an Sse8387I site had been added to its N terminus, and a signal peptide sequence of glutelin B-1 was obtained by PCR (Primer1: CCTGCAGGACAGATTCTTGCTACCAACA (SEQ ID NO:1), Primer2: CAGGAGTGTTGGAGTATC-GAGGTAAAAGAA (SEQ ID NO:2)). A fragment (fragment B) comprising the terminator sequence on which SacI site had been added to its N terminus and EcoRI site had been added to its C terminus was also obtained by PCR (Primer3: GAGCTCTGTAATTGAGAACTAGTATC (SEQ ID NO:3), Primer4: GAATTCTCTTAACTTTACCTATGAT (SEQ ID NO:4)).

The obtained fragments A and B were introduced into *E. coli* using Zero Blunt TOPOPCR cloning kit (purchased from Invitrogen Corporation), and amplified. The fragment A, and a fragment C linking 7crp (pollen disease alleviation peptide) and a KDEL sequence (JP 2004-321079-A) were treated with NcoI (purchased from Takara Bio Inc.), and subsequently ligated using DNA Ligation Kit (purchased from Takara Bio Inc.). The fragment ligating the fragment A and the fragment C, and the fragment B were treated with SacI (purchased from Takara Bio Inc.), and ligated using DNA Ligation Kit (purchased from Takara Bio Inc.). The resulting ligated fragment (A, B, C) was treated with Sse8387I (purchased from Takara Bio Inc.) and EcoRI (purchased from Takara Bio Inc.), and subsequently ligated between restriction enzyme sites of EcoRI-Sse8387I of a plasmid pTL7 (H. Ebinuma et al., Molecular Methods of Plant Analysis, 22: 95, 2002) using DNA Ligation Kit (purchased from Takara Bio Inc.) to construct an expression vector. The above SEQ ID NOS correspond to those in Sequence Listing.

<Introduction into *Agrobacterium*>

*Agrobacterium tumefaciens* (*A. tumefaciens*) EHA 105 strain was inoculated in 10 mL of YEB liquid medium (5 g/L of beef extract, 1 g/L of yeast extract, 5 g/L of peptone, 5 g/L of sucrose, 2 mM $MgSO_4$, pH 7.2 at 22° C.) (hereinafter pH is the pH at 22° C. unless otherwise specified), and cultured at 28° C. until $OD_{630}$ reached the range of 0.4 to 0.6. After the culture, the cultured medium was centrifuged at 6900×g at 4° C. for 10 minutes to collect microbial cells. The collected microbial cells were suspended in 20 mL of 10 mM HEPES (pH 8.0), and the microbial cells were collected again by centrifuging at 6900×g at 4° C. for 10 minutes. These microbial cells were suspended in 200 μL of the YEB liquid medium to use as a bacterial solution for introducing the plasmid. The expression vector and 50 μL of the above bacterial solution for introducing the plasmid were mixed in a 0.5 mL tube, and the expression vector was introduced into *A. tumefaciens* EHA 105 strain using an electroporation method (Gene Pulsar II System (purchased from BIO-RAD Inc.). The microbial cells after the expression vector had been introduced were added to 200 μL of the YEB liquid medium and cultured at 25° C. for one hour with shaking. Subsequently, the microbial cells were seeded on YEB agar medium (1.5 w/v % agar, the other composition was the same as above) containing 50 mg/L of kanamycin, and cultured at 28° C. for 2 days. Then, a growing bacterial colony was transferred into the YEB liquid medium and further cultured. The plasmid was extracted from the growing microbial cells by an alkali method, and it was confirmed that the expression vector was introduced into these microbial cells.

<Transformation of Rice Plant with *Agrobacterium* EHA 105 Strain>

Completely matured seeds of the rice plant cultivar, "Nihonbare" were sterilized according to the method in Experimental Protocol for Model Plant (pages 93 to 98) in Cell Engineering Supplementary Volume, Plant Cell Engineering Series 4, and subsequently placed on N6C12 medium (N6 inorganic salts and vitamins (Chu C. C., 1978, Proc. Symp. Plant Tissue Culture, Science Press Peking, pp. 43-50), 30 g/L of sucrose, 2.8 g/L of proline, 0.3 g/L of casamino acids, 2 mg/L of 2,4-D, 4 g/L of Gel-Lyte, pH=5.8), cultured in a light place at 28° C. with being sealed with a surgical tape to sprout, and used as a material to be infected with *Agrobacterium* EHA 105. *Agrobacterium* EHA 105 introduced by the expression vector cultured on the YEB agar medium (15 g/L of Bacto agar, the other composition is the same as above) was transferred to the YEB liquid medium, cultured at 25° C. at 180 rpm overnight, subsequently microbial cells were collected by centrifuging at 3000 rpm for 20 minutes, and suspended in N6 liquid medium (N6 inorganic salts and vitamins, 30 g/L of sucrose, 2 mg/L of 2,4-D, pH=5.8) containing 10 mg/L of acetosyringone so that $OD_{630}$ was 0.15 to use as a suspension of *Agrobacterium* for infection. The prepared budding seeds were placed in a 50 mL tube, and the suspension of *Agrobacterium* for infection is poured on it, and the budding seeds were immersed for 1.5 minutes in the suspension of *Agrobacterium* for infection. After the immersion, the suspension of *Agrobacterium* for infection was discarded, the budding seeds were placed on a sterilized filter, and extra water was removed. These seeds were placed on the coexistence culture medium of N6C12 medium (N6 inorganic salts and vitamins, 30 g/L of sucrose, 2.8 g/L of proline, 0.3 g/L of casamino acids, 2 mg/L of 2,4-D, 4 g/L of Gel-Lyte, pH=5.2), and cultured in a dark place at 28° C. for 3 days with being sealed with the surgical tape, and then transferred to N6C12CH25 medium (N6 inorganic salts and vitamins, 30 g/L of sucrose, 2.8 g/L of proline, 0.3 g/L of casamino acids, 2 mg/L of 2,4-D, 500 mg/L of carbenicillin, 25 mg/L of hygromycin, 4 g/L of Gel-Lyte), and cultured.

<Redifferentiation of Transformant>

One week after the start of the culture in the above N6C12H25 medium, a budding sprout was removed from blastodisc tissue, and the remaining blastodisc tissue was cultured in the N6C14-CH25 medium (N6 inorganic salts and vitamins, 30 g/L of sucrose, 2.8 g/L of proline, 0.3 g/L of casamino acids, 4 mg/L of 2,4-D, 500 mg/L of carbenicillin, 25 mg/L of hygromycin, 4 g/L of Gel-Lyte) for one week, and further transferred to and cultured in MSRC medium (MS inorganic salts and vitamins (Murashige, T. and Skoog, F., 1962, Physiol. Plant., 15, 473), 30 g/L of sucrose, 30 g/L of sorbitol, 2 g/L of casamino acids, 500 mg/L of carbenicillin, 4 g/L of Gel-Lyte), thus redifferentiating a sprout or a young plant body.

5. Cultivation of Genetically-Modified Plant

The rice plant obtained by above "3. Preparation of genetically-modified plant" was cultivated as follows. The compositions of a cultivation solution C and a cultivation solution D used for the cultivation are shown in Table 4.

First, the sprout or the young plant body redifferentiated from the blastodisc tissue obtained by above "3. Preparation of genetically-modified plant" was transferred to a taking root medium, and grown until a young seedling having a height of about 20 cm was obtained.

The cultivation bed of the submerging solution system (supplied from M Hydroponic Research Co., Ltd.) was filled with 100 L of the cultivation solution C (see Table 4), the obtained seedlings were planted one by one, totally 77 seedlings were planted and cultured under the light condition: ambient temperature 28° C., humidity 50% and 11 hours, and the dark condition: ambient temperature 23° C., humidity 50% and 13 hours, for 45 days.

Additional fertilization was given so that the cultivation solution became the composition of the cultivation solution D (see Table 4), and the plants were cultured under the light condition: ambient temperature 28° C., humidity 50% and 11 hours, and the dark condition: ambient temperature 23° C., humidity 50% and 13 hours, for 45 days.

TABLE 4

TABLE FOR CULTIVATION SOLUTION COMPONENTS

| COMPONENT | CULTIVATION SOLUTION C CONTENT [mg/L] | CULTIVATION SOLUTION D CONTENT [mg/L] |
|---|---|---|
| $KNO_3$ | 38.9 | 174.1 |
| $NH_4NO_3$ | 21.8 | 97.9 |
| $(NH_4)_2 \cdot SO_4$ | 8.3 | 37.1 |
| $Mg(NO_3)_2 \cdot 6H_2O$ | 35.7 | 160.0 |
| $Ca(NO_3)_2 \cdot 4H_2O$ | 47.0 | 210.7 |
| NITRATE NITROGEN [mg/L] | 33 | 150 |
| AMMONIUM NITROGEN [mg/L] | 17 | 50 |

6. Measurement of Protein Content

Seeds were collected from the plant obtained in above "4. Cultivation of genetically-modified plant", and a protein content in the seed was measured as follows.

<Total Protein Content in Seed>

The protein content in the seed from which the blastodisc had been removed was measured using a near-infrared ray protein analysis apparatus NIRFLEX N-500 (supplied from BUCHI), and the total protein content was calculated from a seed weight.

<Amount of Functional Protein (Pollen Disease Alleviation Peptide: 7crp)>

The protein in the seed and protein markers with known concentrations were electrophoresed using SDS-PAGE kit (purchased from BIO-RAD Inc.), and then the gel was immersed in the fixation solution containing 40% ethanol and 10% acetic acid for two hours, and treated with Flamingo Gelstain (purchased from BIO-RAD Inc.). The treated gel was digitalized using Pharos FX Molecular Imager (purchased from BIO-RAD Inc.). A band position of 7crp was identified using Quantity One (purchased from BIO-RAD Inc.), and the weight of the pollen disease alleviation peptide (7crp) was calculated by comparing with the band intensity of the marker with the known concentration. In this way, the amount of the total protein in the seed collected from the genetically-modified plant and the amount of the functional protein introduced by the transformation were obtained.

Example 2

A genetically-modified plant was cultivated and a protein content was measured in the same manner as in Example 1, except that an ammonium nitrogen content of the cultivation solution D was changed to 150 mg/L.

Example 3

A genetically-modified plant was cultivated and a protein content was measured in the same manner as in Example 1, except that a nitrate nitrogen content of the cultivation solution D was changed to 50 mg/L and an ammonium nitrogen content of the cultivation solution D was changed to 150 mg/L.

Example 4

A genetically-modified plant was cultivated and a protein content was measured in the same manner as in Example 1, except that a nitrate nitrogen content of the cultivation solution D was changed to 600 mg/L and an ammonium nitrogen content of the cultivation solution D was changed to 200 mg/L.

Example 5

A genetically-modified plant was cultivated and a protein content was measured in the same manner as in Example 1, except that a nitrate nitrogen content of the cultivation solution D was changed to 70 mg/L and an ammonium nitrogen content of the cultivation solution D was changed to 70 mg/L.

Example 6

A genetically-modified plant was cultivated and a protein content was measured in the same manner as in Example 1, except that a nitrate nitrogen content of the cultivation solution D was changed to 750 mg/L and an ammonium nitrogen content of the cultivation solution D was changed to 750 mg/L.

Example 7

A genetically-modified plant was cultivated and a protein content was measured in the same manner as in Example 1, except that the promoter of glutelin B-5 was used as the promoter for expression of the objective protein.

Example 8

A genetically-modified plant was cultivated and a protein content was measured in the same manner as in Example 1, except that the cultivation condition of Y was the water cultivation.

Example 9

A genetically-modified plant was cultivated and a protein content was measured in the same manner as in Example 1, except that an ammonium nitrogen content of the cultivation solution B was changed to 20 mg/L.

Example 10

A genetically-modified plant was cultivated and a protein content was measured in the same manner as in Example 1, except that a nitrate nitrogen content of the cultivation solution B was changed to 20 mg/L.

Comparative Example 1

A genetically-modified plant was cultivated and a protein content was measured in the same manner as in Example 1, except that a nitrate nitrogen content of the cultivation solution D was changed to 20 mg/L and an ammonium nitrogen content of the cultivation solution D was changed to 20 mg/L.

Comparative Example 2

A genetically-modified plant was cultivated and a protein content was measured in the same manner as in Example 1, except that a nitrate nitrogen content of the cultivation solution D was changed to 800 mg/L and an ammonium nitrogen content of the cultivation solution D was changed to 800 mg/L.

Comparative Example 3

A genetically-modified plant was cultivated and a protein content was measured in the same manner as in Example 1, except that the promoter of 10 kDa prolamin was used as the promoter for expression of the objective protein.

Comparative Example 4

A genetically-modified plant was cultivated and a protein content was measured in the same manner as in Example 1, except that a nitrate nitrogen content of the cultivation solution B was changed to 20 mg/L and an ammonium nitrogen content of the cultivation solution B was changed to 20 mg/L.

Comparative Example 5

A genetically-modified plant was cultivated and a protein content was measured in the same manner as in Example 1, except that a nitrate nitrogen content of the cultivation solution B was changed to 800 mg/L and an ammonium nitrogen content of the cultivation solution B was changed to 800 mg/L.

Comparative Example 6

A genetically-modified plant was cultivated and a protein content was measured in the same manner as in Comparative Example 3, except a the nitrate nitrogen content of the cultivation solution D was changed to 20 mg/L and an ammonium nitrogen content of the cultivation solution D was changed to 20 mg/L.

Test results of above Examples 1 to 10 and Comparative Examples 1 to 6 are shown in following Table 5.

TABLE 5

| TEST RESULTS | | | | | | | | | | | | | |
|---|---|---|---|---|---|---|---|---|---|---|---|---|---|
| | SELECTION OF PROMOTER FOR SEED STORAGE PROTEIN GENE | | | | | | | | CULTIVATION OF GENETICALLY-MODIFIED PLANT | | | PROTEIN AMOUNT IN SEED | |
| | X | | | Y | | | | | | | | | |
| | NITROGEN CONTENT BEFORE FLOWERING [mg/L] | | | NITROGEN CONTENT [mg/L] | | | | | NITROGEN CONTENT BEFORE FLOWERING [mg/L] | | | TOTAL PROTEIN | FUNCTIONAL PROTEIN |
| | NITRATE NITROGEN | AMMONIUM NITROGEN | CULTIVATION METHOD | TOTAL NITROGEN | CULTIVATION METHOD | PROMOTER | V/W | X/Y | NITRATE NITROGEN | AMMONIUM NITROGEN | CULTIVATION METHOD | AMOUNT [mg] | AMOUNT [μg] |
| EXAMPLE 1 | 600 | 200 | WATER CULTIVATION | 50 | SOIL CULTIVATION | GLUTELIN B-1 (AK107343) | 1.47 | 2.17 | 150 | 50 | WATER CULTIVATION | 2.09 | 11.2 |
| EXAMPLE 2 | 600 | 200 | WATER CULTIVATION | 50 | SOIL CULTIVATION | GLUTELIN B-1 (AK107343) | 1.47 | 2.17 | 150 | 150 | WATER CULTIVATION | 2.19 | 11.7 |
| EXAMPLE 3 | 600 | 200 | WATER CULTIVATION | 50 | SOIL CULTIVATION | GLUTELIN B-1 (AK107344) | 1.47 | 2.17 | 50 | 150 | WATER CULTIVATION | 1.93 | 10.3 |
| EXAMPLE 4 | 600 | 200 | WATER CULTIVATION | 50 | SOIL CULTIVATION | GLUTELIN B-1 (AK107345) | 1.47 | 2.17 | 600 | 200 | WATER CULTIVATION | 2.66 | 14.3 |
| EXAMPLE 5 | 600 | 200 | WATER CULTIVATION | 50 | SOIL CULTIVATION | GLUTELIN B-1 (AK107346) | 1.47 | 2.17 | 70 | 70 | WATER CULTIVATION | 1.95 | 10.4 |
| EXAMPLE 6 | 600 | 200 | WATER CULTIVATION | 50 | SOIL CULTIVATION | GLUTELIN B-1 (AK107347) | 1.47 | 2.17 | 750 | 750 | WATER CULTIVATION | 2.59 | 13.9 |
| EXAMPLE 7 | 600 | 200 | WATER CULTIVATION | 50 | SOIL CULTIVATION | GLUTELIN B-1 (AY196923) | 1.59 | 2.40 | 150 | 50 | WATER CULTIVATION | 2.12 | 12.6 |
| EXAMPLE 8 | 600 | 200 | WATER CULTIVATION | 50 | WATER CULTIVATION | GLUTELIN B-1 (AK107347) | — | 1.43 | — | — | — | — | — |
| EXAMPLE 9 | 600 | 20 | WATER CULTIVATION | 50 | SOIL CULTIVATION | GLUTELIN B-1 (AK107347) | — | 1.98 | — | — | — | — | — |
| EXAMPLE 10 | 20 | 200 | WATER CULTIVATION | 50 | SOIL CULTIVATION | GLUTELIN B-1 (AK107347) | — | 1.82 | — | — | — | — | — |
| COMPARATIVE EXAMPLE 1 | 600 | 200 | WATER CULTIVATION | 50 | SOIL CULTIVATION | GLUTELIN B-1 (AK107347) | 1.47 | 2.17 | 20 | 20 | WATER CULTIVATION | 1.14 | 6.1 |
| COMPARATIVE EXAMPLE 2 | 600 | 200 | WATER CULTIVATION | 50 | SOIL CULTIVATION | GLUTELIN B-1 (AK107347) | 1.47 | 2.17 | 800 | 800 | WATER CULTIVATION | *1 | — |
| COMPARATIVE EXAMPLE 3 | 600 | 200 | WATER CULTIVATION | 50 | SOIL CULTIVATION | 10 KDa PROLAMIN | 0.80 | 0.88 | 150 | 50 | WATER CULTIVATION | 2.01 | 4.4 |
| COMPARATIVE EXAMPLE 4 | 20 | 20 | WATER CULTIVATION | 50 | SOIL CULTIVATION | GLUTELIN B-1 (AK107347) | — | 0.98 | — | — | — | — | — |
| COMPARATIVE EXAMPLE 5 | 800 | 800 | WATER CULTIVATION | 50 | SOIL CULTIVATION | GLUTELIN B-1 (AK107347) | — | *2 | — | — | — | — | — |
| COMPARATIVE EXAMPLE 6 | 600 | 200 | WATER CULTIVATION | 50 | SOIL CULTIVATION | 10 KDa PROLAMIN | 0.80 | 0.88 | 20 | 20 | WATER CULTIVATION | 1.12 | 3.0 |

*1, 2: NO SEED COULD BE COLLECTED DUE TO THE ROOT ROT.

INDUSTRIAL APPLICABILITY

The present invention is useful in fields such as biomass production, functional food production, biotechnology and breed improvement of the plants.

REFERENCE SIGNS LIST

G: chromosome
pmr 1: promoter
ptn1, ptn2: a structural gene region encoding a protein
tmr1: terminator
vct: plasmid vector

SEQUENCE LISTING FREE TEXT

SEQ ID NO. 1: Primer 1
SEQ ID NO. 2: Primer 2
SEQ ID NO. 3: Primer 3
SEQ ID NO. 4: Primer 4

The invention claimed is:

1. A method for hydroponic cultivation of a genetically-modified plant comprising: cultivating the genetically-modified plant in a hydroponic medium, wherein the genetically-modified plant is transformed by introducing an expression vector comprising:

a promoter that regulates expression of RNA expressed in a seed that satisfies the formula (1):

$$V/W>1.0 \quad (1),$$

wherein V and W are determined as follows:

V is an amount of RNA in the seed of a predetermined plant when the predetermined plant is cultivated in a hydroponic medium adjusted so that nitrate nitrogen is 70 mg/L to 750 mg/L and/or ammonium nitrogen is 70 mg/L to 750 mg/L for a period which starts from 30 days before the expected flowering date and ends at the flowering day, and W is an amount of RNA contained in a seed of the predetermined plant when the plant is cultivated in a medium adjusted so that nitrogen is 0 mg/L to 50 mg/L for a period which starts from 30 days before the expected flowering date and ends at the flowering day, wherein the predetermined plant is the same species as the genetically-modified plant, wherein RNA is extracted from the seeds 15 to 25 days after the flowering, wherein the promoter is a glutelin promoter; and a polynucleotide located downstream of the promoter and encoding a protein of interest, wherein the medium for cultivating the genetically-modified plant is adjusted so that a content of nitrate nitrogen is from 70 mg/L to 750 mg/L and a content of ammonium nitrogen is from 50 mg/L to 750 mg/L for a period which starts from 30 days before the expected flowering date and ends at the flowering day of the genetically-modified plant, and wherein the ratio of the contents of the nitrate nitrogen to the ammonium nitrogen is from 3:1 to 1:3.

2. The method according to claim 1, wherein the predetermined plant is a poaceous plant and the genetically-modified plant is a poaceous plant.

3. A method for production of a seed comprising cultivating the genetically-modified plant according to the method of claim 1 and collecting the seed.

4. The method according to claim 3, wherein the plant is a rice plant and the seed is a rice seed.

5. A method for hydroponic cultivation of a genetically-modified plant comprising:

cultivating the genetically-modified plant in a hydroponic medium, wherein the genetically-modified plant is transformed by introducing an expression vector comprising:

a promoter that regulates expression of RNA expressed in a seed, wherein the promoter is a glutelin promoter; and a polynucleotide located downstream of the promoter and encoding a protein of interest, wherein the medium for cultivating the genetically-modified plant is adjusted so that a content of nitrate nitrogen is from 70 mg/L to 750 mg/L and a content of ammonium nitrogen is from 50 mg/L to 750 mg/L for a period which starts from 30 days before the expected flowering date and ends at the flowering day of the genetically-modified plant, and wherein the ratio of the contents of the nitrate nitrogen to the ammonium nitrogen is from 3:1 to 1:3.

* * * * *

```
SEQUENCE LISTING

<160> NUMBER OF SEQ ID NOS: 60

<210> SEQ ID NO 1
<211> LENGTH: 28
<212> TYPE: DNA
<213> ORGANISM: Artificial Sequence
<220> FEATURE:
<223> OTHER INFORMATION: Synthetic Primer 1

<400> SEQUENCE: 1

cctgcaggac agattcttgc taccaaca                                        28


<210> SEQ ID NO 2
<211> LENGTH: 30
<212> TYPE: DNA
<213> ORGANISM: Artificial Sequence
<220> FEATURE:
<223> OTHER INFORMATION: Synthetic Primer 2

<400> SEQUENCE: 2

caggagtgtt ggagtatcga ggtaaaagaa                                      30


<210> SEQ ID NO 3
<211> LENGTH: 26
<212> TYPE: DNA
<213> ORGANISM: Artificial Sequence
<220> FEATURE:
<223> OTHER INFORMATION: Synthetic Primer 3

<400> SEQUENCE: 3

gagctctgta attgagaact agtatc                                          26


<210> SEQ ID NO 4
<211> LENGTH: 25
<212> TYPE: DNA
<213> ORGANISM: Artificial Sequence
<220> FEATURE:
<223> OTHER INFORMATION: Synthetic Primer 4

<400> SEQUENCE: 4

gaattctctt aactttacct atgat                                           25


<210> SEQ ID NO 5
<211> LENGTH: 2672
<212> TYPE: DNA
<213> ORGANISM: Oryza sativa
<220> FEATURE:
<221> NAME/KEY: misc_feature
<223> OTHER INFORMATION: LOCUS: AK101497 2672 bp mRNA linear PLN
      04-DEC-2008; DEFINITION: Oryza sativa Japonica Group cDNA
      clone:J033043G02, full insert sequence; ACCESSION: AK101497

<400> SEQUENCE: 5

ggccgcgccg tcacaccgcc gccgcctcct cgccatggac accccgccgt ccgccgccgc      60

cgccaccgcc accgccgttg cgtcagactc tgattgcgac tccgcgctcg tcgccgacgt     120
```

-continued

```
ggcggaagcg ctcgtgtcgg cgtcccgcct gccggagccg ccgcctatcc ccgccctcct    180
cgccctctac ctcccgcgcc tcgccgcctc ccaccacccg cgcgtgctct ccctcgccgc    240
ctcccacccg gggctcgcct cgccggacct gctcctcgcc taccgccgcc acctctcgcc    300
gccctcctgc ctcccctccc tcgtcccgct cctccccgtc ctcccctacc gccacctcct    360
cccgctcctc ctctccttcg tcccgctcga cccgcttcgc cacctccacc gccacctcct    420
cgcgcacctc cccacgagtc ccctcgccga tgccgcgctc tccgcctacg cccgcctccg    480
cctcccccac ctcgccgccc agctcctcca ctccctccgc cgccgccgtg gcgttcgccc    540
ttccctccag gctgccaacg ccgtcctctc cgcgctttcg cgcagcccat ccaccttgcc    600
gcaggcctcc ctcgatgtct tccgctccct catcgagctc cgcctccacc ccaaccacta    660
caccttcaac ctcctcgtcc acacgcattg ctccaagggc accctcgccg acgctctcgc    720
cacgctctcc accatgcagg ggttcggcct ctcccccgat gccgtcacct acaacacgct    780
cctcaatgcg cactgccgga agggcatgct cggcgaggcc cgggcactgc tggcgaggat    840
gaagagggac ggcatcgcgc ccacgcagcc aacgtacaat accctcgtgt cggcgtttgc    900
taggcttggg tggattaagc aggcgaccaa ggtcgtggag tccatgacag cctacgggtt    960
cgagcctgac ctgaggacgt acaatgtgct cgccgtgggg ctgtgccagg cggggaaggt   1020
ggacgaggca ttccggctga aggatgagat ggaacggctc agcaccgcgt tgccggatgt   1080
agtgacttac aatacacttg ttgacgcctg cttcaagtgg cggtactcat cagatgcatt   1140
gaggctgctt gaggaaatgc gtgacaaggg ggtgaagccg actttggtca cacataacat   1200
tgttgtgaag agtctttgca aggagggtaa attggaggag gcattgggga agctggagaa   1260
gatagcagag gaggggttgg caccagatgt aatcacgtac aatacgttga ttgatgcata   1320
ctgtaaggct ggtaatgtcg caaaagcatt cacattgatg gatgagatgg tcggaaaggg   1380
gctcaaaatg gacaccttca cacttaacac cgtgctgtac aacctatgca agatgaagcg   1440
ttatgaagat gctgaggagc ttttgcattc acccccgcag cggggtttcg tgcctgatga   1500
agtcagctat ggtactgtaa tggctgcgta cttcaaggag tataatccgg agcctgcttt   1560
gcgtctgtgg gaccagatga ttgagaggaa gttgatacca agcatttcaa cgtacaacac   1620
gttgatcaag ggctttgta ggatggagag gctgaaagaa gcaattgaca aattaaatga   1680
gctcgtggag aaggggttgg ttcctgatga aaccacatat aatatcatca ttcatgcata   1740
ctgcaaggaa ggggacctag aaaatgcctt tcgattccac aacaagatgg ttgagaattc   1800
cttcaagcca gatgttgtta cctgcaacac tttgatgaat ggcctttgtc tgcatgggaa   1860
gctagataaa gcattgaaac tctttgaatc atgggtggag aaggggaaga aggttgatgt   1920
tatcacatat aataccctaa ttcaatcgat gtgcaaagtt ggggatgttg atactgcttt   1980
gcacttcttt gatgacatgg aggtcaaggg attgcagcct gatgcattta cttataatgt   2040
tgtgttatct gcactatctg aagcaggaag atcagaagaa gcacataata tgctacataa   2100
gttagccgat agtggaaaat tatctcaaag ctttgcttgt cctctgttga agccttcttc   2160
tgcggatgaa gcagatgtca aggaacatga gggtaaacct gaggcagaat ccagtgaaaa   2220
agcacaagac aatgctctgg agacatacat ggaacgccta aatgggctat gtaccggtgg   2280
gcaattgaaa gaagctaaag ccgttttgga tgagatgatg caaaagggga tgcctgttga   2340
cagttcaaca tatataactt tgatggaagg gcttatcaag agacagaaaa ggcaaaccca   2400
tgcagctgga cagtccacac tatagatttt tgctcccgtg ggatgcgggc atgtgacatc   2460
```

```
attagggctt tagtcataaa tctggaaaac tcaagtgctt ggctaccagg attaccatca   2520

tggacaaaaa aaaaagaagt cggtatgtca acattttttt tctgcagtca gaaccttata   2580

tttgtaactt tcagtacaaa gtaaattcat ttttagtttt ttcactgcac gctatgttaa   2640

atgtataaag aataccagca gtgatttgaa tc                                 2672


<210> SEQ ID NO 6
<211> LENGTH: 780
<212> TYPE: DNA
<213> ORGANISM: Oryza sativa
<220> FEATURE:
<221> NAME/KEY: misc_feature
<223> OTHER INFORMATION: LOCUS: AJ002893 780 bp mRNA linear PLN
      15-APR-2005; DEFINITION: Oryza sativa mRNA for glycine-rich
      RNA-binding protein (OsGRP1); ACCESSION: AJ002893

<400> SEQUENCE: 6

gcgtctttct cctccccctc ccggttcggt tcggttcggg tccggttcga tttcgttttt     60

ttttcttctt cgtggggttg gtgggaaagc atggcggcgc cggatgttga gtaccgctgc    120

ttcgtcggcg gcctcgcctg ggccaccgac gaccgctccc tcgaagccgc cttctccacc    180

ttcggcgaga tcctcgagtc caagatcatc aacgatcggg agacggggag gtcgcgcggg    240

ttcgggttcg tgacgttctc gagcgagcag gccatgcgcg acgccatcga ggggatgaac    300

ggcaaggagc tcgacggccg caacatcacc gtcaacgagg cccagtcgcg ccgctccgga    360

ggcggaggcg gaggcggcta cggccagcgc ggcggaggcg gaggctacgg tggcggcggc    420

ggctacggtg gtggcggcgg cggtggctac gccagccgtg aaggcggcta cggcggtggc    480

ggcggctacg gtggcggccg tggcggcggc ggcggctacg gcggtggcta cggccgcggc    540

ggcggcaact ccgacgggaa ctggaggaac tgagcggtgg gccctcatgg ccaagttatc    600

tatctatcta atcgagctac catcatcatc atccgatcgt tatcatcgtt agttttgtgt    660

ggaactacta tctagtttgt gttactgtgt ggttgcccat ctgtgttttt gatcgcaaga    720

agaaagctcg tctcgtgttt gctttgatca aatgaaatga atgaatgaat cttagtgtga    780


<210> SEQ ID NO 7
<211> LENGTH: 330
<212> TYPE: DNA
<213> ORGANISM: Oryza sativa
<220> FEATURE:
<221> NAME/KEY: misc_feature
<223> OTHER INFORMATION: LOCUS: NM_001187429 330bp mRNA linear PLN
      08-JUN-2010; DEFINITION: Oryza sativa Japonica Group
      OS05g0329200) mRNA, complete cds.; ACCESSION: NM_001187429

<400> SEQUENCE: 7

atgaagatca ttttcgtctt tgctctcctt gctattgctg catgcagcgc ctctgcacag     60

tttcatgttt tagctgtgtt tcaactgaga aacaaccaag tctggcaaca gctcgcgctg    120

gtggcgcaac aatctcacta tcaggacatt aacattgttc aggccatagc gcagcagcta    180

caactccagc agtttggtga tctctacttt gatcggaatc tggctcaagc tcaagctctg    240

ttggctttta acgtgccatc tagatatggt atctacccta ggtactatgg tgcacccagt    300

accattacca cccttggcgg tgtcttgtaa                                     330


<210> SEQ ID NO 8
<211> LENGTH: 1655
<212> TYPE: DNA
<213> ORGANISM: Oryza sativa
<220> FEATURE:
<221> NAME/KEY: misc_feature
```

<223> OTHER INFORMATION: LOCUS: AK107271 1655 bp mRNA linear PLN
04-DEC-2008; DEFINITION: Oryza sativa Japonica Group cDNA
clone:002-125-H12, full insert sequence.; ACCESSION: AK107271

<400> SEQUENCE: 8

```
aaaagcattg agttcagtcc cacaaaaaca tggcaaccat caaattccct atagttttct     60
ccgtcgtttg cttgttcctc ttgtgtaatg gttcgttagc ccaacttctt agccaaagta    120
ctagtcaatg gcaaagttct cgccgtggaa gtccaagaga gtgcagattt gatcggttgc    180
aagcatttga gccgattcgc actgtaaggt cccaagctgg tacaactgag tttttgatg     240
tctctaatga gttgtttcaa tgtactggag tatttgttgt ccgtcgagtt atcgaaccta    300
gaggtcttct gttacctcac tactccgatg gagcaacttt ggtatatgtc atccaaggca    360
gaggtataac aggaccaact ttcccaggat gtcctgagac ctatcaacaa cagtttcagc    420
aatccgagca agaccaacaa ttggaaggcc aaagccaaag ccataaattt agagatgaac    480
atcaaaagat ccaccgtttt caacaggggg atgtagttgc attgcctgct ggtgttgctc    540
attggtgcta caatgatggt gatgcaccaa ttgttgccat atatgtcact gatatataca    600
atagtgctaa ccaacttgat cctagacaca gggatttctt tttagctggc aacaataaga    660
taggtcaaca attgtataga tatgaggcaa gggacaattc gaagaacgtc tttggtggat    720
ttagtgttga actacttagc gaggctcttg gcataagcag tggagtagca agacaactcc    780
agtgccaaaa tgaccaaaga ggagaaatag ttcgtgttga gcatgggctt tccttgctcc    840
aaccatatgc atcgttgcaa gagcaacaac aagaacaggt gcaatcgaga gactatggcc    900
aaacacaata tcaacaaaaa caacttcaag gtagttgctc taatggtttg gatgagacct    960
tttgtaccat gagggtaagg caaaatatcg acaacccaaa cctcgcagat acatacaacc   1020
ccagagcagg aaggatcaca tatctaaatg gccaaaagtt ccccattctt aatcttgtac   1080
agatgagtgc cgttaaagta aatttatatc agaacgcact cctttcacct ttttggaaca   1140
tcaacgctca tagtgtcgtg tatattactc aaggtcgtgc ccgagttcaa gtcgtcaaca   1200
acaatggaaa gacagtgttc gatggagagc tccgtcgtgg gcagcttcta attataccac   1260
aacaccatgt agtcattaaa aaggcacaaa gggaaggatg ctcatatatt gcattgaaaa   1320
ccaaccctga ctccatggtt agccacatgg caggaaagaa ttccatcttc cgcgcacttc   1380
ctgacgatgt tgtagcaaat gcatatcgta tctcaagaga agaagctagg aggctcaagc   1440
acaacagggg agatgagtta ggtgtgttca ctcctagtca tgcctacaag agctaccaag   1500
acatatctgt gagtgcataa ccaagaaatg tcaatcatag gcttggattg ctaaggatgg   1560
ttttcaaata aatcataagc aataaaagag tgcatgttgt tgcagctatg taatagtgga   1620
tggttggaag aataataata aatttgtgtt ccttt                              1655
```

<210> SEQ ID NO 9
<211> LENGTH: 1745
<212> TYPE: DNA
<213> ORGANISM: Oryza sativa
<220> FEATURE:
<221> NAME/KEY: misc_feature
<223> OTHER INFORMATION: LOCUS: AK102194 1745 bp mRNA linear PLN
04-DEC-2008; DEFINITION: Oryza sativa Japonica Group cDNA
clone:J033087C05, full insert sequence.; ACCESSION: AK102194

<400> SEQUENCE: 9

```
caagccgaga caacgcagag aaaggcgtct tcgtactcgc ctctctccgc gcctccgcgc     60
ttttcctcct cctctcccct ctctcccttc tccgccgccg tcgcagcatc aacccaatcc    120
```

```
gccgccatga gggagtgcat ctcgatccac atcggccagg ccggtatcca ggtcgggaac    180

gcgtgctggg agctctactg cctcgagcat ggcatccagg ctgatggtca gatgcccagt    240

gacaggactg ttggtggagg tgatgatgct ttcaacacct tcttcagtga gactggtgct    300

gggaagcatg ttccccgtgc tgtatttgtt gatcttgagc ctactgtgat tgatgaggtg    360

aggactggtt gctaccgcca gctcttccac cctgagcagc tcatcaatgg caaggaggat    420

gcagctaaca actttgcccg tggtcactac accattggca aggagattgt tgatctgtgc    480

cttgaccgca tcaggaagct tgctgacaac tgcactggtc tccaaggttt ccttgtgttc    540

aacgctgttg gaggtggaac gggctctggt cttggttccc ttctcctgga gcgcctttct    600

gtggactatg gcaagaagtc caagcttggg ttcactgtgt acccatcccc tcaggtctcc    660

acctctgtgg ttgagccata caacagtgtc ctctctaccc actccctcct tgagcacact    720

gatgttgctg ttctgcttga taatgaggcc atctatgaca tctgccgccg ctcccttgac    780

attgagcgcc caacctacac caacctcaac aggcttgtgt ctcaggttat ctcatccctg    840

accgcctccc tgaggtttga tggtgctctg aacgtggatg tcaatgagtt ccagaccaac    900

cttgtgccct acccaaggat ccacttcatg ctttcgtcct acgctccagt gatctctgcg    960

gagaaggcct accatgagca actctctgtt gccgagatca ccaacagtgc cttcgagcca   1020

tcctccatga tggccaagtg cgaccctcgc cacggcaagt acatggcctg ctgcctcatg   1080

taccgcggcg atgtcgtgcc caaggacgtg aacgccgccg tcgccaccat caagaccaag   1140

cgcaccatcc agttcgtgga ctggtgcccg acggggttca agtgcggcat caactaccag   1200

ccgcccagcg tcgtccccag cggcgacctc gccaaggtgc agagggccgt gtgcatgatc   1260

tccaactcca ccagcgtcgt ggaggtgttc tcccgcatcg accacaagtt cgacctcatg   1320

tactccaagc gcgccttcgt ccactggtac gtgggtgagg gcatggagga gggtgagttc   1380

tctgaggccc gtgaggatct cgccgcgttg gagaaggact acgaggaggt tggcgctgag   1440

tccgacgaga atgaggatgg cgatgatggt gacgagtact agaggagtcg tcgtcgtctg   1500

ggggcttgat gttctgtgtg tcaaggcctg attgataact gctgctatcc catgatctgc   1560

cagtgtggag ttatcctgtt gccgtgtgcg tgtgtcttcg agacatttgc ttgtggtgat   1620

ctgatgtttg gggcttaatg ggcttacaac cctcgttgtt gtaacctgtg tgccctgttt   1680

tatgtgagac cgcttcgtca cttataatat gcgcgtttgt tcaattttat gtttgtttct   1740

tgtgt                                                               1745
```

<210> SEQ ID NO 10
<211> LENGTH: 752
<212> TYPE: DNA
<213> ORGANISM: Oryza sativa
<220> FEATURE:
<221> NAME/KEY: misc_feature
<223> OTHER INFORMATION: LOCUS: AK120697 752 bp mRNA linear PLN 04-DEC-2008; DEFINITION: Oryza sativa Japonica Group cDNA clone:J013170I05, full insert sequence.; ACCESSION: AK120697

<400> SEQUENCE: 10

```
gaatggaggc atccaagcca agaagaggga gagcaccaag gacacgcgac tagcagaagc     60

cgagcgaccg cctcctcgat ccatatcttc cggtcgagtt cttggtcgat ctcttccctc    120

ctccacctcc tcctcacagg ttcttggtgt agcttgccac tttcaccagc aaagtttcat    180

gtctgatctc gacattcaga tcccaactgc cttcgatccc tttgctgagg ccaatgctgg    240

agactctggt gcggctgcag gatcaaagga ctacgttcat gtacgcatcc agcagcgtaa    300
```

```
tggccgtaag agcctgacca ctgtccaggg attgaagaag gaattcagct acaacaagat    360

cctcaaagat ctcaagaaag agttttgctg caatggtact gttgtccagg acccagagct    420

tggccaggtc attcaacttc agggtgatca gaggaaaaac gtatcaaatt ttcttgttca    480

ggccggcatt gtgaagaagg aacacatcaa gattcatggt ttctgagcaa ctgccaaaac    540

cattgcaaag actatagttt ggggtggagt atacttggtt gtgtacatgc ctgcgtgttc    600

cattgtacac acaaaaccta gccacctctt gactcttgag tgtatgcttg ttacccgtgt    660

gttgaagttt gtaagaggca ccatcactat agatgatggc ttgtgtccct ctttcatcaa    720

gattgaataa tatatgctac tttgagagcg ct                                  752
```

<210> SEQ ID NO 11
<211> LENGTH: 1130
<212> TYPE: DNA
<213> ORGANISM: Oryza sativa
<220> FEATURE:
<221> NAME/KEY: misc_feature
<223> OTHER INFORMATION: LOCUS: AK067141 1130 bp mRNA linear PLN 04-DEC-2008; DEFINITION: Oryza sativa Japonica Group cDNA clone:J013095J21, full insert sequence.; ACCESSION: AK067141

<400> SEQUENCE: 11

```
gatccatcca tccatgtcgt gttgttagct tcgttttctt cttgtttcat caatccaagg     60

agtgtggaag gccacacgcc aagattatat ctatgctaat ttgattagca gtaggattaa    120

ttcagtggct agcgtagctt gattagttgg tttaattagt tggagagtaa agaagatgtt    180

gggagtgttc agcggcgacg tggtggaggt gccggcggag ctggtggccg ccggcagccg    240

gacgccgtcg ccgaagacgc gggcgtcgga gctggtcagc cgcttcctcg gcggcgccga    300

gccggccgtg tccgtgcagc tcggcgacct cggccacctc gcctactccc atgccaacca    360

agccctcctc cgcccaaggt catttgcagc aaaagatgac atcttctgcc tgttcgaggg    420

agtcctggac aatcttggca acctgaacca gcagtatggt ctgtccaagg gtgccaatga    480

ggtgctcctt gtgatcgagg cgtacaagac gctgagagac agagcacctt accctgctag    540

cttcatgctc tcgcagctcg ccggcagcta cgcctttgtg ctcttcgaca agtccacctc    600

caccctcctt gtggcctctg atccggaggg aaaggtgtct ctgtattggg ggattactgc    660

tgatggatct gttgccttct ctgacaacat cgacctgctt aaaggatcgt gtggcaagtc    720

tcttgcacct ttcccacaag gctgcttcta ttccaatgct cttggagttg gaggcttgaa    780

gtgctatgag aacccaaagc acaaggtgac cgcagttcct gccaaagaag aagaaatttg    840

cggtgcaacc ttcaaggtgg aaggatctac aatcctcaca gcgctgcatt aggagatttt    900

tggatctcca gctgttgttg ggaaaggaaa actctgtagt ctgtaaatgg tggtgtaaca    960

tagtcgcaag gcatgcatct gatctgtatc atcatcttcc gtaaagacta gtgctgccag   1020

catggttagc acttttcagt gtttgggtgt gtgtatgatc tgtatcctat gctgttcagg   1080

cggaaatgaa cttcaggccc agctgtgtca gttgaatgta gttgtgttgc              1130
```

<210> SEQ ID NO 12
<211> LENGTH: 1653
<212> TYPE: DNA
<213> ORGANISM: Oryza sativa
<220> FEATURE:
<221> NAME/KEY: misc_feature
<223> OTHER INFORMATION: LOCUS: AK065009 1653 bp mRNA linear PLN 04-DEC-2008; DEFINITION: Oryza sativa Japonica Group cDNA clone:J013001E24, full insert sequence.; ACCESSION: AK065009

<400> SEQUENCE: 12

```
gtccctttcc caccgccgcc gccgccgccg aaaaagaaga agaagccgac gaggaggcga     60

ccatgagggc caaggtaacc aacctccccg ccgtctcctc ctcctcccta ggctgtctac    120

gcccatgtgt tgttgcgtcg tcgccgtgct tgttcttggt tggtcggggg ctgtgattac    180

aaagagagag gctcgagtgg tgaattttca cgggaaaccc tagcgaggcg gcggatctcg    240

ccgtgtgccc ccctcctccc cacgagcacc ccgtgtgttc acggcggtgg agtggatgga    300

acccgaggtg ccgccccatc gcgatgttgg cttgggtatc tcggtagttg catccatggc    360

tcaccatgct agtactactc cctccccgtc caaaatgtta ttgctacttc ctccgtttca    420

taaggttata agttcatttc tgggggagga atggatggcg cgtggtggtg ggttgctgtc    480

tcgtgagggg gtttcctgcc acgatgaagg cttcgttttt aacgcataca cttgatatga    540

gccccccttta tgatggtatt ttttatgatg gtatttggtt ggcgagctga attcctgttc    600

ttgcaacatc tgatggatgg tgcgtgatat ttgcttggat tacccgtttg tcagttagca    660

taggaaatta ggtttatcca ttagatgctg aagatgctca ttaattttgt ggtgctcact    720

gtttaaataa tactccgtag tactgtctgt aggaaattat aactattata tactaatagt    780

agctgttaag ttgatcagta attatgtgat gctcactgtc tatatgctat tcctgctgta    840

gtttcagtag gaaattatga atgctttcaa ttccctgtga acatgaaatt cagttacata    900

actgcattat cggtgattac ctaagttacc atttcatagt agttattttt gtggtgcaaa    960

gcttatccag ggaagtacat cttaatcatt cattcatgat ttgatagact ttgtaatatg   1020

aaattgtcat tctgtatttt gtcaatctgt attgccattt tgccatccat gatgccccta   1080

cttcagttgg tttgttcaac aatgtctatg ctggcattct tgaatcaccc aagcaatgaa   1140

tttaaatcaa ctaaatttgc tgtgatgcta tgttgcttct tgcttctgcg ttccagtttc   1200

tgttcaccct tgtgttcttt gagagaaggc tactgtgttg tgatcttttg cagtttctta   1260

gctatgctac catgcttatc ggctaatttt catcagttaa ctttctgtga tctgatactt   1320

ctgtttgtat tgtattcagt ggaagaagaa gcgcatgagg aggctgaaga ggaagcgccg   1380

aaagatgagg cagagatcta agtaggcgaa ggagatgggc gatcatggtg atggcgtgtc   1440

gcagtgatcc atgtcttcgg ctgccaagct cgttgatatg tcaagctgct tggcgtggtg   1500

ccaccattcg actgttgaat ggcttattta cctgtgctgt tatcatctta tatccctagt   1560

tttaccaaga gttttgcacc aagacatgtc ggttcagtta tgtgaacttg ttatggagcc   1620

gtatttgctg ctaatgttta cctaccgttg agt                                1653
```

<210> SEQ ID NO 13
<211> LENGTH: 805
<212> TYPE: DNA
<213> ORGANISM: Oryza sativa
<220> FEATURE:
<221> NAME/KEY: misc_feature
<223> OTHER INFORMATION: LOCUS: AF017360 805 bp mRNA linear PLN 28-MAY-1999; DEFINITION: Oryza sativa lipid transfer protein LPT III mRNA, complete cds.; ACCESSION: AF017360

<400> SEQUENCE: 13

```
gcatcagcaa ccaattcgca ccgatcgatc gatcgatcga tccagcaact agatcaacag     60

tactagctag gaagcatggc ccgtgcacag ttggtgttgg tcgccctggt ggcagctctg    120

ctcctcgccg ccccgcacgc cgccgtggcc atcacctgcg gccaggtcaa ctccgccgtc    180

gggccctgcc tgacctacgc ccgcggcggc gccgggccgt cggcggcctg ctgcaacggc    240

gtgaggagcc tcaaggcggc agcaagcacg accgcagacc ggcgcaccgc ctgcaactgc    300
```

```
ctcaagaacg cggcccgcgg catcaagggg ctcaacgccg gcaacgccgc cagcatcccc    360

tccaagtgcg gcgtcagcgt ccctacacca tcagcgcttc catcgactgc tccagggtga    420

gctgagccat cgatcagaga gacggatcat atatatacag cagcgcgccg gttgccacct    480

agtagattct gcctgggtgc atgtgtggac ccgaattctg tatccagtac tagtagtatc    540

atatctgtat tctggaataa aagatgagct agctaaggtc tcgatcaatc accatgcatg    600

catgtgtgtg catccatggt tgatcggccg gtcacgctag ctagctttct tcttcttgtg    660

tgttcgtctc gtacgttttg ctccttttcg aggggtacgt gtaccagaga gagctagaga    720

ttctacatgc atgtactgca actccttgta ctacgtgctt tgttttggat tattacacat    780

acatatagct ctttttcgta cattt                                          805


<210> SEQ ID NO 14
<211> LENGTH: 1130
<212> TYPE: DNA
<213> ORGANISM: Oryza sativa
<220> FEATURE:
<221> NAME/KEY: misc_feature
<223> OTHER INFORMATION: LOCUS: AK071205 1130 bp mRNA linear PLN
      04-DEC-2008; DEFINITION: Oryza sativa Japonica Group cDNA
      clone:J023085D08, full insert sequence.; ACCESSION: AK071205

<400> SEQUENCE: 14

gactctcacc aacaacagta acccaaccag agagcttgcg gaagcggggg tttggtgcgg     60

gcgcgcgcgt gtgagggggg agagaaggcc aggaggaggc gacgccgtcg cccgagggag    120

gcaaaaatcc gatcctcctc ctgccctgct cgctcgctcg ctcgcctgcg ctgcgcgcac    180

ttggccccgt cccgtccgtt cccgctcgcc aggcatagaa agatggtgct ctgggtcttc    240

ggctatggct ccctgatctg gaaccccgga ttcgacttcg atgagaagat cctgggcttc    300

gtcaagggct acaaacgcac cttcaatctt gcttgcattg accatcgggg cacgccggag    360

catcctgcga ggacctgcac acttgagtcc gacgaggaag ccatatgctg gggggattgca    420

tactgtgtca aagggggggct taaaaaggag caagaagcaa tgaagtactt ggaaagaaga    480

gagtgtgagt atgaccagaa gatctctgtg gatttctaca aggaaggaga ctctttgaag    540

ccagctgtga caggtgtact agtctttgta tccactcctg atccagtagg caacaaatac    600

tatcttgggc ctgctccttt ggaggacatg gcaaggcaaa ttgctacagc caatggcccc    660

aatgggaata acagggatta cctgttctca atggagaagg cattgtccaa catatgccat    720

gaagatgatt caatcatcga gctagctaac gaggtcagga aggtgttgag ccggccgaag    780

gagaagatca ctggctccga tagcccacaa aaatctcacg ctctcgtaca cctgtctgcg    840

cttcctgagg gcactgttgt ggactcaaga tagcaagctc ggcggtggaa gagatgagat    900

ctcctctgac ctactcactc ttgacgctgg attgaacgag tttaacagtc tgcttcgagc    960

tccctggcac actggggaac cagaatgtgc tgattttctt tcgcaaccgc tgcggcaatg   1020

ctgtaacttt cattttgcta atactagagc cgagactggt gtgctgctgt ttcctttgac   1080

acactaaata ataaagggat tccatgagct tttcactctt gagctgttgc              1130


<210> SEQ ID NO 15
<211> LENGTH: 779
<212> TYPE: DNA
<213> ORGANISM: Oryza sativa
<220> FEATURE:
<221> NAME/KEY: misc_feature
<223> OTHER INFORMATION: LOCUS: AK059164 779 bp mRNA linear PLN
      04-DEC-2008; DEFINITION: Oryza sativa Japonica Group cDNA
```

clone:001-023-D11, full insert sequence.; ACCESSION: AK059164

<400> SEQUENCE: 15

```
ctcgtgctct ctttgaggtg ggttggcttc tcctcccccct ctttaccttt tcctcctcgg      60

ttcggttccg tggttcgtct agggtttagt gggttgagat ggcggcgccg gatgtcgagt     120

accgctgctt cgtcggcggc ctcgcctggg ccaccgacga ccgctccctc gaggccgcct     180

tctccaccta cggcgagatc ctcgactcca agatcatcaa cgacagggag acggggaggt     240

cacgtgggtt tggcttcgtc accttctcct ccgagcagtc gatgcgcgac gccatcgagg     300

gcatgaacgg caaggagctc gacggccgca acatcaccgt caatgaggcc cagtcccgcc     360

gctccggcgg cggaggcggg ggctacggcg gcggcggtgg cggctacggc ggcggtcgtg     420

gaggcggcgg ctacggagga ggtggcggcg gcggctacgg gcgccgtgag ggcggctacg     480

gtggcggcgg ctacggcggc gactccggcg ggaactggag gaactgattg gtggggccca     540

tcgtggccag ttatccttag ctatccgtgt cagaatcatc ttatcatcga gtcgagtcgt     600

tatcgtgtcc agtggctctc tcgagtcgag aagccctcta tccatccatc cagtgttagg     660

tgttcttcgt ccgtgatgtt accatgaatt gagttcgctt tggttatggt gtttgaactg     720

cttgttgcta tctatcggaa tgaaatgaaa tagaaaacaa ggagaaaaaa aagagttcg      779
```

<210> SEQ ID NO 16
<211> LENGTH: 1667
<212> TYPE: DNA
<213> ORGANISM: Oryza sativa
<220> FEATURE:
<221> NAME/KEY: misc_feature
<223> OTHER INFORMATION: LOCUS: AK107238 1667 bp mRNA linear PLN 04-DEC-2008; DEFINITION: Oryza sativa Japonica Group cDNA clone:002-125-F02, full insert sequence.; ACCESSION: AK107238

<400> SEQUENCE: 16

```
gaaccagccc aagtttccaa taacatcctc aaatagctat ggcgaccata gctttctctc      60

ggttatctat ctacttttgt gttcttctcc tatgccatgg ctctatggcc cagctatttg     120

gtccgaacgt aaatccatgg cacaaccctc ggcaaggagg ttttagggag tgtagatttg     180

atagactaca agcatttgaa ccacttcgga gagtgaggtc agaagccggg gttacagagt     240

actttgatga gaagaatgaa caattccagt gcacaggtac atttgtcatc cgacgtgtca     300

ttgagcctca aggccttctg gtacctcgat acagcaatac tcctggcatg gtctacatca     360

tccaagggag aggttctatg ggattaactt tccccggctg cccagcaacc taccaacaac     420

aattccaaca attcttgcct gaaggccaaa gccagagcca aaaatttagg gatgagcacc     480

aaaagatcca ccaatttaga caaggagata tcgttgcact gccagctggt gttgcgcatt     540

ggttctacaa tgaaggcgat gcaccagttg ttgctctata tgtcttcgac ttaaacaaca     600

acgctaatca gcttgaacca aggcagaagg agttcttatt ggcgggtaac aacaacaggg     660

agcaacaaat gtatggtcgc tcaatcgagc aacactctgg gcaaaacata tttagcggtt     720

tcaacaatga gctactaagt gaggccttag gcgtcaatgc attggtagca aagaggctac     780

aaggccaaaa cgaccaaaga ggagagatca tacgggtaaa gaatggcctt aaactgttga     840

gacctgcttt tgcacaacaa caggaacaag cacaacagca ggaacaagca caagctcaat     900

accaagttca gtacagtgaa gaacaacaac catctacgcg ttgcaacggt ttagatgaga     960

acttctgcac aatcaaggca aggttgaaca tcgaaaatcc tagccatgct gatacttaca    1020

acccacgtgc tggaaggatc acacgtctca acagtcagaa gttccccatt cttaaccttg    1080
```

```
tacaattgag tgctactaga gtaaatctat accagaatgc tattctctct ccgttttgga   1140

acgttaatgc ccatagcctg gtgtatatcg ttcaagggca tgctcgagtt caggtcgtta   1200

gtaaccttgg aaagacggta ttcaatggcg ttctacgtcc aggtcaattg ctgatcattc   1260

cgcaacacta cgttgtcttg aagaaagcag agcatgaagg atgccaatac atttcattca   1320

agaccaatgc aaactccatg gtgagccacc ttgcagggaa gaactcaata ttccgtgcca   1380

tgccagtgga tgtgatcgct aatgcttacc gcatatcgag ggagcaagca cgaagcctta   1440

agaataatag gggagaagag ctcggtgcct tcactcctag atatcaacaa cagacctacc   1500

taggcttctc aaatgagtcg gagaacgagg cctcagagtg atgtactaat gaaatagtat   1560

aggtgtatca aaaaaaaata aaatgccaca agtatgtgaa actttgtggc ggttctgttc   1620

taagtttatg aagcactaat aaaatgctac aactgtttta ttcatgc                1667
```

<210> SEQ ID NO 17
<211> LENGTH: 617
<212> TYPE: DNA
<213> ORGANISM: Oryza sativa
<220> FEATURE:
<221> NAME/KEY: misc_feature
<223> OTHER INFORMATION: LOCUS: AB016505 617 bp mRNA linear PLN 09-JAN-1999; DEFINITION: Oryza sativa mRNA for prolamin, complete cds, clone:lambda RM9.; ACCESSION: AB016505

<400> SEQUENCE: 17

```
gcaaaagcat aagaactaga aacccaccac aatgaagatc attttcttct ttgctctcct     60

tgctattgct gcatgcagtg cctctgcgca gtttgatgct gttactcaag tttacaggca    120

atatcagctg cagccgcatc tcatgctgca gcaacagatg cttagcccat gcggtgagtt    180

cgtaaggcag cagtgcagca cagtggcaac cccccttcttc caatcacccg tgtttcaact    240

gagaaactgc caagtcatgc agcagcagtg ctgccaacag ctcaggatga tcgcacaaca    300

gtctcactgc caggccatta gcagtgttca ggctattgtg cagcagctac ggctacaaca    360

gtttgctagc gtctacttcg atcagagtca agctcaagcc caagctatgt tggccctaaa    420

catgccgtca atatgcggta tctacccaag ctacaacact gctccctgta gcattcccac    480

cgtcggtggt atctggtatt gaattgtagc agtatagtag tacaggagag aaaaataaag    540

tcatgcatca tcgtgtgtga caagttgaaa catcggggtg atacaaatct gaataaaaat    600

gtcatgcaag tttaaac                                                    617
```

<210> SEQ ID NO 18
<211> LENGTH: 1460
<212> TYPE: DNA
<213> ORGANISM: Oryza sativa
<220> FEATURE:
<221> NAME/KEY: misc_feature
<223> OTHER INFORMATION: LOCUS: AK099086 1460 bp mRNA linear PLN 04-DEC-2008; DEFINITION: Oryza sativa Japonica Group cDNA clone:J023009G10, full insert sequence.; ACCESSION: AK099086

<400> SEQUENCE: 18

```
aggccgtggt gggcccaccg tctagcgaaa accaccccg ccgccgcgcg tgccacgttt     60

actcccgtgg gccccgcaac gaggcacaaa ccctaggccg cttatataaa cccgacccgc    120

cccgctccgg tgatcggatc cccacagctt tgcgtttgca ctcctctcga tctccattcg    180

tttttgagtt cctcgtttgc tccgcctctc tttcactcat gggcaagatt aagatcggaa    240

tcaatgggtt cggccgcatc ggcaggctgg tggccagggt ggcgctgcag agcgaggatg    300

tcgagctcgt tgccgtcaac gatcccttca tcaccaccga gtacatgaca tacatgttca    360
```

```
agtatgacac cgtccacggc cagtggaagc atcatgaggt caaggtcaag gactccaaga    420
ccctcatctt tggcacgaaa gaggttgcgg tgttcggctg caggaaccct gaggagatcc    480
catgggctgc ggctggtgct gaatacgttg ttgagtctac tggtgttttc accgacaagg    540
acaaggcagc agctcacttg aagggtggtg ccaagaaggt cgtcatttct gctcccagca    600
aagacgcccc catgttcgtt gttggtgtca acgagaagga gtacaagtct gacgttaaca    660
ttgtctccaa cgctagttgc accaccaact gcctggctcc tctcgccaag gtcatcaatg    720
acagatttgg catcgttgag ggtttgatga ccactgtcca tgccatcact gctacccaga    780
agactgttga tgggccctcg atgaaggact ggagaggtgg aagggctgct agcttcaaca    840
tcattcctag cagcactgga gctgccaagg ctgtcggcaa ggtgcttcct gccctcaatg    900
gaaagctgac tggaatggct ttccgtgttc ccacagtcga tgtttccgtt gttgatctga    960
ctgttaggct tgagaagccc gccagctatg accagatcaa ggctgcaatc aaggaggagg   1020
ctgagggcaa gctcaagggc atccttggat acgttgagga ggaccttgtt tccactgact   1080
tccagggtga cagcaggtcc agcatctttg atgccaaggc tggcattgct ttgagcgaca   1140
cgttcgtgaa gcttgtgtcc tggtacgaca acgaatgggg atacagcacc cgtgtgatcg   1200
acctgatccg tcacatgcac agcaccaact agacgagccc tcctcatgga ggcctgcaga   1260
tacaggggag ttgtgttttg ccccagagaa gagtagatga agcctcttcc gagaataaat   1320
tttaaattct gtatggtttt atgtccgtcg aaacctaaaa ctatacttgg ttgtatcatg   1380
gtggttggtt gggcctggtc atggctcata ttttgtgtct aattttcttg cgcttaatct   1440
aaatcgaagt gttgcttcgc                                               1460
```

<210> SEQ ID NO 19
<211> LENGTH: 942
<212> TYPE: DNA
<213> ORGANISM: Oryza sativa
<220> FEATURE:
<221> NAME/KEY: misc_feature
<223> OTHER INFORMATION: LOCUS: AY166458 942 bp mRNA linear PLN 23-MAY-2006; DEFINITION: Oryza sativa (japonica cultivar-group) alpha-amylase/subtilisin inhibitor mRNA, complete cds.; ACCESSION: AY166458

<400> SEQUENCE: 19

```
tttcgtcgtg cacgagccgg agcaggagac gaagggtttc agccatggtt agcctccgcc     60
tcccccctcat actcctctcc ctcctggcca tctccttctc atgcagcgcc gcgccgccgc    120
cggtgtacga cacggagggc cacgagctga gcgccgacgg gagctactac gtcctcccgg    180
ctagccccgg ccacggaggg ggcctcacga tggcgccccg cgtgctcccc tgcccgctcc    240
tcgtggcgca ggagacggac gagcgccgca aggggttccc cgtgcgcttc accccgtggg    300
gcggcgccgc ggcgccggag gacaggacca tccgcgtctc gaccgacgtc cgcatccgct    360
tcaacgccgc gacgatctgc gtgcagtcca ccgagtggca tgtcggcgac gagccgctca    420
cgggggcgcg gcgcgtggtg acggggccgt tgatcgggcc gagcccgagc gggcgggaga    480
acgcgttccg cgtggagaag tacggcggtg ggtacaagct ggtgtcgtgc agggactcgt    540
gccaggacct gggcgtgtca agggacggcg cgcgggcgtg gctgggcgcg agccagccgc    600
ctcacgtcgt ggtcttcaag aaggccaggc caagcccacc agagtaaacg aggggagggg    660
aggggggggg ggtcactcat gcgttgcgtg gtgcggtggt gcctctgtag cgtgtatagg    720
tagtagggtg cgtgcgtgcg tgcgcatgtg ctggttgaat aatgtgtgaa gaggctagca    780
```

```
ggtattgctc cgtggttctg ttctcatggt cgtgtcatgt ctgttagtcg tgataactcg    840

tgagcactga gcaagtgagc aggactgcct ctggctgtct ggcccagccg gacttgttaa    900

gtccaaatgg aatgaacgaa ttgtgcggga taaaaaaaaa aa                       942


<210> SEQ ID NO 20
<211> LENGTH: 1588
<212> TYPE: DNA
<213> ORGANISM: Oryza sativa
<220> FEATURE:
<221> NAME/KEY: misc_feature
<223> OTHER INFORMATION: LOCUS: AY987390 1588 bp mRNA linear PLN
      19-APR-2005; DEFINITION: Oryza sativa (japonica cultivar-group)
      glutelin precursor (GluB7) mRNA, complete cds.; ACCESSION:
      AY987390

<400> SEQUENCE: 20

tcggtctttc aactcacatc aattagctta agtttccatt agcaactgct aatagctatg     60

gcaactacca ttttctctcg tttttctata tacttttgtg ctatgctatt atgccagggt    120

tctatggccc aactatttaa tccaagcaca aacccatggc atagtcctcg gcaaggaagt    180

tttaaggagt gtaggtttga tagactacaa gcatttgagc cacttcgaaa agtaaggtca    240

gaagctgggg tgactgagta cttcgatgag aagaatgaat tattccaatg cacaggtact    300

tttgtcatcc gacgtgtcat tcaacctcaa ggccttttgg tacctcgata tagcaatact    360

cctggcctgg tctacatcat tcaagggagg ggttctatgg gtttaacctt ccccggttgc    420

ccagcgactt atcagcaaca attccaacaa ttttcgtctc aaggccaaag tcaaagccaa    480

aagtttaggg atgagcatca aaagattcat caatttagac aaggagatgt tgttgcactc    540

ccagccggtg ttgcacattg gttctacaat gatggtgatg catcggttgt tgccatatat    600

gtttatgaca taaacaacag tgcaaatcaa cttgaaccaa ggcaaaagga gttcctatta    660

gctggtaaca acaatagggt tcaacaagta tatggcagct caattgagca acactctagc    720

caaaacatat tcaacggatt cggtactgag ctactaagtg aggctttagg catcaacaca    780

gtagcagcaa agaggctgca gagccaaaat gatcagagag gagagatcgt acatgtgaaa    840

aatggccttc aattgttgaa accgactttg acacaacaac aagaacaagc acaagctcaa    900

taccaagagg ttcaatatag tgaacaacaa caaacatctt cccgatggaa cggattggag    960

gagaacttct gcacaatcaa ggcaagagta aacattgaaa atcctagtcg tgctgattca   1020

tacaacccac gtgctggaag gatttcaagt gtcaacagcc agaagttccc catccttaac   1080

ctcatccaaa tgagtgctac cagagtaaac ctataccaga atgctattct ctcaccattc   1140

tggaatgtca atgctcatag tttggtctat atgattcaag ggcaatctcg agttcaagtc   1200

gttagtaact ttggaaagac tgtgttcgat ggtgtccttc gccctggaca actattgatc   1260

attccacaac attatgctgt cttgaagaaa gcagagcgtg aaggatgcca atatattgca   1320

atcaagacaa acgctaacgc cttcgtcagc caccttgcag gaaaaaactc agtattccgc   1380

gccttaccag ttgatgtggt cgctaatgct taccgcatct cacgggagca agcccgaagc   1440

atcaagaaca ataggggaga agagcacggt gccttcactc ctagatttca acaacaatac   1500

tacccaggat tctcgaatga gtccgaaagt gagacttcag agtaatgtaa ctgagaacta   1560

gttctggcat atagcaaaat aaaaaaaa                                       1588


<210> SEQ ID NO 21
<211> LENGTH: 1764
<212> TYPE: DNA
<213> ORGANISM: Oryza sativa
```

<220> FEATURE:
<221> NAME/KEY: misc_feature
<223> OTHER INFORMATION: LOCUS: AK107314 1764 bp mRNA linear PLN
04-DEC-2008; DEFINITION: Oryza sativa Japonica Group cDNA
clone:002-126-D11, full insert sequence.; ACCESSION: AK107314

<400> SEQUENCE: 21

```
aaaagcattc agttcattag tcctacaaca acatggcatc cataaatcgc cccatagttt     60

tcttcacagt ttgcttgttc ctcttgtgcg atggctccct agcccagcag ctattaggcc    120

agagcactag tcaatggcag agttctcgtc gtggaagtcc gagaggatgt agatttgata    180

ggttgcaagc atttgagcca attcggagtg tgaggtctca agctggcaca actgagttct    240

tcgatgtctc taatgagttg tttcaatgta ccggagtatc tgttgtccgc cgagttattg    300

aacctagagg cctactacta ccccattaca ctaatggtgc atctctagta tatatcatcc    360

aagggagagg tataacaggg ccgactttcc caggctgtcc tgagacctac cagcagcagt    420

tccaacaatc agggcaagcc caattgaccg aaagtcaaag ccaaagccat aagttcaagg    480

atgaacatca aaagattcac cgtttcagac aaggagatgt tatcgcgttg cctgctggtg    540

tagctcattg gtgctacaat gatggtgaag tgccggttgt tgccatatat gtcactgata    600

tcaacaacgg tgctaatcaa cttgaccctc gacagaggga tttcttgtta gctggaaata    660

agagaaaccc tcaagcatac aggcgtgaag ttgaggagtg gtcacaaaac atatttagtg    720

gctttagcac tgaactgctt agcgaggctt ttggcataag caaccaagtt gcaaggcagc    780

tccagtgtca aaatgaccaa agaggagaaa ttgtccgcgt tgaacgcggg ctcagtttgc    840

tgcaaccata tgcatcattg caagagcagg aacaaggaca aatgcaatca agagagcatt    900

atcaagaagg aggatatcag caaagtcaat atgggagtgg ctgccctaac ggtttggatg    960

agaccttttg caccatgagg gtaaggcaaa acatcgataa tcctaaccgt gctgacacat   1020

acaacccaag agctggaagg gttacaaatc tcaacagcca gaatttcccc attcttaatc   1080

ttgtacagat gagcgccgtt aaagtaaatc tataccagaa tgcactcctt tcaccgttct   1140

ggaacatcaa cgctcacagc atcgtgtata ttactcaagg ccgagcccag gttcaagttg   1200

tcaacaacaa tggaaagacg gtgttctacg gagagcttcg tcgtggacag ctacttattg   1260

taccacaaca ctatgtagtt gtaaagaagg cacaaagaga aggatgtgct tacattgcat   1320

tcaagacaaa ccctaactct atggtaagcc acattgcagg aaagagttcc atcttccgtg   1380

ctctcccaac tgatgttcta gcaaatgcat atcgcatctc aagagaagag gctcagaggc   1440

tcaagcataa cagaggagat gagttcggtg cattcactcc cctccaatac aagagctacc   1500

aagacgttta taatgtggcg gaatcctctt aagttggtaa tgcggataaa gaataactaa   1560

ataaataaat aaataaattg caagcaattg cgttgctgct atgtactgta aaagtttctt   1620

ataatatcag ttctgaatgc taaggacatc cctcaagatg gtctttctat ttttgtgttc   1680

ccgttccaat gtactgttgg tatcctcttg gagattcatc aatatgagaa aacagagaat   1740

ggacaaccct cccttatctt atgg                                          1764
```

<210> SEQ ID NO 22
<211> LENGTH: 1637
<212> TYPE: DNA
<213> ORGANISM: Oryza sativa
<220> FEATURE:
<221> NAME/KEY: misc_feature
<223> OTHER INFORMATION: LOCUS: X15833 1637 bp mRNA linear PLN
18-APR-2005; DEFINITION: Rice mRNA for glutelin.; ACCESSION:
X15833

<400> SEQUENCE: 22

```
gaattcccca taagcaagta caaatagcta tggcgagttc cgttttctct cggttttcta     60
tatactttg tgttcttcta ttatgccatg gttctatggc ccagctattt aatcccagca     120
caaacccatg gcatagtcct cggcaaggaa gttttaggga gtgtagattt gatagactac    180
aagcatttga accacttcgg aaagtgaggt cagaagctgg ggtgactgag tacttcgatg    240
agaagaatga attattccag tgcacgggta cttttgtgat ccgacgtgtc attcagcctc    300
aaggcctttt ggtacctcga tacacaaata ttcctggcgt ggtctacatc atccaaggga    360
gaggttctat gggtttaacc ttccccggtt gccctgcgac ttaccagcaa caattccaac    420
aattttcatc tcaaggccaa agtcagagcc aaaagtttag agatgagcac caaaagattc    480
atcaatttag gcaaggagac attgttgcac tcccagctgg tgttgcacat tggttctaca    540
atgatggtga tgcacctatt gttgccgtat atgtttatga cgtaaacaac aacgccaatc    600
agcttgaacc taggcaaaag gagttcctat tagccggcaa caacaatcgg gctcaacaac    660
aacaagtata tggtagctca attgagcaac actctgggca aaacatattc agcggatttg    720
gtgttgagat gctaagtgag gctttaggca tcaacgcagt agcagcaaag aggctacaga    780
gccaaaatga tcaaagagga gagatcatac atgtgaagaa tggccttcaa ttgttgaaac    840
cgactttgac acaacagcaa gaacaagcac aagcacaaga tcaatatcaa caagttcaat    900
acagtgaacg acagcaaaca tcttctcgat ggaacggatt ggaggagaac ttttgcacga    960
tcaaggtgag agtaaacatt gaaaatccta gtcgtgctga ttcatacaac ccacgtgccg   1020
gaaggataac aagtgtcaat agtcagaagt tccccatcct taacctcatc caaatgagcg   1080
ctaccagagt aaacctatac cagaatgcta ttctctcgcc gttctggaac gtcaatgctc   1140
atagtttggt ctatatgatt caagggcgat ctcgagttca agtcgttagt aactttggaa   1200
agactgtgtt tgatggtgtc cttcgcccag cacaattatt gatcattccg caacattatg   1260
ctgtcttgaa gaaagcagag cgtgaaggat gccaatatat cgcaatcaag acaaacgcta   1320
acgccttcgt cagccacctt gcagggaaaa actcagtatt ccgtgccttg ccagttgatg   1380
tagtcgctaa tgcgtatcgc atctcaaggg agcaagcccg aagcctcaag aacaacaggg   1440
gagaagagca cggtgccttc actcctagat ttcaacaaca atactaccca ggattatcga   1500
atgagtccga aagcgagacc tcagagtaat gtaattgaga actagtatcg gcgtagagta   1560
aaataaaaca ccacaagtat gacacttggt ggtgattctg ttcgatatca gtactaaata   1620
aaggttacaa acttctt                                                  1637
```

<210> SEQ ID NO 23
<211> LENGTH: 887
<212> TYPE: DNA
<213> ORGANISM: Oryza sativa
<220> FEATURE:
<221> NAME/KEY: misc_feature
<223> OTHER INFORMATION: LOCUS: AK061894 887 bp mRNA linear PLN 04-DEC-2008; DEFINITION: Oryza sativa Japonica Group cDNA clone:001-041-G07, full insert sequence.; ACCESSION: AK061894

<400> SEQUENCE: 23

```
acgcagcgat ctgaagtgaa acagcaaaaa aaatcaaaca aaaagaaaaa atattcccca     60
tctgtgaaat tcgcaaaacc ctagcgcggc ggcgatgtcg aacacgaggg tgttcttcga    120
catgaccgtc ggcggagctc cggcggggcg gatcgtgatg gagctgtacg cgaaggacgt    180
gccgcggacg gcggagaact tccgcgcgct ctgcaccggc gagaagggcg tgggcaagag    240
```

```
cggcaagccg ctgcactaca aggggagcac cttccaccgc gtgatcccgg agttcatgtg    300

ccagggcggc gacttcaccc gcggcaacgg cacgggaggg gagtcgatct acggcgagaa    360

gttcgccgac gaggtgttca agttcaagca cgacagcccc ggcatcctgt ccatggcgaa    420

cgccgggccc aacactaacg ggtcccagtt cttcatctgc accgtgccct gcagctggct    480

ggacgggaag cacgtcgtgt tcggccgcgt cgtcgagggc atggacgtcg tcaaggccat    540

cgagaaggtg ggatcccgcg gcgggagcac cgccaagccg gtcgtcatcg ccgactgcgg    600

ccagctctcc tagatctgtg ctgttcccct tcgcctttcg ccagtatcag tcgtcttgag    660

tcgtcgagtc cctaaataag gaggaggtgg tggtggtgtt agtcttttta tgagttcgtg    720

tcgtgttggt gagatgagat cgcccatggt ttggttggat taggcggagt tcttggatcg    780

attcggtgga gttggatctg cgatccttct tggggttggt tttaaatctt aattcgtgtc    840

gctgcttcta tgatatcgct atcaatcaat gagaacattt gggatcc                 887
```

<210> SEQ ID NO 24
<211> LENGTH: 1650
<212> TYPE: DNA
<213> ORGANISM: Oryza sativa
<220> FEATURE:
<221> NAME/KEY: misc_feature
<223> OTHER INFORMATION: LOCUS: AK107343; 1650 bp mRNA linear PLN 04-DEC-2008; DEFINITION: Oryza sativa Japonica Group cDNA clone:002-126-G05, full insert sequence.; ACCESSION: AK107343

<400> SEQUENCE: 24

```
acatcaatta gcttaagttt ccataagcaa gtacaaatag ctatggcgag ttccgttttc     60

tctcggtttt ctatatactt ttgtgttctt ctattatgcc atggttctat ggcccagcta    120

tttaatccca gcacaaaccc atggcatagt cctcggcaag gaagttttag ggagtgtaga    180

tttgatagac tacaagcatt tgaaccactt cggaaagtga ggtcggaagc tggggtgact    240

gagtacttcg atgagaagaa tgaattattc cagtgcacgg gtacttttgt gatccgacgt    300

gtcattcagc ctcaaggcct tttggtacct cgatacacaa atattcctgg cgtggtctac    360

atcatccaag ggagaggttc tatgggttta accttccccg gttgccctgc gacttaccag    420

caacaattcc aacaattttc atctcaaggc caaagtcaga gccaaaagtt tagagatgag    480

caccaaaaga ttcatcaatt taggcaagga gacattgttg cactcccagc tggtgttgca    540

cattggttct acaatgatgg tgatgcacct attgttgccg tatatgttta tgacgtaaac    600

aacaacgcca atcagcttga acctaggcaa aaggagttcc tattagccgg caacaacaat    660

cgggctcaac aacaacaagt atatggtagc tcaattgagc aacactctgg gcaaaacata    720

ttcagcggat ttggtgttga gatgctaagt gaggctttag gcatcaacgc agtagcagca    780

aagaggctac agagccaaaa tgatcaaaga ggagagatca tacatgtgaa gaatggcctt    840

caattgttga aaccgacttt gacacaacag caagaacaag cacaagcaca agatcaatat    900

caacaagttc aatacagtga acgacagcaa acatcttctc gatggaacgg attggaggag    960

aacttttgca cgatcaaggt gagagtaaac attgaaaatc ctagtcgtgc tgattcatac   1020

aacccacgtg ccggaaggat aacaagtgtc aatagtcaga agttccccat ccttaacctc   1080

atccaaatga gcgctaccag agtaaaccta taccagaatg ctattctctc gccgttctgg   1140

aacgtcaatg ctcatagttt ggtctatatg attcaagggc gatctcgagt tcaagtcgtt   1200

agtaactttg gatagactgt gtttgatggt gtccttcgcc caggacaatt attgatcatt   1260

ccgcaacatt atgctgtctt gaagaaagca gagcgtgaag gatgccaata tatcgcaatc   1320
```

```
aagacaaacg ctaacgcctt cgtcagccac cttgcaggga aaaactcagt attccgtgcc   1380

ttgccagttg atgtagtcgc taatgcgtat cgcatctcaa gggagcaagc ccgaagcctc   1440

aagaacaaca ggggagaaga gcacggtgcc ttcactccta gatttcaaca acaatactac   1500

ccaggattat cgaatgagtc cgaaagcgag acctcagagt aatgtaattg agaactagta   1560

tcggcgtaga gtaaaataaa acaccacaag tatgacactt ggtggtgatt ctgttcgata   1620

tcagtactaa ataaaggtta caaacttctt                                    1650


<210> SEQ ID NO 25
<211> LENGTH: 1556
<212> TYPE: DNA
<213> ORGANISM: Oryza sativa
<220> FEATURE:
<221> NAME/KEY: misc_feature
<223> OTHER INFORMATION: LOCUS: AK063995 1556 bp mRNA linear PLN
      04-DEC-2008; DEFINITION: Oryza sativa Japonica Group cDNA
      clone:001-124-E11, full insert sequence.; ACCESSION: AK063995

<400> SEQUENCE: 25

atcacctgct ctctgcaaac actgtgactt tgggtgagtg agtgagtgag tgaagaggag     60

gaagatgggg aagggaggga aaggagccga ggcggcggcg gcggcggtgg ccggagccgg    120

tgaggaggag aacatggcgg cgtggctggt ggcgaagaac accctcaaga tcatgccctt    180

caagctcccg ccagttgggc cttatgatgt ccgtgtccgg atgaaggcag tgggcatctg    240

cggcagcgac gtgcactacc tcagggagat gcgcattgcg catttcgtgg tgaaggagcc    300

gatggtgatc gggcacgagt gcgccggcgt gatagaggag gtcggcagcg gcgtgacgca    360

cctcgccgtc ggcgaccgcg tggcgctcga gcccggcatc agctgctggc gctgcaggca    420

ctgcaagggc ggccgctaca acctctgcga ggacatgaag ttcttcgcca cccctcccgt    480

ccacggatcc ctcgccaacc agatcgtgca ccctggtgat ctgtgcttca agctgccgga    540

gaacgtgagc ctggaggaag gcgccatgtg cgagccgctg agcgtgggcg tgcacgcgtg    600

ccgccgcgcc gacgtcgggc cggagacggg ggtgctgatc atgggcgcgg ggccgatcgg    660

cctggtcacc ctgctggcgg cgcgcgcgtt cggcgcgacg cgcgtcgtga tcgtggacgt    720

ggacgaacac cgcctctccg tggcccgatc cctcggcgcc gacgccgccg tgagggtgtc    780

ggcgcgcgcg gaggacgtcg gcgaggaggt ggaacggatc agggcggcga tgggcgggga    840

catcgacgtg agcctggact gcgccgggtt cagcaagacg gtggcgacgg cgctggaggc    900

gacgcgcggc ggcgggaagg tgtgcctcgt cgggatgggg cacaacgaga tgacggtgcc    960

gctgacgtcg gcggcgatca gggaggtgga cgtggtgggg atattccggt acaaggacac   1020

gtggccgctc tgcatcgagt tcctccgcag cggcaagatc gacgtgaagc cgctcatcac   1080

ccaccgattc gggttctcgc aggaggacgt ggaggaggcg ttcgaggtca gcgcccgtgg   1140

ccgcgacgcc atcaaggtca tgttcaacct ctagatcgat ccatccatcg atcgatcgac   1200

agcaaaatat gtgacgggtt tggaacgtat gtcgatcgga caaaaaaatg tgtgcttgct   1260

ttgctggttg ccgtgtctgt ctgtctctac atgaataaaa ggcggcaacg ttctgtcctc   1320

atggactaag cgtgtgcatt gtctgtttca attcattcga tggttgttga acactagggg   1380

tgggaggggg gaaatcgaaa ctcgcagctc ggatcggctt gtagcaagtt cggcttggat   1440

cagcttggac tcgtaatctt aatgagtcga gctgagctag ccttttaact catgagctgc   1500

tcgtttaact cgttagtaca agatataacc aaaccttcgt aaacttggtg cttttt       1556


<210> SEQ ID NO 26
```

```
<211> LENGTH: 831
<212> TYPE: DNA
<213> ORGANISM: Oryza sativa
<220> FEATURE:
<221> NAME/KEY: misc_feature
<223> OTHER INFORMATION: LOCUS: AK108210 831 bp mRNA linear PLN
      04-DEC-2008; DEFINITION: Oryza sativa Japonica Group cDNA
      clone:002-140-D09, full insert sequence.; ACCESSION: AK108210

<400> SEQUENCE: 26

accattttca ctcactcact cacactgaac tcctatggcc tccgccgtcg tagccaagcc      60

accggccgcc gctccggcga gccgccgccg atgcttcgtc ttcgtagagc gcgccgccgc     120

cgccgccgtc ggcgtcaacg cggcgatcgc tgccgtcgat gaccaccgcc cagttccggc     180

cgcggccgcc gccgccatgg acgacgtcgt cggccgcgtc gcgcggcctg cgcgccccag     240

cgcgcgcgcc atcatggagg ggacgcacaa gcagatcagc tccggcggcg cctcgggcgg     300

ctactgcacc gtgccgtggt gcagcatctg caccgggaat aacccgttcg ccattgccga     360

gttcttgctg tgctgcaacc tctgcggcgt ccctctcgcc ggccgcccca gcttcatcta     420

cattggagag aaggcgttct gcaaggagga gtgcaggtcg aggtacgtgg tggaggaggc     480

gctgcgcgag gcgagggagg agaagcgccg cgccgccgcc gccgccgccg cgtcgccgga     540

gaagaagaag gaggcggcgg cggcgaggaa gggcggggag gagtgcaggg aggggagcat     600

cttcttcatc tgcgccgacg acctgtgaag aatgtgatgg atatgatgca tcatgcgtgc     660

attgcatggc ggatgataat cggagcttgg ctgtaataat aatcgatctc caccataata     720

taatacaata gtaatatact tagtgtactg taatgaggat gaataaaggg gatcaaatca     780

aggccaccat gcatggctag tcgatatata tctgagtatt ttgtgttgct c              831


<210> SEQ ID NO 27
<211> LENGTH: 1344
<212> TYPE: DNA
<213> ORGANISM: Oryza sativa
<220> FEATURE:
<221> NAME/KEY: misc_feature
<223> OTHER INFORMATION: LOCUS: AK242579 1344 bp mRNA linear PLN
      04-DEC-2008; DEFINITION: Oryza sativa Japonica Group cDNA,
      clone:J090009I07, full insert sequence.; ACCESSION: AK242579

<400> SEQUENCE: 27

ttggatcatc gaatctcgca ccgccactgg aacttgccaa cccgagaatg acggcattcc      60

aggacaacac catggccaat gggacggcac cgccgatcag tattgcgcgc cgcgcatcgt     120

acactgaatc ccccacaatc ttgcagatga acggcgtgat gacatggaac ccaagcgtca     180

ggacggtcac cggaattgca ggcaggatgg tagcagggcg ccagcaggcg tagccgagcg     240

atctcagcat gctgctccgg ccgacggaaa cgccggtgac aacaagcgcg gtgatggagg     300

cgagcatcag gccgcagagc gcgcggttgg cgccgtcgac ggccttgaag ggaagaacg      360

cgatgagcgt cccggcgaag cacgggaaga tggcgttggc caaggccgga tccaccgccg     420

ggaagagctg ggacaccagc gagccgatgc cggcgacgca ggcgacgagc agggagaagc     480

tgagggcggc gtagacgacg gccacgaccg ccccgagcgt cgcccccaag gtgctcgacg     540

caagtcccgt gaagctgacc tcgtcgacgc cgccgtcctc catcgcggcg aagctgagct     600

ccgcgacgag gacgatggag gacaccacgt agacccacga gagcacgatc gccgccgtgg     660

acgggaccgg cccggagcgg atggtggcgg acggcagccc cagcatcccc ggccccaccg     720

ccgttccgac gatgaggctc accgccgccc agaagctctt cttctcccct ccaccggata     780

ccccgtcctc gacgagcggc gccggtgatt cttcttcggc ggcgtcggcg tcgccgtagt     840
```

```
cgctccgcca ccgccattgc cgcctcggcg acagccagga cagcggcaac ggctgcggct    900

gcggcggcgc ggggttcttg gaagctagtg gcggagggcg acgcgttcgt ggctccggga    960

ggccgaggcg gcggcggcgg cggagcggag aggggcaggt tgccggcgag gagggcgtgg   1020

cgaggtggag gcggctggag agtaacatgg tcaacggtaa attttggtag ggtcaaagga   1080

ggcgggtgaa ttctgggcct cttttaccat tcgaggccca gtttttcaac atacgagttt   1140

ctaaaacatt ttggattggg aatttgaaga atgaataata atacgtagta caaactgagc   1200

ggattcatgt aaaaaaatac tgtaaaattt ctgcgtccta atggagcctc agcaaggcct   1260

tggaagattt gggattagag aaattaatat ggctgaattt acgtttccat tgaaacggaa   1320

gaattttagt gaattttcat tatc                                          1344
```

<210> SEQ ID NO 28
<211> LENGTH: 2078
<212> TYPE: DNA
<213> ORGANISM: Oryza sativa
<220> FEATURE:
<221> NAME/KEY: misc_feature
<223> OTHER INFORMATION: LOCUS: AK065456 2078 bp mRNA linear PLN 04-DEC-2008; DEFINITION: Oryza sativa Japonica Group cDNA clone:J013025D11, full insert sequence.; ACCESSION: AK065456

<400> SEQUENCE: 28

```
gggcggtctc ctctccattt ttttcctcct atcgattttg caatttagcc cctagggagg     60

cagggaatcc ggctccggtc cctgtgccgc tcccccccggc tctccttgcc tcccttgctc   120

ctccgatcga ggctgaagcg gcttcaggat atacattttt gtgggaatgg ggaattcttg    180

ccaaaatgga acctatggga acaattacca gaacagcaac cggtttcaga atgaccgttt    240

tgcttctcgg tacgttgatg ggaatgatac tgaggattgc tactcgggct cgtcaagggc    300

cagcttagcg ggtgctctgc ggcaagggct gaacctaaag tcccctgtcc ttggatacaa    360

gactccaaat gtaagggagc tctatactct tggccgggag cttggacagg gacagttcgg    420

gaaaacatac ctctgcactg agattagcac agggtgtcaa tatgcatgca agactatctt    480

aaagagtaat ctccgatgtg tgtcagatat cgaggacgtg cgccgtgaaa tccagataat    540

gcaccatctt tcgggccaga agaatatagt gacaatcaag gacacatatg aggatgagca    600

ggccgtgcac atcgtcatgg agctctgtgc aggtggtgag ctcttcagca agattcagaa    660

gcgaggtcat tacagtgaac ggaaggctgc agagcttata aaaattatag ttggcatcat    720

agaaacatgc cattcacatg gagtgatgca ccgggatctc aagccagaaa atttcctctt    780

actggacgca gacgatgaat tctcggttaa agcaattgac tttggtctat ctgtgttctt    840

cagaccaggt caggttttca gagaggtagt gggaagtcca tattatattg ctccagaggt    900

attggagaag cgttatggac cagaggctga tatatggact gctggagtga ttctctatgt    960

attgctgact ggtgttcctc cattttgggc agatacacaa agcgggatat atgaaaaagt   1020

actggatgga cgtattgatt ttaaatcaaa ccggtggccc aggatatctg acagtgcaaa   1080

ggatcttata aaaaagatgc tctgccctta tccatcagag cgtttgaaag cccatgaagt   1140

gctaaagcat ccatggatat gtgataatgg agtggctact aatcgagctc tggatccaag   1200

tgtacttcct cgtctcaagc aattttctgc aatgaatagg ttaaagaaat tgtctctcca   1260

gattattgct gagcgtcttt cagaagagga gattgttggg ttaagagaaa tgttcaaggc   1320

tatggacacc aaaaacagaa gtgtggttac atttggtgag cttaagggac tgaaaagata   1380

cagctcagtg ttcaaggata ctgaaattaa cgacttaatg gaagcagctg atgacaccac   1440
```

```
ctctaccatc aactgggaag agtttattgc tgcagcagtg tctcttaata aaatagaacg   1500

tgagaaacac ttgatggcag cctttacata ctttgacaaa gatggaagtg gttttatcac   1560

agttgacaag cttcaaaagg cttgcatgga acgtaacatg gaagatactt tccttgaaga   1620

gatgattctg gaggttgatc aaaacaatga tggtcaaatc gattatgctg aatttgtcac   1680

aatgatgcaa agcaacaact ttggacttgg gtggcaaacg gtggaaagca gcctgaatgt   1740

agccctgagg gaggcacccc aagtatactg aactcctgtc gcctggcacc cccaagaatt   1800

cagtttgttc tcctgagcct ttcatctgtt tatcacaaca catagttgtg gatttgagag   1860

aagagagcca agactagatg gtttatcagt aatcacccta tagcagtggt ggaagaagac   1920

tctcttagta cctaatagca tataaatgtg tggtctaaag acatcgtata tgtatgaacc   1980

tcataagttc gttcgttcgt tcgtttggtt ggttggtttg ctaccctgct atctaataat   2040

aatatcaata atacccgaag aacccctctt ggttctgc                           2078
```

<210> SEQ ID NO 29
<211> LENGTH: 729
<212> TYPE: DNA
<213> ORGANISM: Oryza sativa
<220> FEATURE:
<221> NAME/KEY: misc_feature
<223> OTHER INFORMATION: LOCUS: AK107633 729 bp mRNA linear PLN 04-DEC-2008; DEFINITION: Oryza sativa Japonica Group cDNA clone:002-131-E06, full insert sequence.; ACCESSION: AK107633

<400> SEQUENCE: 29

```
aaaaattaaa ttttctaaat tacaagcaaa tcaaagctca tcgaagtata gctatggcat     60

tggcatcaga caagttcgtc ctctccgcca tcgtgctcgc cgtcctcacc gtcgcggcag    120

cggcggcggg ctacggcggc tacggcgacg tcggcgagta ctgccgcgtg gggaaggcgg    180

tgtcccggaa cccggtccca tcgtgccgga actacatcgc gcggtggtgc gccgtcgccg    240

ggggccgcct ggactccggc aagcagccgc cgcggcagct cctggagccg tgctgccggg    300

agctcgccgc agtgccgatg cagtgccggt gcgacgcgtt gagcgtgctg gtgcgtggcg    360

tggtcacgga ggagggcgac cgcgtcgccg ggatgatctc gcagcacgcg gcgcccgggt    420

gcgacgccgc gacgatcgcc gggatggcga gcgcgctgac ggactacggc cggtgcaacc    480

tgcagcacac tggtttcttt ggctgcccca tgtttggggg tggcatggat taacttcctt    540

agtaattaat taattaggcc tttgcttaat taattattta attagttatc cgggttactg    600

gataattaat tatcgatatt tgctagtagc atctatcatg tttggatgct gctttctccg    660

tgaatgtgat gataataata atcagaagaa ataaataaga agagttggat tcatcagctt    720

tccagtatc                                                            729
```

<210> SEQ ID NO 30
<211> LENGTH: 1507
<212> TYPE: DNA
<213> ORGANISM: Oryza sativa
<220> FEATURE:
<221> NAME/KEY: misc_feature
<223> OTHER INFORMATION: LOCUS: AY196923 1507 bp mRNA linear PLN 02-AUG-2005; DEFINITION: Oryza sativa (japonica cultivar-group) glutelin precursor, mRNA, complete cds.; ACCESSION: AY196923

<400> SEQUENCE: 30

```
gctatggaaa ctatggcatt ctctcgattt tctatatgct tttgtgtcct tctcctttgc     60

catggttcta tggctcagat atttagtcta ggcataaatc catggcaaaa tcctcgacaa    120
```

```
gggggttcta gggagtgtag gtttgatagg ctccaagcgt ttgagccgct taggaaagtg     180

aggcatgaag ctggggttac agagtacttt gatgagaaga atgagcagtt ccagtgcacc     240

ggtacattag taattcgtcg cattattgag cctcagggcc ttcttttacc tcgatactcc     300

aacactcctg gcctagtata tatcatccaa gggactggtg tactgggatt gacctttcct     360

ggttgcccag caacttacca aaagcaattt aggcattttg gtcttgaagg aggaagccaa     420

aggcaaggaa aaaaattaag agatgaaaac caaaagatcc accaatttag gcaaggagat     480

gttgttgcac ttccttctgg tataccacac tggttctata atgagggtga cacccctgtt     540

gttgctttgt ttgtttttga tgtaaacaac aatgctaatc aactcgaacc aagacaaaag     600

gagttcttgt tagctggtaa caatatagag caacaagtgt ccaacccctc aatcaacaaa     660

cattctgggc aaaacatatt caatggattc aacactaagc tattaagtga ggccttaggc     720

gttaacatag aggtgaccag aaggctacaa agtcaaaatg accgaagagg agatatcatt     780

cgagtaaaga atggccttcg attgataaaa ccaactatca cacaacaaca ggaacaaaca     840

caagatcaat acccaccaat tcaatatcat agagagcaac gatcaacaag caaatacaat     900

ggcttggatg agaacttctg tgcaattagg gcaaggttaa acatagaaaa ccctaatcat     960

gctgatactt acaaccctcg tgctggaagg attacaaatc tcaatagcca gaagttctcc    1020

attcttaacc ttgtccaaat gagtgctaca agagtaaatc tataccagaa tgctattctc    1080

tcaccattct ggaatattaa tgctcacagt ttggtgtata caattcaagg gcgtgctcga    1140

gttcaggttg ttagcaacca tggaaaggct gtatttaatg gtgttcttcg tccagggcaa    1200

ttactaatta taccacaaaa ttatgtggtt atgaagaaag cagagcttga aggatttcaa    1260

tttatcgcgt ttaagacaaa cccaaatgcc atggtaaacc acatcgcggg gaagaactca    1320

gttctccgtg caatgcctgt ggatgtgata gctaatgcat atcgcatctc aaggcaggaa    1380

gctcgtagct tgaagaataa taggggagaa gagattggtg ctttcactcc tagatatcaa    1440

caacaaaaaa tccaccaaga gtactcaaat ccaaacgaaa gtgagactca agaggtgatt    1500

taagccc                                                              1507
```

```
<210> SEQ ID NO 31
<211> LENGTH: 264
<212> TYPE: DNA
<213> ORGANISM: Oryza sativa
<220> FEATURE:
<221> NAME/KEY: misc_feature
<223> OTHER INFORMATION: LOCUS: OSU43530 264 bp mRNA linear PLN
      05-FEB-1997; DEFINITION: Oryza sativa metallothionein-like type 2
      (OsMT-2) mRNA, complete cds.; ACCESSION: U43530

<400> SEQUENCE: 31

tttgaaagaa agatgtcgtg ctgcggagga aactgcggct gcggatccgg ctgccagtgc      60

ggcagcggct gcggaggatg caagatgtac ccggagatgg ctgaggaggt gaccactacc     120

cagactgtca tcatgggtgt tgcaccttcc aagggtcatg ccgaggggtt ggaggccggc     180

gccgccgccg gagcaggagc agagaacggg tgcaagtgcg gcgacaactg cacctgcaac     240

ccctgcaact gcggcaagtg aagc                                            264
```

```
<210> SEQ ID NO 32
<211> LENGTH: 1065
<212> TYPE: DNA
<213> ORGANISM: Oryza sativa
<220> FEATURE:
<221> NAME/KEY: misc_feature
<223> OTHER INFORMATION: LOCUS: AK064310 1065 bp mRNA linear PLN
```

04-DEC-2008; DEFINITION: Oryza sativa Japonica Group cDNA clone:002-107-B12, full insert sequence.; ACCESSION: AK064310

<400> SEQUENCE: 32

```
acactaccca gctcactgaa gtagcaacgc agctcatcag tgtcaagatg gctactacta     60

agcatttggc tcttgccatc cttgtcctcc ttagcattgg tatgaccacc agtgcaagaa    120

ccctcctagg ttatggcccc ggaggaggag gtggaggtgg tggtggtggt gaaggaggcg    180

gtggtggtta cggtggatcg ggctatggtt ctggttctgg gtatggtgag ggaggtggta    240

gtggaggtgc tgccggtggc gggtatgggc gtggtggagg cggcggcggc ggtggtggtg    300

agggtggtgg ctccggctct ggctatgggt ctgggcaagg ctctggctat ggtgcaggtg    360

ttggtggtgc tggcgggtat ggtagtggtg gcggaggtgg tggtggccaa ggtggtggtg    420

ctggcggcta cgggcaaggg tctggctatg gttccggcta tgggtcgggt gctggtggtg    480

ctcatggtgg tggttatgga agtggtggcg gtggcggtgg cggtggaggc caaggtggag    540

gctccggctc tggctctggc tctggatatg gctctggctc tggcggaggc aacggacacc    600

actaagctca tttcctctat cagctagcta caatatagcc tgttgttata agtgaaccgt    660

gatcagtgat gagtctctct cgctgcttta caaagagctt gtcggattgt atcgatatag    720

cactgtgtac tggcttgccg tttcatcaca taaagttggc aaagcctagt aaataaaacg    780

acctttgta ctcagatcat acttctgtta ttcacggagc tgatgttcac taagattgat    840

atgcaagaac atagatttaa cccttgtcct agctagttgt ttacatagta agcatgcaga    900

atggacttgt taactctcgg tgatcttgag ttgtaaactg gacttgttct cagtagggct    960

gctagctagc atttctagat tccaacatgt tcgcttacac ggtgttaaaa aaatattgct   1020

gcagattgta atgagactac ccagataaag tttcaattgg tcagc                   1065
```

<210> SEQ ID NO 33
<211> LENGTH: 1139
<212> TYPE: DNA
<213> ORGANISM: Oryza sativa
<220> FEATURE:
<221> NAME/KEY: misc_feature
<223> OTHER INFORMATION: LOCUS: AK064485 1139 bp mRNA linear PLN 04-DEC-2008; DEFINITION: Oryza sativa Japonica Group cDNA clone:002-111-B07, full insert sequence.; ACCESSION: AK064485

<400> SEQUENCE: 33

```
catctttact aaagaagatg gtaaaatttt agataagcgt gtcacagacc ttcagttgga     60

agacttcctg ctatatggcc cacaaaatga gcagggaaag ggtggaaaac ccttgctacg    120

gaaactgaaa gatggtcgga tagtgaattg gaatgtgcag tcagatgacc ctctttgcac    180

acttcaagaa gctttcgaga aggtcaatcc tagattgggc ttcaatattg agctcaaatt    240

tgatgacaat cttgaatacc aggaggaaga gctcacttgt atcctccagg ccatcctgaa    300

ggttgttttt gagtatgcca aggatcggcc tattattttc tctagcttcc agcctgacgc    360

tgcacaggtt atgcgaaaat tgcaaagcac ataccctgtt tactttttga ctaatggagg    420

cacagaaatc tacgctgacg ttaggaggaa ctcattggaa gaggccatca agctatgcct    480

cgccagcggc atgcaaggaa tcgtgtcgga ggcacgagga attttcaggc accccgctgc    540

tgtaccaaag atcaaagagg ctaacctctc cctactgact tatggaacac tgaacaacgt    600

accggaggcg gtgtacatgc aacatctgat gggggtgaac ggtgtgatcg tcgacctagt    660

gcaggagatc accgaggccg tctctgagct catcaccgtc ccggagcctg acctgaacgc    720

cgataatttg agcaatgggg cagcaaaaga cgccgcaacg ccacatttct cgcagtgtga    780
```

```
aatctcattc ttgctgaggc tcatccctga gcttgtgcaa taatcgatcc agttgccttg    840

ctggtctgca gactttagtg actgatctgt atacaggaag aagaggagag acccccttgtg   900

gagggttaca agtttacaaa acttttaaat aggttgatgt actagagcta agccctggtc    960

ctgtttttta atttgccctg gggacgtttg gattcatgat ggatcatgga tgatgcatcc   1020

tgtagcaagg agttgaaaca gttgttgtta ctgttgtatc tgtaagactg taacgacgac   1080

ctatttgggt ggagttgaat tgcaatgcgg aatttggcaa aaaaaaaaaa aaaaaaaag    1139


<210> SEQ ID NO 34
<211> LENGTH: 957
<212> TYPE: DNA
<213> ORGANISM: Oryza sativa
<220> FEATURE:
<221> NAME/KEY: misc_feature
<223> OTHER INFORMATION: LOCUS: AK101309 957 bp mRNA linear PLN
      04-DEC-2008; DEFINITION: Oryza sativa Japonica Group cDNA
      clone:J033033N23, full insert sequence.; ACCESSION: AK101309

<400> SEQUENCE: 34

ggttcgatcc aagaagcaga gaggagaggg attcttgttt tcttgatcat ccatggcgcg     60

gctgcggcgt ggtctcgaac acctggggcg gcggtacgcg ttctacgcgg cgtaccactc    120

caacccggcg aacgtgctcg tccacgccgt gtgcgtgtgg cccatcctcc tcaccgcgat    180

gctcccgctc cggtacgcgc cgccgctgcc gctgctccga ttctactgcc cgctctgccg    240

ccagtacctc cccgtgcagc tcggcttccc cgtcgccgtc gcgctgggcg cgtactacgc    300

gctcatggac cgccgcgcgg gcgccgccgc cgcggcgctc tgcgtcgccg ggtgggccgc    360

cgggacgctc ctcgccgacg ccgcggggct ctggacgttc cgcgacgcgt ggaggccgct    420

gctcaccgcg caggccgtgc tctggtccgc ccagttcttc tcccacgcct tcttcgagaa    480

gcggcggccg gcgctggtgg atggcccggt gcaggcggtg gtgacggcgc cgctgttcgt    540

cttcatcgag gtaattggcc gtgttcgttc gagttggtcg ccgtgcggcg atggcgaccg    600

ccaagtgttc gatttaatgc gagtgcggtt gctccgtgtt tttgcaggtg ctgcataggt    660

tgttcgggta cgagccgacg ccggggttct acaagcgcgt ccaggcgagg gtggcggcga    720

tgcacaacgg gccgccggca ccggcgccgg cgccggagaa gaaggaggag gaggagaagg    780

agaacgtgag caaggcgacg caggaggaga gcgccgagaa ggattcgtag gtgttttcga    840

gggagagtgt gacagacagg agaggcagag ctcgggatgt tatgaacttg taatagcttg    900

ttcatgtata gtagtagtat aataataata ctaagaaaat aaatgagttt aattttc       957


<210> SEQ ID NO 35
<211> LENGTH: 630
<212> TYPE: DNA
<213> ORGANISM: Oryza sativa
<220> FEATURE:
<221> NAME/KEY: misc_feature
<223> OTHER INFORMATION: LOCUS: AK107983 630 bp mRNA linear PLN
      04-DEC-2008; DEFINITION: Oryza sativa Japonica Group cDNA
      clone:002-135-E08, full insert sequence.; ACCESSION: AK107983

<400> SEQUENCE: 35

aacacagttc atcggcatct tctcacactc tagctcacag cttcgcggtt tccacgcact     60

tgaaaactca cgtttccaag ccggaaaacc atggctcgct tcgccgtagt cgccgccatc    120

gtcgccctcc tcgcggtcac ggccgccgcg caggccccgg gagcggcccc cgtcccggcg    180

cccaagatgg ccccgctgcc cgctccccccg gcgaggtccc cggccaccgc ccccgcgccg    240
```

```
gtcgccaccc cgcccaccgc cgcgtcgccg tcccccatgg cgtctccacc ggccccgccc    300

actgacgccc ccgccgccaa tgccccctcc gccgtcaccc cgtccgcggt caccccctcc    360

tccgtctccg ccccgaccgg cgccccccgct gcctcctcca cgtacaccgc caccgccagc    420

ttcgttgccg tcgccggcgc ggtcgccgcc gccatcgtgt tctagatgga tggatggatg    480

atttgatcga cgcgttgttt atacggcgag attctttttt gtgattctgt tctatttaca    540

gacagcgaga cactgatatt cagatgttta cacttgtcat gtttgatgag atgattatcg    600

atggaatata ttctttcatt tattattacc                                    630
```

```
<210> SEQ ID NO 36
<211> LENGTH: 1412
<212> TYPE: DNA
<213> ORGANISM: Oryza sativa
<220> FEATURE:
<221> NAME/KEY: misc_feature
<223> OTHER INFORMATION: LOCUS: AK099918 1412 bp mRNA linear PLN
      04-DEC-2008; DEFINITION: Oryza sativa Japonica Group cDNA
      clone:J013116J24, full insert sequence.; ACCESSION: AK099918

<400> SEQUENCE: 36

gactcacaca cactctcctc atcccagagc aagaagctca gctcctcctc ctctcgcatg     60

gcagccatgg ccaccaccgc gtccagcctc ctcaagacct ccttcgctgg cgcgcgcctc    120

cccgccgccg cccgcaaccc caccgtctcc gtcgcgccgc gcaccggcgg cgccatctgc    180

aactccatct cgtcgtcgtc gtccactccc ccctacgacc tcaacgccat caggttcagc    240

cccatcaagg agtccatcgt gtctcgcgag atgacccggc ggtacatgac cgacatgatc    300

acctacgccg acaccgacgt cgtcgtcgtc ggcgccggct ccgcggggct ctcctgcgcg    360

tacgagctct ccaaggaccc ctccgtcagc gtcgccgtca tcgagcagtc ggtgtccccc    420

ggcggcggcg cgtggctcgg cgggcagctg ttctccgcca tggtggtgcg caagccggcg    480

cacctgttcc tcgacgagct cggcgtcgcg tacgacgagc aggaggacta cgtcgtcatc    540

aagcacgccg cgctcttcac ctccaccgtc atgagccgcc tcctggcgcg ccccaacgtg    600

aagctgttca acgccgtcgc cgtcgaggac ctcatcgtca aggagggccg cgtcggcggc    660

gtggtcacca actgggcgct ggtgtcgatg aaccacgaca cgcagtcgtg catggacccc    720

aacgtgatgg agtccagggt ggtggtgagc tcctgcggcc acgacgggcc gttcggcgcc    780

acgggcgtca agcggctgca ggacatcggc atgatcgacg ccgtgcccgg catgcgcgcc    840

ctcgacatga acaccgccga ggacgagatc gtccgcctca cccgcgaggt cgtccccggc    900

atgatcgtca ccggcatgga ggtcgccgag atcgacggcg ccccgagaat gggcccgacg    960

ttcggagcca tgatgatctc cggccagaag gcggcgcacc tggcgctgaa ggcgctcggc   1020

cggccgaacg ccatcgacgg cacgatcaag aaggcggcgg cggcggcggc gcacccggag   1080

ctgatcctgg cgtcgaagga cgacggcgag atcgtggacg cctgagcgaa tagaacaggg   1140

taaaaaaaaa tccgcaagac gtggtggtga cacggaggag ttggggacga gaagaagatg   1200

tggactttcc cctgtgtttt tttttcggga tttgcattga tccccttgtt tgttttagct   1260

ctggatgttg attagcgtct tgttcatagc acttccactg ccaccgtgtg tgtgtgctct   1320

gcttgcctga tgagggcaag aaaacttcca tggatccgtc tctctgggag gaatgaataa   1380

aaaggatgag gaaataaaaa tgattcagtg cc                                 1412

<210> SEQ ID NO 37
<211> LENGTH: 2771
<212> TYPE: DNA
```

```
<213> ORGANISM: Oryza sativa
<220> FEATURE:
<221> NAME/KEY: misc_feature
<223> OTHER INFORMATION: LOCUS: AK100306 2771 bp mRNA linear PLN
      04-DEC-2008; DEFINITION: Oryza sativa Japonica Group cDNA
      clone:J023078G01, full insert sequence.; ACCESSION: AK100306

<400> SEQUENCE: 37

gagcatccat cggttctctg ctctgttcat ccatagagtt tcctcctctt ctcctttagt     60

gcaaggcttg aggatccatc tagaagatag caatggggga aactactgga gaacgtgccc    120

tgacccgtct ccacagcatg agggagcgca tcggcgattc cctctccgcg cacaccaatg    180

agcttgtggc tgtcttctca aggcttgtga accaaggaaa gggaatgcta cagccccacc    240

agatcattgc tgagtacaac gccgcaatcc ctgagggcga gcgtgagaag ctgaaggact    300

ctgccttaga ggatgtcctg aggggagcac aggaggcgat tgtcatccct ccatggattg    360

cccttgccat tcgcccaagg cctggtgtct gggagtatct gaggatcaat gtaagccagc    420

ttggtgttga ggagctgagt gtccctgaat acttgcagtt caaggagcag cttgtggatg    480

gaagcaccca gaacaacttt gtgcttgagc tggactttga gccattcaat gcctccttcc    540

ctcgcccatc gttgtcgaag tctattggca atggggtgca gttcttgaac aggcacctgt    600

cgtcaaagct gttccatgac aaagagagca tgtacccccct gctcaacttt cttcgtgcgc    660

acaactacaa agggatgacc atgatgttga acgacaggat tcgcagtctc gatgctctcc    720

aaggtgcatt gaggaaggca gaaaaacatc ttgcaggcat tacagctgac accccatatt    780

cagagttcca tcacaggttc caagagcttg gtttggagaa gggttggggt gactgcgctc    840

agcgagtgcg tgagactatt caccttctct tggaccttct tgaggcccct gagccgtccg    900

ccttggagaa gttccttgga acaatcccaa tggtgttcaa tgttgttatc ctctccccgc    960

atggttactt tgcacaggct aatgtcttgg ggtaccctga taccggtggg caggttgtct   1020

acattttgga tcaagtccgt gctatggaga atgagatgct gctgaggatc aagcaacaag   1080

gtctaaacat cacaccaagg attctcattg tgaccaggtt gctacctgat gcgcatggca   1140

ccacatgtgg ccagcgcctt gagaaggtcc taggcactga gcacactcat atcctgcgtg   1200

tgccattccg aacagaaaat gggactgttc gcaaatggat ctcgcgtttt gaagtctggc   1260

cttacctgga aacttacacc gatgatgtgg cacacgagat ttctggagag ctgcaggcca   1320

cccctgacct gatcattggg aactacagtg atggcaacct tgttgcatgt ttgctggcac   1380

acaagttggg tgtcactcat tgtacaatcg cccatgcact tgagaaaacc aagtacccca   1440

actccgacct ttactggaag aagtttgagg atcactatca cttctcctgc cagttcacag   1500

ctgacctgat tgcaatgaac catgctgact tcatcatcac aagtaccttc caggagattg   1560

ctggaaacaa ggaaactgtg ggcagtatg agtctcacat ggcattcaca atgcctggcc    1620

tttatcgtgt tgtccatggt atcgatgtct ttgaccccaa gttcaacatc gtctctcctg   1680

gtgctgacat gtccatctac ttcccattca ccgaatcaca gaagaggctc acctctctcc   1740

atttagagat agaggagcta ctcttcagtg atgttgaaaa cactgagcac aagtttgttc   1800

tgaaggacaa gaagaagcca atcatcttct cgatggctag gctagaccat gtcaagaatt   1860

tgactggtct ggttgagttg tatggtcgga accctcgcct gcaagagcta gtaaaccttg   1920

tggttgtctg tggtgaccat ggcaaggaat ccaaggacaa agaagagcag gctgagttca   1980

agaagatgtt taatctgatc gagcagtaca atttgaatgg ccacatccgc tggatctccg   2040

ctcagatgaa ccgtgtccgc aatggtgagc tctaccgcta catctgcgac atgaggggag   2100
```

cctttgtgca gcccgctctc tatgaggcct ttgggctaac tgtgattgag gccatgacct 2160
gtggtcttcc aacatttgca actgcctatg gtggtccagc cgagatcatc gtgcacggcg 2220
tgtctggcta ccacattgat ccttaccaga acgacaaggc ctcggcgctg ctcgtggagt 2280
tctttgagaa gtgtcaggaa gacccaaacc actggatcaa gatctcgcag ggtggacttc 2340
agcgcatcga ggagaagtac acatggaagc tctactctga gaggctgatg actctctccg 2400
gtgtctacgg tttctggaag tatgtcacca acctcgacag gcgtgagaca cgccgctacc 2460
tggagatgct gtacgccctc aagtaccgca agatggctac caccgttcca ttggccattg 2520
agggagaggc ctccaccaaa tgatctggcc ttacccggtg aaaagaatgg gcaatgggtg 2580
ctccattgtt gcagtgctga tccaggggtg aagaaaaaca gaaatcgagg aacgaatgca 2640
tccatttagt ttctaagggt ttagttgatt tcagggccag ttcttgtggg gttttcaatg 2700
gaagaaattg atgtaatgct ctggcctttt catggatact atgaatgaaa taaatgaata 2760
acaagattct c 2771

<210> SEQ ID NO 38
<211> LENGTH: 692
<212> TYPE: DNA
<213> ORGANISM: Oryza sativa
<220> FEATURE:
<221> NAME/KEY: misc_feature
<223> OTHER INFORMATION: LOCUS: X83434 692 bp mRNA linear PLN 09-OCT-1997; DEFINITION: O.sativa mRNA for lipid transfer protein, b1.; ACCESSION: X83434

<400> SEQUENCE: 38
cacagctcct cttggtcgcc ctcgtggcag ctctgctcct ggcgggccca cacaccacca 60
tggccgccat cagctgcggc caggtcaact ccgccgtgtc gccctgcctc agctacgccc 120
gcggcggctc ccgcccgtcg gcggcctgct gcagcggcgt caggagcctc aactccgccg 180
ccaccaccac cgccgaccgc cgcaccgcct gcaactgcct caagaacgtg gccggcagca 240
tcagcggcct caacgccggc aatgccgcca gcatcccctc caagtgcggc gtcagcatcc 300
cctacaccat cagcccctcc atcgactgct ccagcgtgaa ctaatccgat cgatcgctac 360
cggaggatga catgcagcgc cggccgagat gcagctgtcg tctcacgctt tgtatcttgt 420
gttatctgtg tttatgctga ataaaatgag agctagctag ctaggtcgat ccatcgccat 480
gcatacatgg ttgatcgccc ggccggtcac tacgctatct gtttccttaa tttattcgtc 540
gatcgactat acgtacctga gagctagaga tcagtttttg taccatatgc atatgtactt 600
ctgcatgtac atggagtact acttgtacta cgtgcgtgta cgttgtggat tatacataga 660
tatatagctc tttttcgtaa aaaaaaaaaa aa 692

<210> SEQ ID NO 39
<211> LENGTH: 2882
<212> TYPE: DNA
<213> ORGANISM: Oryza sativa
<220> FEATURE:
<221> NAME/KEY: misc_feature
<223> OTHER INFORMATION: LOCUS: AK070414 2882 bp mRNA linear PLN 04-DEC-2008; DEFINITION: Oryza sativa Japonica Group cDNA clone:J023053H09, full insert sequence.; ACCESSION: AK070414

<400> SEQUENCE: 39
gtcatttcat cgaacacctt gcaatcaccc tctcaccacc gctagagatc accattgtga 60
ggctccccgg ccggagctgg aggttggagg gagtggagga agagccgtgc tgccgccgtc 120
gccatggggg aagccaggta gccgctggac atcaagaaac gccgtcgagc accttacatc 180

```
gccgctgtct gcccctgtcc tgcaccgcgt cgagctccac ttcgccgcgt ttcgccatct    240
cgccgtctcg cgaaattgta tatcggttag tcgtgaggca acgtatgcag cttccaggag    300
gtgaaggttg atcaagatca tatcaagaat aagaactatc ctgagcagag tattgaagag    360
aagcccttgt tagtacgctt gcgtacctaa caagatgatc ggagtgcggt tctgttctag    420
gtctcgttcc ccagtcgact gcttgtggca tgtcaactga gcccttgtat tattttgtct    480
tccactgttg tttctctgat agttgttggc ctgcctggcc ctaatgtaag tatttaactc    540
tcttagcctg aattcattcg tgatatgttg tgattcggct atgtatgtgt gtaccaacta    600
ctgatccagg gattggtact gataaacaca gaagatttcc gatttacaaa atcgggggtc    660
gacatgccag atctggcgga ggggagggcc ccgccatgtt gccgcctccc ttcccgctgg    720
atctggcgga gaggagggtg ccgccgcttc cgggccgctt cctcccctcc cgtcggctct    780
ggcatagggg agcacgccgc cgtgctgccg ctggaccacc gcctcccctc ccatcggatc    840
tggcagaggg gagggccccg ccatggtgga tggaggagga ggagaggagt gctgccactg    900
ttgtggatgg aagaggagga gagaggagaa ggaagaaatg gagagaaaga aggaagaaga    960
agagaggagg aagtggattg cgggtgcggg agatagagtt cgagagagag ggaggggagg   1020
aagagataag gatgggagta gatagggtgg ctcagctcgg ctcggttagt tcggcagata   1080
ggtgtcggtt ttaaaaaaac cggcacttat aatatattat aggtctcggt ttttaattaa   1140
ccgacaccta taatatatta cagatgccgg ttttttttctt aaaaaccgac acccatagta   1200
taagtgtcga tttttcttta gaaccaacac ctatagttgt ttaaaggtgt cggttttttt   1260
atgttttcat cccgttgagg tttgaaaaac attatatata ggtgccagtt ttagcacgtc   1320
cggtacctat agtgccgata tatatgtccc tttttgtagt agtgatccct cggaataata   1380
gtaaccaaac aatattctta ttctgcaggt gtgaacaaat taaacttagt tttgtcttga   1440
tcatctgcca actattcttt ttaaggttaa ctgtcgacta ctcgcatttc tcatataccc   1500
atcctcctcg tggaaaacag ttctcctcct agactatgtt tagttcctaa aaaaagttga   1560
aagtttaggg aaagttagta gtttggaaaa aaaattgaaa gttcatgtgt gtaggagaga   1620
tttggatgtg atgtgatgga aagctggaag ttgggggtga actaaacacg gccctagtgt   1680
tctctcgttc cccaaaatta atataaatat atttactctt tctacacatt tacatcaaca   1740
caattcgcaa tatgcgaaga tcgtttcata ttgccttcca cgtgtaccgt aaaaggggag   1800
caaatacagt cgacagtgga tggaggggaa tagctctggt tttcccaaca gccaaccacc   1860
agctgctaag ctagctccca atcgtattga atgaacgtat ggacacatgc accgtttaaa   1920
caccacaaac ccatccttgc tttgttaatt gctcgatctc ttgcagctgc gtgcaccgca   1980
tctgtgcatg catccacact agcaactcta cctatttaag cccctgcatt cccgcgtatt   2040
ctcctcatcc atctcatcag caacgaacca attcacaccg atcgatcgag caacagtagt   2100
aggaaccatg gcccgtgcac agttggtgtt ggtcgccgtt gtggcagctc tgctcctcgc   2160
cgccccgcac gccgccgtgg ccatcacctg cggccaggtc aactccgccg ttgggccctg   2220
cctcacctac gcccgcggcg gcgccggccc gtcggcggcc tgctgcagcg gcgtgaggag   2280
cctcaaggcc gcagccagca gcaccgctga caggcgcacc gcgtgcaact gcctcaagaa   2340
cgcggcccgc ggcatcaagg ggctcaacgc cggcaacgcc gccagcatcc cctctaagtg   2400
cggcgtcagc gtcccctaca ccatcagcgc ttccatcgac tgctccaggg tgagctgagc   2460
tatcgatcgg atggatcatt tatatgcata cagaagcgcg acggtgggtc gatgtgtgga   2520
```

```
gccgatcgaa ttctgtatcc aatattagta gtatctgtac gtattctgga ataaaaagat   2580

gagctagcta aggtcgatca atcaccatgc atgcatgtgt gtgcatccat ggttgatcgg   2640

cccggccggt caggctagct agctttcttc ttcttgtgtg ttcatctcgt acgttttgct   2700

ccttctcgag gtgtacgtgt accagagaga gctagctaga gattctacat gcatgtactg   2760

caactccttg tactacgtgc ttgttttgga atattacaca tacatatagc tctttttggt   2820

acatatatag ctctttgtag agctccacac tagtatagat actctcatct gtgacgtcct   2880

ct                                                                  2882
```

```
<210> SEQ ID NO 40
<211> LENGTH: 984
<212> TYPE: DNA
<213> ORGANISM: Oryza sativa
<220> FEATURE:
<221> NAME/KEY: misc_feature
<223> OTHER INFORMATION: LOCUS: AK103220 984 bp mRNA linear PLN
      04-DEC-2008; DEFINITION: Oryza sativa Japonica Group cDNA
      clone:J033122O18, full insert sequence.; ACCESSION: AK103220

<400> SEQUENCE: 40

gactcacctc ctctgcttct cccaccacct cactacctct cgccgcgaga gcagcagcgc     60

tcgtgttcgg tcaaaagcct cgccgcggcg agctcgagct cattcgcatt ccggagggga    120

gggagggatg ggggacgagt cggaggggga gacggaggag tacctgttca aggtggtgat    180

catcggggac agcgcggtgg ggaagagcaa cctgctgtcc cgctacgccc gcaacgagtt    240

caatctccac tccaaggcca ccatcggcgt cgagttccag acgcagagca tggacatcaa    300

cggcaaggac gtcaaggccc agatctggga caccgccggc caggagcgct tccgcgccgt    360

cacctccgcc tactaccgcg gcgccttcgg cgccctcctc gtctacgaca tctcccgccg    420

ctccaccttc gacaacgtcg gtcgctggct ccaagaactc aacacacatt cggacacgac    480

tgtagccaag atgttggtgg gcaacaagtg tgatctggat aatatccgtg aagtgccggt    540

agaggaaggc aaagcacttg ctgaagctga agggctgttc ttcatggaga cctctgctct    600

ggactcgaca aacgtgagga cagctttcga gatcgtaatc aaggagatct acagcaacgt    660

gagcaggaag atcttgaatt cggactccta caaggcggag ctatccctca atagggtaag    720

cattgagggt gattcgaagg atgatcagaa acagtcaaac cggtttggat gttgctaggg    780

gttttagtac attattatta ttggattcac tgtgatatga aggtttttttg ttcattaata    840

ttattattat tatctgtaaa cttgtaatcc aaattgtttt ttggtttggt tactctggta    900

cacactgtga cactgagata caaagtgaga gaagaatagt tgctggtaat gaatagttga    960

gaggactgct ttgtgctgtt acct                                           984
```

```
<210> SEQ ID NO 41
<211> LENGTH: 2439
<212> TYPE: DNA
<213> ORGANISM: Oryza sativa
<220> FEATURE:
<221> NAME/KEY: misc_feature
<223> OTHER INFORMATION: LOCUS: AK121856 2439 bp mRNA linear PLN
      04-DEC-2008; DEFINITION: Oryza sativa Japonica Group cDNA
      clone:J033102G02, full insert sequence.; ACCESSION: AK121856

<400> SEQUENCE: 41

gccgcctcgt tcgcttctct cttccccttc cttccattcc agctagcaac cgcaagtccg     60

caacgcgaga aacgcaggca gcaaagcaag cgaacccaaa gctggcctcg cactcacact    120

gacagccttg ctctcctcct ccccctatat ctctcctccc tccctcgccg cctcctcccc    180
```

```
aatcctccaa accctaatcc cccacctcac tctctctcga tctcgtgctc tcctcctttc    240
gcgagcgcgt tctttggagg ggagatggcg gaggagccac agccagaggc cgcgcccgcc    300
gcggtggcgg cgacgaccga ggtggcggtg gcggagaagg cgcccgtgga ggcggagaag    360
gagaagaagg tggaggagga gacgccggcg gtggaggccg aggcgaagga ggagaagaag    420
gatgaggcgg cggcggcggc ggcggcggga ggtgatgagg ccggggcgat agaggggacc    480
ggatcgttca aggaggagag caacctggtg gcggacttgc ctgacccgga gaagaaggcg    540
ctcgatgagt tcaagcagct gatcgccgcc gccctcgccg cctgtgagtt caatctgcct    600
ccccctccgc cgcctcccaa ggcgaaggtt gaagccgccg ttgaggagac caaggcggag    660
gagaccaagg ccgaggagga acccaaggct gaggagccgg ccaaggagga ggagcccaag    720
gccgaggtgg cggcggcggc ggcggcgccg ccggaggcag gaaccgagga gccgaaggcg    780
gaggcgtcgt ccgaagaggc caagaccgag gagccgaagg ccgaggcggc ggccgacgag    840
ccggccaagg aggagtccaa agctgaggcg gcgccggctg aggaagccaa gccggccgag    900
ccggagccgg aggagaagac cgtcgtggtc accgaggaag aggcggccac caagacggtg    960
gaagcgatcg aggaaaccgt cgtgcccgct gctgctgcgc ctgctgccgc cgccacggag   1020
gaagccgcgg cgccggaacc ggaggtgcag gcggcggcgg cgcctgagcc cgtgttgatc   1080
tggggcgtgc ccctggtagg cgacgacgag cgcaccgaca cggtgctcct caagttcctg   1140
cgcgcgcgcg agttcaaggt gaaggaggcc atggcgatgc tcaggtcggc cgtgctgtgg   1200
cgcaagcgct tcggcatcga gtccctcctc gacgccgacc tcgccctgcc ggagctcgac   1260
agcgtggtgt tctaccgcgg cgccgaccgc gagggccacc ccgtgtgcta caacgtctac   1320
ggcgaattcc aggacaagga cctgtacgag aaggcattcg gcgacgagga gaagcgggag   1380
cgcttcctca agtggcgcat ccagctgctg gagcgcggca tcctgtcgca gctcgacttc   1440
tcgcccagtg gcatctgctc catggttcag gtcacagacc tcaagaactc gccacctatg   1500
ctcggcaagc accgcgccgt cacccgccag gccgttgctc tgctccagga cgactacccc   1560
gagttcatcg ccaagaaggt gttcatcaat gtgccatggt ggtatctcgc tgccaacaaa   1620
atgatgagcc cgttcctcac gcagcgtacc aagagcaagt tcatttttgc cagcccagcc   1680
aaatcagctg agaccctctt cagatatatc gcaccagagc aagtccctgt ccaattcgga   1740
ggtctcttca aggaagatga tcctgagttc accacctcag acgccgttac cgagctcact   1800
atcaaacctt catcgaaaga aaccgttgag attcctgtca ctgagaattc cacgattgga   1860
tgggagctcc gggtgcttgg atgggaggtg agctacggag cagagttcac tcctgatgcc   1920
gagggtggat acacagtcat cgtgcagaaa acgaggaagg tgcctgcaaa tgaggaacca   1980
atcatgatag gcagcttcaa ggttggcgag ccaggaaaga ttgtgctaac gatcaacaac   2040
cctgcatcaa agaagaagaa gctcctctac agatccaagg tcaagagcac cagtgagtcc   2100
gtttgaggtt gcagctgcct gatcaccaga ttcaccacaa tggcagctga actcattccc   2160
tgatggaaga gaaacctttt ggttttggtt ctttaattta ttggttttgc tgttttggtt   2220
cacattttgt atttgtttaa ttaaaaacca aagtgagctt gtttttgtga tagttggaag   2280
gagagggttg atatgatata atgacatcgt gatggtttgt tgagggcaga ggacaaaaat   2340
tgtggaagga ctgaagaata tctgctgctt tgtatatctg tctgtacatt gcatctctgg   2400
attctcatgg acatgttaaa tttagaagta cttgtcatc                          2439
```

<210> SEQ ID NO 42

```
<211> LENGTH: 536
<212> TYPE: DNA
<213> ORGANISM: Oryza sativa
<220> FEATURE:
<221> NAME/KEY: misc_feature
<223> OTHER INFORMATION: LOCUS: AK062758 536 bp mRNA linear PLN
      04-DEC-2008; DEFINITION: Oryza sativa Japonica Group cDNA
      clone:001-106-G10, full insert sequence.; ACCESSION: AK062758

<400> SEQUENCE: 42

atcctgcaca cagccatttc acttgctttg ctccacgcct ccacctacct aaatcgctct     60

cattagtact caattaagtc gatcggcgag cgattcagcg cggctcctcg accgatctct    120

ccgtttcgtc agatcgatcg atcgatcgat cagggctgtg tattgcgccg tgtagtacgt    180

gagaggatcg gagtcggagc agcgagcgag atttgttgaa gcaaattaag tagatcgatc    240

tcatatcgat catccttaat taatttatca tggagctggt gctggtgata tcgctgccgc    300

tgctggcgct catcataatc gtcgccatcg tcctctgcgt catctgccgc tagcttagct    360

gattccttcc tgcctccgcg atcattttgc atacatgtag tatgtcagta tgtggtgcat    420

caaatgtgat cattttgccg cccgttgttg ttgggcacgg tgattgacga cagaaagaat    480

tactcccttc atattttaat gtatgacacc attgactttt taaccaacgt ttgacc        536


<210> SEQ ID NO 43
<211> LENGTH: 2026
<212> TYPE: DNA
<213> ORGANISM: Oryza sativa
<220> FEATURE:
<221> NAME/KEY: misc_feature
<223> OTHER INFORMATION: LOCUS: AK103306 2026 bp mRNA linear PLN
      04-DEC-2008; DEFINITION: Oryza sativa Japonica Group cDNA
      clone:J033125E13, full insert sequence.; ACCESSION: AK103306

<400> SEQUENCE: 43

gcgagccgcg cgagcgcgac acacacagag gaggaggccg cgcgcgcgac gcgagctcgc     60

cctctgcgtg cgccgccgcg aggtcgccgc cgccgccgcc gccgtcgatc ggcgcccgat    120

cgatggggag ctgctactcc gcctacgcct cctcgcgcaa gctgcgcggc cgcatcagca    180

agatctccct cgtcatcccc gacccggtcc ccgacgccga ggccgcctcg ccgcgcaagg    240

acggcgtcga tggcgacggc gacgacgtga ggggtggtgg tggtggctgt gacgatggcg    300

gtgacgtcgt cgccatcgcg acgacgacgg cggacgagtt cgcgcggcgg tacgtgctgg    360

ggaaggagct ggggcgcggg gagttcgggg tgacgcggcg gtgcagcgac gcggcgaccg    420

gggaggcgct ggcgtgcaag acgatccgga agcacaggcg cctggcgccg ccgcgggtga    480

ccgcggcgaa ggcggcggcc gcgcacgggg aggacgtgaa gagggaggtg gccatcatgc    540

ggcgcatgtc gtcggcgtcg tcgtcgcgcg ggggcggcgc cgcgtcgtcc gccgccgtgg    600

tgcggctccg cgaggcatgc gaggacgccg ccgacggctc cgtccacctc gtcatggagc    660

tctgcgaggg cggcgagctg ttcgaccgca tcgtggcgcg cggacactac tccgagcgcg    720

ccgccgccaa catcttccgc accatcgtcg acgtcgtcca gctgtgccac tcgaacgggg    780

tgatacaccg cgatctgaag ccggagaact tcctgttcgc gaacaaatcg gaggactcgc    840

cgctcaaggt catcgacttc ggcctctcgg tgttcttcaa gccaggcgac cggttcacgg    900

aggtggtggg gagcgcgtac tacatggcgc cggaggtatt gcggcggagc tacgggccgg    960

aggtggacgt gtggagcgcc ggcgtcatcc tctacatcct cctctgcggc gtccctccat   1020

tctggggaga caacgacgag aagatcgcgc aggcgatcct ccgcggcgcc atcgacttca   1080

acagggagcc attgccgagg gtctccgcca acgccaagga cctcgtcagg aggatgcttg   1140
```

```
atcctaaccc atccacccgc ctgacggcca aacaagttct tgagcatcca tggctgaaga   1200

acgcggacac ggcgccgaac gtgtcgctgg gcgacgccgt gcgggcgagg ctgcagcagt   1260

tctccgccat gaacaagttc aagaagaagg ctctcggagt ggtggcgcgg aacctgccgg   1320

gggaggaggt ggacaagtac gtgcagatgt tccaccacat ggacaaggac aagaacgggc   1380

acctgtcgct cgacgaactc ttggaaggcc tccacatcaa cggccagccc gtccccgagc   1440

ccgagatcag gatgctactc gaagccgcgg acacggacgg gaacgggacg ctggactgcg   1500

acgagttcgt gacggtgtcg gtgcacctga agaagatgag caacgacgag tacctggcgg   1560

cggcgttcaa ctacttcgac aaggacggca gcgggttcat cgagctggac gagctgcggg   1620

aggaggtggg cccaaacgag caggccatcc tggagatcct ccgcgacgtc gacaccgaca   1680

aggacggccg catcagctac caggagttcg agctcatgat gaagtccggc gccgactgga   1740

ggaacgcctc caggcacttc tccagggcca acttcagcac cctcagcagg aggctctgca   1800

aggatactct tactccctga tgatcgatga tgcccaacaa tctcatcaac tttgtttcat   1860

caaggcttat aaactgcaca tctttcacct tcaccagaca gggataacta gagagagata   1920

caagaccaac ttagagaaat gtattggagt ggcaacacga tgcgatgctg cgcttggatt   1980

gtgaaatgag aaatggaact gaaatgggga tcgtaccggt tttgct                  2026
```

```
<210> SEQ ID NO 44
<211> LENGTH: 1154
<212> TYPE: DNA
<213> ORGANISM: Oryza sativa
<220> FEATURE:
<221> NAME/KEY: misc_feature
<223> OTHER INFORMATION: LOCUS: AK061207 1154 bp mRNA linear PLN
      04-DEC-2008; DEFINITION: Oryza sativa Japonica Group cDNA
      clone:006-210-C03, full insert sequence.; ACCESSION: AK061207

<400> SEQUENCE: 44

atatcgatct gatctctcta tatattttat ggattacctc tctgttttta agggaagagc     60

tagcgatcga gctccagtag tatacgtgca ctttgggttg ctcatgcact ggcttaattt    120

ctgaagatga gtaatctgct caaggctaag agctgggtac cagaggagaa agctgcagcg    180

actgcttctg atgaacagaa tgacaagata aagaaagtcc gggaactcct gggaagccag    240

atgacagcag agatgccgtc attcttgtcg gacgccacca tccgccgctt cctccgggca    300

aggaactgga gcacggagca agcaaccaag gctctcaaag agactgtcaa atggaggcgt    360

cagtacaggc cggacacaat ccgctgggaa gacattcctg gaagggagca cgaagctagg    420

agaacatata tagccgacta ctttgataag aatggaagga tcgtcttcat atcgaatccg    480

acaattaaga gtaaatcatc caccaaggac cagataaaac agttagtgta taacctggag    540

atttttgcca tgcactcaga aaacatggaa gacgaatgta ctgtttggtt aactgacttt    600

caaggctggg tgctaacaaa tacgccattg ccgttgcttc gtgaatgcac tcacataatt    660

caaaaccatt atccagggct gatttctgtc gcaatcctca gcaacccacc aaggattttc    720

gaatcctttt ggaagattgt gtgctatttc attgagccaa agttgaaaga aaaagtgaag    780

ttcgtatata ctaacaatcc agagagccac aagatagttg ctgatatgtt tgatttggac    840

aagctggagt ctgcatttgg ggggaggaac acacttccat ttgacatgga caagtatgca    900

gagagaatga aacgaagtga ccaaatgaga ggagctccca tgcatgccaa tggctactct    960

tgctctaccc aaacctgacc acataaaagt tcaccttaat ttcttttagt ttcatataaa   1020

gtggcataaa tatatatacg ccggttagat ctgaataagt gatgcatgtc actcttaggt   1080
```

```
aggatttga ggcgggcgga cctgagtaaa actccatgac aaattatgta caaggaagaa   1140

gctaatcatg taat                                                    1154


<210> SEQ ID NO 45
<211> LENGTH: 1999
<212> TYPE: DNA
<213> ORGANISM: Oryza sativa
<220> FEATURE:
<221> NAME/KEY: misc_feature
<223> OTHER INFORMATION: LOCUS: AK068266 1999 bp mRNA linear PLN
      04-DEC-2008; DEFINITION: Oryza sativa Japonica Group cDNA
      clone:J013149A10, full insert sequence.; ACCESSION: AK068266

<400> SEQUENCE: 45

ttggtactca agccggaggc agcacactgc aacttaagtt tttctatagc tcctagcaag     60

ctagcaatgg ctccctcggt gatggcttcg tcggccacct ccgtggctcc cttccagggg    120

ctcaagtcca ctgcgggcct cccggtgaac cgccgctcca gcagctcgag ctttggcaac    180

gtcagcaatg gcggaaggat cagatgcatg caggtgtggc cgattgaggg cattaagaag    240

ttcgagactc tgtcgtactt gccgccattg acagtggagg accttttgaa gcagatcgag    300

tacctgctcc gatctaagtg ggtgccttgc ttggagttca gcaaggtcgg attcgtctac    360

cgtgagaatc acagatcacc cggatactat gacggtaggt actggaccat gtggaaactg    420

cccatgtttg gatgcaccga tgccacccaa gtgctcaagg agctcgagga ggcaaagaag    480

gcataccctg atgccttcgt tcgcatcatt ggctttgaca acgttaggca ggtgcagtta    540

atcagcttca tcgcgtataa gccaccgggt tgcgaggagt caggcggcaa ctaagcgctt    600

tcgttccttc gtgcatgttc tttctttttc tttttttttt ttgtgtgtcc gtgttaagct    660

gcacgtaatt gttctctcgc gctccgacct gccgttgttg caagagtact actacaacta    720

tcggtctatc gttcggtgac ggtgagacag ggcacgtgaa tgcaagatct ccggctatac    780

acacgtactc atgtaatatg atgcctagag catatctgaa tccgtcgaca atgaaatttt    840

ggttttgcaa aatgctggta tttgtttatc atcctggcac gtgatatttg cctagagcat    900

ctaaatcact tttacgaaat gtgcgcgtca acaaactgat acggcccaaa tgccagaaat    960

taccagcata tatagccata tcaacttttg attcgtatat atgaaggttg atttagttag   1020

agaaattcgg ttgtgagaga aggaggctag caaagattcg gttgatcaag ctgtaccgcc   1080

aggccaggac gtgctgtgcg cgcggctgtg ccgcttgacc gcagaaccat acggaattga   1140

cggaccaatt gtgcatacgg acttagctaa aataattgtt gatttttggc aataagaaaa   1200

gcgagtagca cataaaatct aaagtggatg agtaaaggga caaaatttta tacatgttca   1260

ggccttctcg atgagaagta atactatact cctgttttgg ggattatatt tgtcagatgt   1320

tgtatcaatc tgacgatcga gttatggtta ttgttggcgg ctgttaaata tcgattttat   1380

gccatcaata cctgtataat ttatacagaa ataataaaac attcaacata gtggtaggct   1440

ttaattctaa catattccat aagtgttggt gtatatttgg atgcaggtaa taaaccaccg   1500

aattaggagg aaatctagac taagttgaag gaaattttca tccatacaag tgttgggctt   1560

tttaactcca ttttaacacc aaaatgcaag cccaaaaacc tgcgaaatgg ataaggcaga   1620

ctgagaagga ggcccaggcc aaaacttggg ccagttgggc caagccaggt ttcggccaaa   1680

tcctgatcat cgctgttgat ctcagggttt ggcatggacg ctcttgattt actcctgatg   1740

gcagttgcag ggcatttccg atcattcgca tgctctacaa ccatcatacc tacttattta   1800

aggagctctc atcctcactt catatcacac actccaatct tgagctgaat tataagaggc   1860
```

```
tctattgtat tttattgtat actagaatta gggaaagatt aaggtcgtag aagaaatcgg   1920

aggaattccg gagttatcgg tgatcctttt ctatttctta tactttgtta tttgctttaa   1980

tagaaatatc atttcaagt                                                1999
```

<210> SEQ ID NO 46
<211> LENGTH: 822
<212> TYPE: DNA
<213> ORGANISM: Oryza sativa
<220> FEATURE:
<221> NAME/KEY: misc_feature
<223> OTHER INFORMATION: LOCUS: NM_001064530 822 bp mRNA linear PLN 08-JUN-2010; DEFINITION: Oryza sativa Japonica Group Os06g0598500 (Os06g0598500) mRNA, complete cds.; ACCESSION: NM_001064530

<400> SEQUENCE: 46

```
atgtcaccac aaacagaaac taaagcaagt gttggattta aagctggtgt taaggattat     60

aaattgactt actacacccc ggagtacgaa accaaggaca ctgatatctt ggcagcattc    120

cgagtaactc ctcagccggg ggttccgccc gaagaagcag ggctgcagt agctgccgaa    180

tcttctactg gtacatgcga agaaatgatt aaaagagctg tatttgcgag ggaattaggg    240

gttcctattg taatgcatga ctacttaacc gggggattca ccgcaaatac tagtttggct    300

cattattgcc gcgacaacgg cctacttctt cacattcacc gagcaatgca tgcagttatt    360

gatagacaga aaaatcatgg tatgcatttc cgtgtattag ctaaagcatt gcgtatgtct    420

gggggagatc atatccacgc tggtacagta gtaggtaagt tagaagggga acgcgatatg    480

actttaggtt ttgttgattt attgcgcgat gattttattg aaaaagatcg tgctcgcggt    540

atctttttca ctcaggactg ggtatccatg ccaggtgtta taccggtggc ttcagggggt    600

attcatgttt ggcatatgcc agctctgacc gaaatctttg gagatgattc tgtattgcaa    660

tttggtggag gaactttagg acatccttgg ggtaatgcac ctggtgcagc agctaatcgg    720

gtggctttag aagcctgtgt acaagctcgt aacaagggcg cgatcttgct cgtgaaggta    780

atgaaattat ccgatcagct tgcaaatgga gtcctgaact ag                       822
```

<210> SEQ ID NO 47
<211> LENGTH: 547
<212> TYPE: DNA
<213> ORGANISM: Oryza sativa
<220> FEATURE:
<221> NAME/KEY: misc_feature
<223> OTHER INFORMATION: LOCUS: AK119900 547 bp mRNA linear PLN 04-DEC-2008; DEFINITION: Oryza sativa Japonica Group cDNA clone:002-180-F02, full insert sequence.; ACCESSION: AK119900

<400> SEQUENCE: 47

```
aaaaaaaaaa aaaaaaaaaa acttggctgt tccgctgctg ccagcgctcg gctcggagcc     60

gccgtcgaca ccggtgccga ccgttggcgt gacggcggcg agccacctcg tcggctccgg    120

tggccacagc tacttggacg tcaggacaga agaggaattc aagaagggac atgtggagaa    180

ttctcttaat gtgccattcc tcttctttac ccctcaaggg aaggaaaaga acacaaagtt    240

catagagcag gtggcattgc attatgataa ggaggacaac ataattgtgg gttgcctaag    300

tggagtaaga tctgaactag catctgccga tctcatagca gccggattca aaaatgtaaa    360

gaacatggaa ggaggttaca tggcatgggt ggaaaatggc cttgcggtga ataaacctct    420

agtgcaagaa gagctctagt ttcagttatt gtatttttag ataatgactt tcagttattg    480

tatgactggg tgttaatttg atttgtagaa aggaaaggta taagaaaaca atgttatatt    540
```

attcccc 547

<210> SEQ ID NO 48
<211> LENGTH: 1803
<212> TYPE: DNA
<213> ORGANISM: Oryza sativa
<220> FEATURE:
<221> NAME/KEY: misc_feature
<223> OTHER INFORMATION: LOCUS: RICRTUB1X 1803 bp mRNA linear PLN 16-MAY-1995; DEFINITION: Rice beta-tubulin (RTUB-1) mRNA, complete cds.; ACCESSION: L19598

<400> SEQUENCE: 48

```
tccacccacc cctcgatctc tcgctcgccg ccgccgatcg gatcgcgtgg ttggatcatc     60

acaactcggc aaagatgaga gagatcctgc acatccaagg cgggcaatgt ggcaaccaga    120

tcggtgccaa attctgggag gtggtgtgtg atgagcatgg cattgaccct actgggcggt    180

acacaggcaa ctcagatctg cagttggagc gtgtcaatgt gtactacaat gaggcctcct    240

gcggtcgctt tgtgcctcgt gctgttctca tggaccttga gcctggtact atggacagtg    300

tccgcactgg accctatggc cagatcttcc ggcctgacaa ctttgtcttc gggcaatctg    360

gtgctggtaa caactgggcc aagggacact acactgaggg tgccgagcta attgattctg    420

ttttagatgt tgtgaggaag gaggctgaga actgtgactg cctgcaagga ttccaagtat    480

gccactctct tggtggtggt actggatctg gtatgggtac actgttgata tcaaagatca    540

gggaggagta ccctgaccgc atgatgctga cattctcagt tttcccctca ccaaaagtat    600

ctgatactgt ggttgagcca tacaatgcta cactctcagt ccatcagttg gttgagaatg    660

ctgatgagtg tatggttcgt gataatgagg ctctctacga catttgcttc aggactctca    720

agctgaccac acctagcttt ggggatttga accatttgat ttctgccacc atgagtggag    780

tcacatgctg cctaaggttc cctggtcagt tgaactctga cctccgtaag ctggcagtga    840

accttatccc ctttccccgt ctccacttct tcatggtcgg attcgccccg ctgacatcac    900

gtggctccca gcagtaccgt gcccttactg ttcctgagct cacacagcag atgtgggatg    960

ccaagaacat gatgtgcgct gctgatcctc gccatggccg ttacctcacc gcctctgcca   1020

tgttccgtgg aaagatgagc accaaggagg ttgatgagca gatgatcaat gtccagaaca   1080

agaactcatc ctacttcgtc gagtggatcc ccaacaatgt gaagtccagt gtctgtgaca   1140

ttccaccgag aggcctctcc atggcatcga ccttcattgg caactcaaca tccatccagg   1200

agatgttccg gagggtgagc gagcagttca ctgctatgtt caggaggaag gctttcttgc   1260

actggtacac tggcgaaggc atggacgaga tggagttcac cgaggcagag agcaacatga   1320

acgaccttgt ctctgagtac cagcagtacc aggatgccac cgccgatgag gagggcgagt   1380

acgaggacga ggagcagcag gaggctgacg acatgtaagg tggcttttgc ttggtggttc   1440

tagggcaggg ttttgtgtgc ttggtgtttc cgtcttacat tatcaccgta ttaccgcctc   1500

gtacgccacc gccggttcct atgtcttcgc tttgtttttt cgtctgtgct atgggaacct   1560

ttttgggtac tgtattactt gatgctggtc tgcgattgtt gatatttcgg gatgaatttt   1620

acctttccgc gttggtcctc gtgtgtaata tttgcaaatt acggaactag gaaggtagcc   1680

cgcgcattcg cgtgggcatg tatcgtaggc tgtatttgag ataatcgtaa gtaataggct   1740

gattgtgtta aaatgttgca tttgttatat agtaaactat aggcatatgg atcttaaaaa   1800

aaa                                                                 1803
```

<210> SEQ ID NO 49

```
<211> LENGTH: 568
<212> TYPE: DNA
<213> ORGANISM: Oryza sativa
<220> FEATURE:
<221> NAME/KEY: misc_feature
<223> OTHER INFORMATION: LOCUS: AK070851 568 bp mRNA linear PLN
      04-DEC-2008; DEFINITION: Oryza sativa Japonica Group cDNA
      clone:J023065B06, full insert sequence.; ACCESSION: AK070851

<400> SEQUENCE: 49

gacacagctg cactacttgc actgaagtag ctagagcttg caagtaaaga tggctaccac     60

caagcatttt gtgttgctaa taatccttgt cctccttagc ataggaatga ccactagtgc    120

tagaactctc ttgggttatg gcattggagg agaaggtggc ggtggtggag gaggaggtgg    180

tagcggcgga ggaggtggtg ggtatggtag cggctcaggc tatggatctg gcagcggata    240

tggtcaaggt ggcggtgctt atggtggagg atatggaagc ggtggtggtg gtggaggcgg    300

cggcggccaa ggcggaggat ctggctatgg ttctggctct ggctacgggt atggatccgg    360

aggaggtggt gggcactact agtcctatac tcggcaatgg agcaattcta ccgtgggact    420

tgtgcactca tatatgatga ttgtgtaaca ttggtatata cacaagcttg ttttcgtgat    480

tatatgtaat gcttcttgat tggcttgctc gctgcccaat atatgcgctt cccaagtata    540

aataaatcaa aaataaggtt gaaatacg                                      568


<210> SEQ ID NO 50
<211> LENGTH: 942
<212> TYPE: DNA
<213> ORGANISM: Oryza sativa
<220> FEATURE:
<221> NAME/KEY: misc_feature
<223> OTHER INFORMATION: LOCUS: NM_001051294 942 bp mRNA linear PLN
      08-JUN-2010; DEFINITION: Oryza sativa Japonica Group Os01g0840300
      (Os01g0840300) mRNA, complete cds.; ACCESSION: NM_001051294

<400> SEQUENCE: 50

atggagacga cgacgacgac gttgggcggc ggcggcggcg ggcgggcggg aggcttctcc     60

gatccgccgt ctccgctctc gccgccgctg tcgccggcct cggcggcggc ggcggcgctg    120

gcgaacgcgc ggtggacgcc gaccaaggag cagatcgcgg tgctggaggg gctgtaccgg    180

caggggctgc gcacgccgac cgccgagcag atacagcaga tcacggcgag gctccgggag    240

cacggccaca ttgagggcaa gaacgtgttc tactggttcc agaaccacaa ggcccggcag    300

cggcagaagc agaagcagca gagcttcgac tacttcagca agctgttccg ccgcccgccg    360

ccgctgcccg tgctccacag gccactcgcg cggcccttcc ctctcgccat ggcgccgacg    420

gcgatgccac cgccgccgcc gccgccggcg acgacgacga cggccgcatg caacgccggt    480

ggtgtgatgt tcaggacgcc aagcttcatg ccggtcgcga caaataacgc cagctactac    540

ccgcagcagc agacgccgtt gctgtaccca gggatggaag tgtgtccgca cgacaagtcc    600

acggcgcagc caccggccac caccaccatg tacctgcagg caccgccgag cagcgcacac    660

ctcgcggcgg cggctggccg cggcgcggcg gaagcggaag gccatggccg ccgcggcggc    720

ggcgccggtg ggcgcgagac cctccagctg ttccccctgc agcccacctt cgtgctgccg    780

gatcacaagc cgctccgcgc cgggagcgcc tgcgccgccg tgtccccgac gacgccgtcc    840

gcgtccgcgt cgttctcgtg ggagtcggag agctcggaca gccccagcag cgaggcgcct    900

ccgttctacg acttcttcgg cgtccattct ggaggccgct ga                       942


<210> SEQ ID NO 51
<211> LENGTH: 1152
```

```
<212> TYPE: DNA
<213> ORGANISM: Oryza sativa
<220> FEATURE:
<221> NAME/KEY: misc_feature
<223> OTHER INFORMATION: LOCUS: AK059805 1152 bp mRNA linear PLN
      04-DEC-2008; DEFINITION: Oryza sativa Japonica Group cDNA
      clone:006-204-G07, full insert sequence.; ACCESSION: AK059805

<400> SEQUENCE: 51

cagcttccac tccacgaaaa ccctctgcct ccttcgctcg ctgcaccctc gtctcggcga     60

tccatccatg gctgccagga agttcttcgt cggcggcaac tggaaatgca atgggacagg    120

ggaggacgtg aagaagatcg tcaccgtcct caacgaggcc gaggtgccct ccgaggacgt    180

cgtcgaggtg gtggtgagcc cgccgttcgt gttcctgccg caggtgaagg gtttgctccg    240

gccggacttc tccgtcgccg cgcagaattg ctgggtgcgc aagggcggcg ccttcactgg    300

cgagatcagt gccgagatgt tggtgaacct gcaggtgcct tgggtgattc tgggacactc    360

tgagcggaga gcgctgatgg gcgaatcaag tgattttgtt gctgacaaaa ttgcgtacgc    420

actttcccaa ggtatcaagg taattgcttg cattggtgag acccttgaac agagagaagc    480

aggaacaacg atggaagttg ttgcagcgca aactaaagct attgcagaga agatatccga    540

ttggaccaat gttgttttgg catatgaacc agtttgggcc attggaaccg gcaaggttgc    600

aacccctgct caggctcagg aggttcatga tggtctgaga aagtggcttg tgactaatgt    660

tagtcctgca gttgctgaat caaccaggat tatttacaga ggctccgtaa atggagcaaa    720

ctgcaaagaa cttgctgcta aacctgatgt tgatggattc cttgttggag gagcttcatt    780

gaagcctgaa tttgtggaca tcatcaagtc tgctaccgtc aagtcttctg cttagtgttc    840

tgggttgcaa ccagatgatc gtaggagtta atgctgccaa ttttaagtta tgacatgttt    900

gaccagcttg ctttgttata tctcgaagtc agtgaactcc atatcgttcc atagagcatg    960

cagccacctg tggttgcttt ttttcttttt gactttttct cccgagagga tcagatgaac   1020

tgaaagtgcc gttaatgtct gtattatcag aagtttgttg atggcttgat gctataatag   1080

ttgaacctga tacttcctga gtgaagtact gtcctttgca tgtttgattg gtgattactt   1140

gttttcgtag tc                                                       1152


<210> SEQ ID NO 52
<211> LENGTH: 1833
<212> TYPE: DNA
<213> ORGANISM: Oryza sativa
<220> FEATURE:
<221> NAME/KEY: misc_feature
<223> OTHER INFORMATION: LOCUS: AK106244 1833 bp mRNA linear PLN
      04-DEC-2008; DEFINITION: Oryza sativa Japonica Group cDNA
      clone:002-100-D03, full insert sequence.; ACCESSION: AK106244

<400> SEQUENCE: 52

ccacctcccc caccgccatc gccattgccg ccgacgagga agaggagaag cttcgagtgg     60

agcgatctcg atggacccgt gcccgttcgt gcgggtgctg gtcggcaacc tctcgctgaa    120

gatgccggtg gcgccgcgcc ccgccggagc cggggccggg gtgcacccat ccacctcgcc    180

gtgctactgc aagatccgcc tcaacaagct gccgtaccag accgccgacg cgccgctgct    240

gctgccgccc tcgccggagg catcggcggc gccggcgcca gcgccggcga cgggcgcgct    300

cgccgccgcg ttccacctct ccaaggccga cctcgaccgc ctcaccgcga agccgtcgct    360

gttcgggtcg cgcacggcga ggctgaagat cgtggtgtac gctggccgga ggggcaccac    420

gtgcggcgtc ggcggcggct ccgggaggct gctcgggaag gtggtcatcc cgctcgacct    480
```

```
caagggcgcc tcggcgaagc cggtggtgta ccacagcagc tggatctgca tcgggaagcg    540
cgggcgcaag ccctcgtcgg tgtcggcggc gaacgcgcag ctcaacatca cggtgcgcgc    600
cgagcccgac ccgaggttcg tgttcgagtt cgacggcgag ccggagtgca gcccgcaggt    660
gctccaggtg caggggagca tgaagcagcc catgttcacc tgcaagttct cctgccgcag    720
caacagcgac ctccgctccc ggtcaatgcc ggccgatatg gggagcggcg ggcgcaactg    780
gctgacggcg ttcggctccg acagggagcg ggcggggaag gagaggaagg ggtggtcggt    840
gacggtgcac gacctgtcag gctccccggt ggcgctggca tcaatggtga cgccgttcgt    900
ggcgtcgccg gggacggaca gggtgagcaa atccaacccg ggggcgtggc tggtgctccg    960
cccgggcgac ggcacgtgga agccatgggg tcgcctggaa tgctggcgcg agcgcggcgc   1020
gggcgccgcc gccggcgaca gcctcgggta ccggttcgag ctcgtcctcc ccgacccaac   1080
cggcatgggc gtgggcgtgt ccgtggcgga gtccaccatc ccggcgtcga agggcggccg   1140
gttcgcgatc gacctgacgg caacgcaaca gttcgggcgg agcgggtcgc cggcgtgcag   1200
cccgtgcggg agcggcgact acgggatgtg gccgttcggc agctgccgcg ggttcgtgat   1260
gtcggcggcg gtgcaggggg aggggaaatg cagccggccg gcggtggagg tgggcgtgca   1320
gaacgtcggg tgcgcggagg acgcggcggc gttcgtggcg ctcgccgccg ccgtcgacct   1380
gagcatggac gcgtgccggc tcttctccca ccgcctccgc cgcgagctct cggcgtcgcg   1440
ctccgacctg ctccggtgag gcacacgagg cggcggtgaa tcgatcgatc gatcggaatc   1500
gggaacaaca ttgtacagct agcgctagcg ttcgtcgtcg tcgttttctg gtctctgtcg   1560
tttttgttgg gtgatcagat tgtgttgtgt tttttatttt gtttttgaaa tcactactcg   1620
tgattttttt gtggtttttt tgggtggtga aatggtgatg agggggtttg taattttggt   1680
agacttctag gtgcttttta aagtctagaa gcagaggagg aagcagaaga agaagaagag   1740
caagttcggg atcatgatga atgaatgaac aagttataaa aacttttcgt gtctattatg   1800
ttttaaattt caaattcgga gtttattttg gcc                                1833
```

<210> SEQ ID NO 53
<211> LENGTH: 954
<212> TYPE: DNA
<213> ORGANISM: Oryza sativa
<220> FEATURE:
<221> NAME/KEY: misc_feature
<223> OTHER INFORMATION: LOCUS: AK108127 954 bp mRNA linear PLN 04-DEC-2008; DEFINITION: Oryza sativa Japonica Group cDNA clone:002-139-D06, full insert sequence.; ACCESSION: AK108127

<400> SEQUENCE: 53

```
acaaccagca gcgcagttac acccaaacca gcagcatcga cgattcgccg agctaggggc     60
agaggcagaa gtgcagaacg tacacgcgtg gtgagcagag gagcaatggc gactcggctt    120
ctgctgctgc tgctgctctt gctcggcatg tcgctgaaag gatcagaggg ggcgtggtgc    180
gtgtgcaggc cggacgtggc ggaggcggcg ctgcagaagg cgctggacta cgcgtgcggg    240
cacggcgcgg actgcgcccc ggtgacgccg agcgggtcgt gctacagccc aaacaacgtg    300
gcggcgcact gctcctacgc cgccaacagc tacttccagc ggaattccca ggccaagggc    360
gccacctgcg acttcggcgg cgccgccacc ctctcctcca ccgaccccag ctcaggaacc    420
tgcaaatacc ctgcaaccgc aagtgctgca gggacaagca ccggaaccgg cacggcgggt    480
gcaggcacag gcaccggtac aagcacgagc acgagcacga gcacttcttc cccgggctct    540
tcaactgcag ccacgggtac gccgatcatg ggagggacct tcgctacgcc gatcggcggc    600
```

```
ggcgcgtctg ggccgacgac tagcgccttg aatcctgaca gcagcgaagc accgtccccg    660

tcccttggac gtcatcttct cctcacgtgc attgcctcca tgctgctctc taattttctt    720

ttggcgtagt aatttggccg gaaagtaacg tgaactgaag cagcatactg tgggagaatg    780

gagatttggc tttccttttc tgctttggag cttgtcgcgg cctgttcttt ttctttacca    840

gaactgcagg tcctgggtgt ttacacctgt tgtaccagtg cccagtgaac tggccgtttg    900

catcatggca tgtttagtat gttatcgtgc tagtgtcagc acattctcac tgat          954
```

```
<210> SEQ ID NO 54
<211> LENGTH: 1100
<212> TYPE: DNA
<213> ORGANISM: Oryza sativa
<220> FEATURE:
<221> NAME/KEY: misc_feature
<223> OTHER INFORMATION: LOCUS: AK061237 1100 bp mRNA linear PLN
      04-DEC-2008; DEFINITION: Oryza sativa Japonica Group cDNA
      clone:006-211-C03, full insert sequence.; ACCESSION: AK061237

<400> SEQUENCE: 54

atcagatcaa agcaagcaaa caacaacaaa aaccacttct cgtgggtaga agagagagag     60

agcgaggcga tttcgaccaa gaagatggcc gggatcgtgg tggtgttcga cttcgacaag    120

acgatcatcg acgtcgacag cgacaactgg gtcgtggacg ggctcggcac gacggaggag    180

ttcgagcggc tgctgcccac catgccgtgg aacaccctca tggacaccat gatgggcgag    240

ctccacgcga gcggcaagtc gctcgccgac gtcgcgggcg tgctcaggtc ggcgccgctc    300

gacccgcgcg tcgtcgccgc catcaaggcc tgctacggcc tgggctgcga cctccggatc    360

ctcagcgacg ccaaccgctt cttcatcgac accatcctcg accaccacgg cctcacgggt    420

tacttctccg agatcaacac caacccgagc gccgtcgacg ccgccaccgg ccgcctccgc    480

atcgcgccgt accacgactt ccacgccggc ccgcacgggt gcggcctcgg gatctgcccg    540

cccaacatgt gcaagggcca ggtgctcgac cgcatccgcg cctccgccgg cgccgccggc    600

aagagggtca tctacctcgg tgacggccgc ggcgactact gcccgtcgct ccgcctcggc    660

cgcgacgact tcatgatgcc acgcaggggc ttccccgtgt gggagctcat ctgcgaggac    720

ccgtcgctgc tccacgcgga ggtgcactcg tgggccgacg gcgccgagat ggaggagacg    780

ctgctgcggc tggtcggcag ggtgctcctc gaggagagga acctgccgcc gctcgactgc    840

aagctcgagt cgttgccggc cgtcgccgtg caggacggca tgcccatgac gctccggatc    900

aagaactgat caatggcggc gacgaacgta cgcatgattt cgagcgcgaa acggctagct    960

cgaacaatgt gtgtgtgagg attgcgatac gggtataatt ttaactattg actgattttt   1020

gcgctacgcg tgattgagcc tgcgattagt agaggctcat tgtatcttgt ccgatcaatt   1080

gaagtaaaac atttggcttg                                               1100
```

```
<210> SEQ ID NO 55
<211> LENGTH: 459
<212> TYPE: DNA
<213> ORGANISM: Oryza sativa
<220> FEATURE:
<221> NAME/KEY: misc_feature
<223> OTHER INFORMATION: LOCUS: AK062517 459 bp mRNA linear PLN
      04-DEC-2008; DEFINITION: Oryza sativa Japonica Group cDNA
      clone:001-104-C09, full insert sequence.; ACCESSION: AK062517

<400> SEQUENCE: 55

ataagcaagg gaaatatcag catctgcaaa aatcatctca gattcgttcg ccatggcgag     60

gatcccgttc gccgccatcg tcgtcgccat cctctctttc gccatcgccg cggctgcaca    120
```

```
ggcgcccgcg ccgtctccca ccagcgacgg gacgtcggtg gatcaaggga tcgcatacct    180

gctgatgatc gtggcgctgg tgctcaccta cctcatccac cctctcgacg cctcctccgc    240

ctacaagctc ttctgagctt atgcagagat ctcttcgtcg ccatggtgtt ccttctcctt    300

cttggatctc ctcctcctcc cttttgatag tctagtggtg gatctctcat tctcggtgta    360

attaattagt gggattttta tattcttttt cagctcgcgt tcgtttgtaa tttgggtcgg    420

tggtactgcg ctgaggatcg atttcgcatt gtgtatatc                           459
```

<210> SEQ ID NO 56
<211> LENGTH: 3707
<212> TYPE: DNA
<213> ORGANISM: Oryza sativa
<220> FEATURE:
<221> NAME/KEY: misc_feature
<223> OTHER INFORMATION: LOCUS: AK065259 3707 bp mRNA linear PLN 04-DEC-2008; DEFINITION: Oryza sativa Japonica Group cDNA clone:J013002J18, full insert sequence.; ACCESSION: AK065259

<400> SEQUENCE: 56

```
ggcctccaaa aaaaaccatt tgggtctctc tccctttgag agccccctac cgacacttgt     60

ttgcccttaa tttctatata tcccccacgt actttacgac ccatttctca cacccctctt    120

ctcctcctcc tcttcttctc caccacctcc attgctgctc gcctctctca cctcctcctc    180

ctcctcttgt gtggagctcg tcggcgtcga ggtgtagcta gctagctaag cttgttttgc    240

cattgttgtg ttcttggtgt tcggagaggg agcttgcctt tgccttgagg ggagaggcaa    300

aggcattagc aatggcgcca gcggtggccg gcggcggagg gaggaggaac aatgaggggg    360

tgaacgggaa cgcggcggcg ccggcgtgcg tgtgcgggtt cccggtgtgc gcgtgcgcgg    420

gggcggcggc ggtggcgtcg gcggcgtcgt cggcggacat ggacatcgtg gcggcggggc    480

agatcggcgc cgtcaacgac gagagctggg tcgccgtcga cctcagcgac agcgacgacg    540

cccccgccgc cggcgacgtc cagggcgccc tcgacgaccg ccccgtcttc cgtaccgaga    600

agatcaaggg cgtcctcctc caccccctacc gggtgctgat ctttgtgagg ctgatcgcgt    660

tcacactgtt cgtgatatgg cgtatcgagc acaagaaccc ggacgcgatg tggctgtggg    720

tgacgtcgat cgccggcgag ttctggttcg ggttctcgtg gctgctcgac cagctcccca    780

agctgaaccc gatcaaccgc gtccccgacc tcgccgtcct ccgccgccgc ttcgaccacg    840

ccgacgggac ctcctccctc ccggggctgg acatcttcgt caccaccgcc gacccgatca    900

aggagcccat cctgtcgacg gcgaactcca tcctctccat cctcgccgcc gactaccccg    960

tcgaccgcaa cacctgctac ctctccgacg actctgggat gctcctcacc tacgaggcca   1020

tggcggaggc ggccaagttc gcgacgctgt gggtgccctt ctgccggaag cacgccatcg   1080

agccgcgcgg gcctgagagc tacttcgagc tcaagtccca cccctacatg gggagggcgc   1140

aggaggagtt cgtcaacgac cgccgccgcg tccgcaagga gtacgacgac ttcaaggcca   1200

ggatcaacgg cctcgagcac gacatcaagc agaggtccga ctcctacaac gccgccgccg   1260

gcgtcaagga cggcgagccc cgcgccacct ggatggccga cgggtcgcag tgggagggca   1320

cctggatcga gcagtcggag aaccaccgca agggcgacca cgccggcatc gtcctggtgt   1380

tgctgaacca cccgagccac gcacggcagc tggggccgcc ggcgagcgcc gacaacccgc   1440

tggacttcag cggcgtggac gtgcggctgc cgatgctggt gtacgtcgca cgtgagaagc   1500

gccccgggtg caaccaccag aagaaggccg gcgccatgaa cgcgctgacc cgcgcctccg   1560

ccgtgctctc caactccccc ttcatcctca acctcgactg cgaccactac atcaacaact   1620
```

```
cccaggcgct ccgcgccggc atctgcttca tgctcggccg cgacagcgac accgtcgcgt   1680
tcgtccagtt cccgcagcgc ttcgagggcg tcgaccccac cgacctctat gctaaccaca   1740
accgtatctt cttcgacggc acgctccgtg ccctcgacgg gctgcagggg cctatctacg   1800
tcggcaccgg gtgtctcttc cgccgcatca cgctgtacgg gttcgagccg ccgaggatca   1860
acgtcggcgg accgtgcttc ccgaggctcg gtgggatgtt cgccaagaac aggtaccaga   1920
agcctgggtt cgagatgacc aagcctggtg ccaagccggt ggcgccgccg ccggcggcga   1980
cggtggcgaa ggggaagcac gggttcctgc cgatgcccaa gaaggcgtac ggcaagtcgg   2040
acgcgttcgc cgacaccatc ccgcgcgcgt cgcacccgtc gccgtacgcg gcggaggcgg   2100
cggtggcggc cgacgaggcg gcgatcgcgg aggccgtgat ggtgacggcg gcggcgtacg   2160
agaagaagac cgggtggggg agcgacatcg ggtgggtgta cggcacggtg acggaggacg   2220
tggtgaccgg ctaccggatg cacatcaagg ggtggaggtc gcgctactgc tccatctacc   2280
cgcacgcgtt catcgggacg gcgccgatca acctgacgga gaggctgttc caggtgctcc   2340
ggtggtcgac gggttcgctg gagatcttct tctcgaggaa caacccgctg ttcgggagca   2400
cgttcctgca cccgctgcag cgcgtggcgt acatcaacat caccacctac ccgttcacgg   2460
cgctgttcct catcttctac accaccgtgc cggcgctgtc gttcgtgacg gggcacttca   2520
tcgtgcagag gccgaccacc atgttctacg tctacctcgc catcgtgctc gggacgctgc   2580
tcatcctcgc cgtgctggag gtgaagtggg cgggggtcac cgtgttcgag tggttcagga   2640
acgggcagtt ctggatgacg gccagctgct ccgcctacct cgccgccgtg ctgcaggtgg   2700
tcaccaaggt ggtgttccgg cgggacatct cgttcaagct cacctccaag ctccccgccg   2760
gcgacgagaa gaaggacccc tacgccgacc tgtacgtggt gcggtggacg tggctcatga   2820
tcaccccccat catcatcatc ctcgtcaaca tcatcggctc cgccgtcgcc ttcgccaagg   2880
tgctcgacgg cgagtggacg cactggctca aggtcgccgg cggcgtgttc ttcaacttct   2940
gggtcctctt ccacctctac cccttcgcca agggcatcct cgggaagcac ggcaagacgc   3000
cggtggtggt gctcgtctgg tgggccttca ccttcgtcat caccgtcgtg ctctacatca   3060
acatccccca catccatggc cccggccgcc acggcgccgc ctcaccatcc cacggccacc   3120
acagcgccca tggcaccaag aagtacgact tcacctacgc ctggccatga ggacgccgtc   3180
gccggagacg aagaagaaaa cacaaacaag aacaagacga caccaacaac accaacaaca   3240
acaaacacga gatgagtacg ttctactaca cgctgctgca acaacacata ctactgaaca   3300
ctgtgcatgc atttgatcga gcgacccgcc aaaatttgaa agtttttttt cttcttttct   3360
tttaaccttt ttttttcctc tttttgcccc ctcctctctc tccttttctt tctttttagt   3420
tttgtccaga aaaaagatgg tgtttatttg atttagtttt ttaattacct gtggtaatta   3480
attatgtatt atacattact gcaaggaaga gaggggggct tacaggtggg gcccgggggg   3540
tggggtgtgg tgtatgattg tactgtacat gctgggagat gtatgtatac ggagacaaaa   3600
agacaagagt cacagagagt gagagaaaga gaggctggaa gtgggcccgg ccaggtggtg   3660
gtggtattct tttagtacat ggaaacaata aatttaattt cattatt                 3707
```

<210> SEQ ID NO 57
<211> LENGTH: 1323
<212> TYPE: DNA
<213> ORGANISM: Oryza sativa
<220> FEATURE:
<221> NAME/KEY: misc_feature
<223> OTHER INFORMATION: LOCUS: AK065604 1323 bp mRNA linear PLN 04-DEC-2008; DEFINITION: Oryza sativa Japonica Group cDNA clone:J013034F24, full insert sequence.; ACCESSION: AK065604

<400> SEQUENCE: 57

```
gttagctctc gctctcgcag ctcaaccact agcagcagcg gcaggaaggc gagaggagga      60

atcggaggta gctggacggc ggcgaggcga cgacgagccg gggtggtgca gcaagaacgg     120

cgcggcgagc ggcggggagg agagattgga tcgacgccgg gtagttagga agggagcttg     180

gagagatggc ggcttccgcg aggcccgtcg gcgtcggcgg ggagagggcg acgagcttcg     240

ccatggcgtg cagcctgctc agccgctacg tccgccagaa cggcgccgcc gccgccgagc     300

tcggcctcgg catcagaggt gagggtgagg ctccgagggc ggcgccggcg acgatgagct     360

tgctgcccgg ggaggcggag aggaagaagg agaccatgga gctcttcccg cagagcgccg     420

gctttggcca gcaggatgcc atcaccgccg attctgctgc tgatgctagg gaacaagagc     480

ctgagaggcg tcagctgacc atcttctatg gtgggaaggt gctcgtgttc aacgacttcc     540

cagccgacaa ggcaaagggc ttgatgcagc tggctagcaa gggcagcccg gtggctcctc     600

agaatgccgc ggcacctgca ccagcagctg ttacagacaa caccaaggcc cctatggccg     660

tgccggcccc ggtcagtagc ttgcctacag ctcaggccga tgctcagaag cctgctcgcg     720

cgaatgcttc tgatatgcct attgctagga aggcatcact ccacaggttc cttgagaaga     780

gaaaggatcg tcttaatgca aagacgccat accaggcttc tccttcagat gcaaccccag     840

tcaagaagga gcctgagagc caaccatggc tcggactagg gccgaacgcc gtcgtgaagc     900

ccatagaacg cggccaatga ggttgcatgg aaacttcacc aaagctcttc aaaaatatat     960

gaaatgcgct tgccgttaga gtaccaaatc atatatgttc tctcataccc catgttttag    1020

tgttttttct ttagttcgtg cttctatgtt gttcacttgt cacatagttc tgaatgtaaa    1080

ggaaaaaggt agtagcattg acgaccagtg ccgagagcct gagagaagtt ttggcatgtt    1140

aacacatggt gactctgaaa atggccatgc taaggtaaaa agttattgca aaggaaacat    1200

atatgtatct tctgaaattc tgatcatctg gctttgtcct tggctctagc cttgctctat    1260

gcaaagcaaa gtgattgtaa tggattcaga atataattca tattcctatt gttgatttct    1320

gtt                                                                  1323
```

<210> SEQ ID NO 58
<211> LENGTH: 1077
<212> TYPE: DNA
<213> ORGANISM: Oryza sativa
<220> FEATURE:
<221> NAME/KEY: misc_feature
<223> OTHER INFORMATION: LOCUS: AK106964 1077 bp mRNA linear PLN 04-DEC-2008; DEFINITION: Oryza sativa Japonica Group cDNA clone:002-119-F09, full insert sequence.; ACCESSION: AK106964

<400> SEQUENCE: 58

```
actctcctcc attccttcac tgccttcact tccctgctca gctcagcagc tcagggactt      60

cgaggatgat ggaatccaaa gcagccatga tggtgaccat cctgctctgc tgctcctcca     120

tctcaccggc gttcgcgcag aagcacaagg gtccgcccgc cgcggcggcc gtaagcctcc     180

cgccgtcgcc ggcgccgtcc ccggcggcgc cgcgccacgt ggacctcgcc gacctcctga     240

gcgtggcggg tccgttccac acgttcctcg acctcctgga gaagacggac gtgctcagga     300

cgttccagag ccaggcgaac ggcagcaagg acgggatcac ggtgttcgtc cccaaggacg     360

cggcgttcgc gtcgctggcg aggtcggcga cggcgaacct cacctccgac cagctcaagt     420

cgctggcgct gtaccacgcg ctgccgaggt actactccct cgccgagttc aacaggctgg     480
```

```
gcggcgcggc cagcccggtg cccacgctcg ccggcggcga gtacacggtc aacgtcaccg    540
acgacatggg caccgtccat gtcgggtcga tgtggtccaa ccccaagatc agcagcagcg    600
tctactccac ccgccccgtc gccgtctacg aggtggacag ggtgctcctc ccgatgcaga    660
tcttcaggac cgacccgccc atggcgccgt cgccggcgcc ggcgccggac gccaagccgg    720
cctccgacgc cgccagcccg ctccccggga agtcgtcgag cgccaaggcg aaggcggacg    780
agaagaagag ctcgtcgtcg ccgccgtcgt cgcgccgcgg cgccggcatt gccggctact    840
tcttggctct tgctgcatct gcctcagctg gattgctgct cctgtgttga tgctaagaaa    900
cttttctaat tcttttttt tttgcatgga ttgttggttg ctggataatt ttattctttg    960
gacatagtag gggcattgtg ttaggattaa gttttatggg agtatttccg tcatatgctt   1020
gtatgattag tcgatgacta cttgtttatc cgatgcatgt tgcgaattgc acaaggt      1077
```

```
<210> SEQ ID NO 59
<211> LENGTH: 1347
<212> TYPE: DNA
<213> ORGANISM: Oryza sativa
<220> FEATURE:
<221> NAME/KEY: misc_feature
<223> OTHER INFORMATION: LOCUS: AK060983 1347 bp mRNA linear PLN
      04-DEC-2008; DEFINITION: Oryza sativa Japonica Group cDNA
      clone:006-203-A12, full insert sequence.; ACCESSION: AK060983

<400> SEQUENCE: 59

aaaaaaaaaa aaaaaaaaaa aaaaaattag cttagctagt gttagcgagc tccactgcca     60
gatcaagaag aagctagaga gagagcagag gagcaagcag atcaagaaga agaagacgag    120
gaagatgcac gccaagacgg actcggaggt gacgagcctg gcgccatcgt cgccgccgcg    180
gtccccgacg tcgcgcggcg ggcggccggt gtactacgtg cagagcccgt cgagggactc    240
gcatgacggg gagaagacgg cgacgtcggt gcactcgacg ccggcgctga gccccatggg    300
gtcgccgcgg cactcggtgg gcagggactc ctcgtccagc cgcttctccg gccaccccaa    360
gcgcaagggc gacaagtcca gctccggccg caagggcgcc ccggcgggga aggggtggca    420
ggagatcggc gtgatcgagg aggagggcct cctcgacgac gaggacgagc gcaggggcat    480
ccccaagcgc tgcaagtact tcctcatctt cgtcctcggc ttcgtcgtcc tcttctcctt    540
cttcgccctc gtcctctggg gcgccagccg ctcccagaag ccacagatag tcatcaagag    600
catcacgttc gacaacttca taatccaggc ggggacggac gcgtcgctgg tgccgacgga    660
catggcgacg accaactcga cggtgaagct gacgtaccgg aacacgggca cgttcttcgg    720
gatccacgtg acggcggacc cgttcacgct gtcgtacagc cagctgacgc tggcgtccgg    780
cgatctcaac aagttctacc aggcccggag cagccggagg acggtgagcg tgggggtgat    840
ggggaacaag gtgccgctgt acggcggagg gccgacgctg acggcgggga agggcagcgg    900
cagcatggct ccggtgccga tgatcctgag gacgacggtg cactcgaggg cgtacgtgct    960
gggggcgctg gtgaagccca agttcacacg cgccatcgag tgcaaggtcc tcatgaaccc   1020
cgccaagctc aacaagccca tctccctcga caagtcctgc atttacctct gaatccatca   1080
tattcattca ttattatcac ctgctcctcg gatcacctcc attcctgctg cttctttctt   1140
cctttctctc tacgatctga tctgtgcatt cttcctttc ttttttcctt tttgcggatc   1200
caacaacagc cataaatatg tatgtactgt atttcccagt cagattcgtt attataccaa   1260
acgatcaatt cgttgcagat tgatgagatc gatcgatcag gtggcagaaa atgaaataca   1320
cagagctgag tatgcttatc tttcgag                                       1347
```

<210> SEQ ID NO 60
<211> LENGTH: 2714
<212> TYPE: DNA
<213> ORGANISM: Oryza sativa
<220> FEATURE:
<221> NAME/KEY: misc_feature
<223> OTHER INFORMATION: LOCUS: AK099719 2714 bp mRNA linear PLN 04-DEC-2008; DEFINITION: Oryza sativa Japonica Group cDNA clone:J013088B06, full insert sequence.; ACCESSION: AK099719

<400> SEQUENCE: 60

```
gacaccaaga gaaaaatttt ttttccaaga aacgaaagcg aaatcaacct gcaattacca     60

gcataaatca atcaatcgga aaagcagagg ccacaacgat ctctctctcc agtctcgact    120

ccccagctac cacctcctct cctctcctct ctcctccatg agctttgcct agatcacagc    180

tggatttctt ggccgcatcc tcctcttctt ccaggtctct tccagctagc tagcttgttc    240

ttcccttccc tttctttttg ccttgtgcgc gtgaggatca gtgagctgtg cggctctctt    300

ttcttgttct tgctggactg ctgctgcctt aaaagatcct gcctttcttg ctcactttcc    360

ccggaggaga gagagaggag atccacatct ctgatggttc ttgggatctc ctaggagttg    420

tttctacctg tgctgctgct gctgatttct tcttcgattt gctagcggct gtgtggtcgg    480

agctcgtctt cttggttcga gatctcgaca ccttctgaga tggatttttt caccgagtac    540

ggtgagggaa acaggtacaa gatagaagag gttataggaa aagggagtta tggtgtggtt    600

tgctctgctt tggacactca caccggtgat aaagttgcta tcaagaaaat caatgacatc    660

tttgagcatg tgtccgatgc aacacggata cttcgcgaga tcaagttgct tagactcctg    720

cgacatccgg atatcgtgga aattaagcat attctacttc ctccatcaag gagagaattc    780

aaggatatct acgttgtttt tgaactcatg gagtctgatt tgcaccaagt tataaaggcc    840

aacgatgact tgactcctga acactaccag tttttcttgt atcagttgct ccgaggactg    900

aaatatatac acacagcttt ttgcagcaaa tgtatttcat cgagatctca aaccaaaaaa    960

tatcttggcg aatgctgatt gtaagctcaa aatatgtgat ttcggccttg caagggtagc   1020

ttttagtgat actccaaccg ccatcttctg gacggattat attgcaacaa ggtggtaccg   1080

agcaccagag ctgtgtggat ctttttttctc caagtataca ccagcaatag atatatagag   1140

tattggctgc atatttgccg agcttttaac cggaaaacct cttttccctg ggaagaatgt   1200

ggttcatcaa cttgatataa ttacagatct actaggaaca ccttctccag aaacaatatc   1260

taggattaga aatgagaagg caagacgtta cttgaacagt atgaggcgga aaaaacctat   1320

accatttaca cagaagttcc caaatgcaga tccacttgca atgcggttgt tagagagaat   1380

gttagctttt gatccaaaag atcggccaag tgctgaggag gcgcttgctg atccttattt   1440

caagaacata gccaatgttg atagagagcc ttctgctcaa cctatcacaa agctagagtt   1500

tgagttcgag aggcggagaa ttactaagga agatataagg gaactcatat atagagaaat   1560

tctggagtat catccaaaga tgctgaggga gttccttgag ggaactgagt ccactggttt   1620

catgtaccca agtgcagtag accattttaa aaaacagttt gcataccttg aagaacatta   1680

tgccaaggga tcaacagcag ctccacctga gagacaacat aactcattac caaggccttg   1740

tgttgtctat tcagataacc ggccacaaag cacagccagt gtcactgagg atctttccag   1800

gtgtttaatc agagacaaca atctaaaatc acaggattct gcttcagtcg gtgcaagcag   1860

aatccctcaa ggtgctgctg caagacctgg taaagcagtt ggttcggtgc tgcgttacgg   1920

taactgttcg acatccgctg ctgagcaaca atatgagcag cgaagggttg ttcggaaccc   1980
```

-continued

```
agcaattgct ccaaacagca gtgttcctct ggggagctca taccccagaa gaaaccagac   2040

ctgcaagagt gaaacaggtg atgttgaaag gatcgattcc agccaaaccg gtccaccgaa   2100

gccatatgtg gcgaacaaac tgcctgctac cgtcgatggt cggagtggcc actggtaaat   2160

ttctgcagcg caccagcgaa aacgctagtt attaccacag catcagcatg ggtttattgt   2220

tctatgtagt aaattcttag acatttaaaa catgtcattc tgtacagact tgtattgttt   2280

cttgggggct tttccatgat aaaaacagta gaattgtact gcaagcccta gtggattagg   2340

ctgcctgttt cttcatttct tcatagctca acctctgaat gatctggtac acaaacaaga   2400

tctcatggaa ttggacatca catgattcag ttcgaagggg gtatagtgga aactggaagc   2460

aacaagtgga ctgtaacatt ttcttgctga gaaaacaagg gactctttac tgacctgact   2520

gatgctgcta ttcaatttat tttccaagta aatccgaaga aggatcatgt aaacagcaca   2580

atgttggaca ttgctttagt atttcgttct caggaacatt gttccctttg cagagctagg   2640

agctgcaact atgtactact atctgacatt gctgtaactt gtaaaactta attgcatttc   2700

aagtattttc cctc                                                     2714
```